(12) United States Patent
Kellogg et al.

(10) Patent No.: US 9,944,597 B2
(45) Date of Patent: Apr. 17, 2018

(54) POLYSUBSTITUTED PYRROLES HAVING MICROTUBULE-DISRUPTING, CYTOTOXIC AND ANTITUMOR ACTIVITIES AND METHODS OF USE THEREOF

(71) Applicants: Glen E. Kellogg, Ashland, VA (US); Chenxiao Da, Chapel Hill, NC (US); Ashutosh Tripathi, Bryan, TX (US); John T. Gupton, Midlothian, VA (US); Nakul Telang, Richmond, VA (US); James A. Sikorski, Chesterfield, MO (US); Susan L. Mooberry, San Antonio, TX (US); Cristina Rohena, San Antonio, TX (US)

(72) Inventors: Glen E. Kellogg, Ashland, VA (US); Chenxiao Da, Chapel Hill, NC (US); Ashutosh Tripathi, Bryan, TX (US); John T. Gupton, Midlothian, VA (US); Nakul Telang, Richmond, VA (US); James A. Sikorski, Chesterfield, MO (US); Susan L. Mooberry, San Antonio, TX (US); Cristina Rohena, San Antonio, TX (US)

(73) Assignees: THE BOARD OF REGENTS OF THE UNIVERSITY OF TEXAS SYSTEM, Austin, TX (US); VIRGINIA COMMONWEALTH UNIVERSITY, Richmond, VA (US); UNIVERSITY OF RICHMOND, Richmond, VA (US)

( * ) Notice: Subject to any disclaimer, the term of this patent is extended or adjusted under 35 U.S.C. 154(b) by 0 days.

(21) Appl. No.: 15/021,972

(22) PCT Filed: Sep. 16, 2014

(86) PCT No.: PCT/US2014/055781
§ 371 (c)(1),
(2) Date: Mar. 15, 2016

(87) PCT Pub. No.: WO2015/039073
PCT Pub. Date: Mar. 19, 2015

(65) Prior Publication Data
US 2016/0297757 A1    Oct. 13, 2016

Related U.S. Application Data

(60) Provisional application No. 61/878,360, filed on Sep. 16, 2013.

(51) Int. Cl.
C07D 207/34 (2006.01)
C07D 207/36 (2006.01)
(Continued)

(52) U.S. Cl.
CPC ......... *C07D 207/34* (2013.01); *C07D 207/36* (2013.01); *C07D 207/46* (2013.01);
(Continued)

(58) Field of Classification Search
None
See application file for complete search history.

(56) References Cited

U.S. PATENT DOCUMENTS

| 5,502,051 A | 3/1996 | Scharfenberg et al. ... 514/235.5 |
| 2007/0082872 A1 | 4/2007 | Pinney ........................... 514/80 |

(Continued)

FOREIGN PATENT DOCUMENTS

| EP | 312723 | 4/1989 |
| EP | 0358047 | 3/1990 |

(Continued)

OTHER PUBLICATIONS

Da et al. Developing novel C-4 analogues of pyrrole-based antitubulin agents: weak but critical hydrogen bonding in the colchine site. Medchemcomm. 2013; 4(2): 417-421.*

(Continued)

*Primary Examiner* — Anna Pagonakis
(74) *Attorney, Agent, or Firm* — Norton Rose Fulbright US LLP

(57) ABSTRACT

The present invention provides polysubstituted pyrrole compounds, pharmaceutically effective salts, prodrugs, solvates and hydrates thereof, having antimitotic, antiproliferative and cytotoxic activity, activity against cells expressing the drug efflux protein, P-glycoprotein, or cells expressing the (Continued)

NT-7-16
$EC_{50} = 34.5$ nM

β-III isotype of tubulin and antitumor activity. Also provided are methods of utilizing these compounds for inhibiting the proliferation of cancer cells as well as their medical use, in particular for treating cancer, including drug resistant cancer.

15 Claims, 10 Drawing Sheets

(51) Int. Cl.
  $C07D\ 207/46$ (2006.01)
  $C07D\ 403/04$ (2006.01)
  $C07D\ 403/06$ (2006.01)
  $C07D\ 403/12$ (2006.01)
(52) U.S. Cl.
  CPC ......... $C07D\ 403/04$ (2013.01); $C07D\ 403/06$ (2013.01); $C07D\ 403/12$ (2013.01)

(56) References Cited

U.S. PATENT DOCUMENTS

| 2008/0275103 A1 | 11/2008 | Arlot | 514/423 |
| 2014/0135333 A1 | 5/2014 | Fatheree et al. | 514/236.8 |

FOREIGN PATENT DOCUMENTS

| GB | 2202406 | 9/1988 |
| JP | 07196608 | 8/1995 |
| WO | WO 03/057669 | 7/2003 |
| WO | WO 08/155081 | 12/2008 |
| WO | WO 09/121033 | 1/2009 |
| WO | WO 09/062371 | 5/2009 |
| WO | WO 09/065600 | 5/2009 |
| WO | WO 10/103065 | 9/2010 |
| WO | WO 11/042477 | 4/2011 |
| WO | WO 11/138409 | 11/2011 |
| WO | WO 12/031090 | 3/2012 |
| WO | WO 12/120135 | 9/2012 |

OTHER PUBLICATIONS

Sausville et al. Contributions of human tumor xenografts to anticancer drug development. Cancer Research, 2006; 66:(7). Apr. 1, 2006.*
Johnson et al. Relationships between drug activity in NCI preclinical in vitro and in vivo models and early clinical trials. British Journal of Cancer, 2001, 84(10), 1424-1431.*
Alvarez, et al., "Endowing indole-based tubulin inhibitors with an anchor for derivatization: highly potent 3-Substituted indolephenstatins and indoleisocombretastatins." J Med Chem. 56, pp. 2813-2827, 2013.
Bai, et al., J Biol Chem 275:40443-52, 2000.
Banwell, et al., "Palladium-Catalysed Cross-Coupling and Related Reactions Involving Pyrroles ," Eur J Org Chem. 14, pp. 3043-3060, 2006.
Canela, et al., "Novel colchicine-site binders with a cyclohexanedione scaffold identified through a ligand-based virtual screening approach." J Med Chem. 57, pp. 3924-3938, 2014.
Chen, et al., J Med Chem. 55:7285-9, 2012.
Cooney, et al., "Cardiovascular safety profile of combretastatin a4 phosphate in a single-dose phase I study in patients with advanced cancer." Clin Cancer Res. 10, pp. 96-100, 2004.
Da, et al., "Developing novel C-4 analogues of pyrrole-based antitubulin agents: weak but critical hydrogen bonding in the colchicine site," Med Chem Comm. 4(2), pp. 417-421, 2013.
Da, et al., ACS Med Chem Lett. 3:53-57, 2012.
Da, et al., J Med Chem. 56:7382-95, 2013.
Dumontet et al., Nature Review Drug Discovery. 9:790-803, 2010.
Gupton, et al., "Synthesis and Cytotoxicity of 2,4-Disubstituted and 2,3,4-Trisubstituted Brominated Pyrroles in Murine and Human Cultured Tumor Cells," Arch Pharm Med Chem. 333, pp. 3-9, 2000.
Gupton, et al., "Application of 2-substituted vinamidinium salts to the synthesis of 2,4-disubstituted pyrroles," J Org Chem. 55, pp. 4735-4740, 1990.
Handy, et al., "A modular synthesis of the lamellarins: total synthesis of lamellarin G trimethyl ether." J Org Chem. 69, pp. 2362-2366, 2004.
Hanefeld et al., "Synthesis of isopentabromopseudilin," Liebigs Ann Chem. 9, pp. 865-869, 1991.
International Preliminary Report on Patentability in International Application No. PCT/US2014/055781 dated Mar. 31, 2016.
International Search Report and Written Opinion in International Application No. PCT/US2014/055781 dated Dec. 19, 2014.
Kemnitzer, et al., "Discovery of 4-aryl-4H-chromenes as a new series of apoptosis inducers using a cell- and caspase-based high throughput screening assay. 4. Structure-activity relationships of N-alkyl substituted pyrrole fused at the 7,8-positions." J Med Chem. 51, pp. 417-423, 2008.
LaRegina, et al., J Med Chem. 54:8394-06, 2011.
Lu, et al., Pharm Res. 29:2943-71, 2012.
Lucas, et al., "4-Acyl Pyrroles: Mimicking Acetylated Lysines in Histone Code Reading," Angew Chem Intl Ed. 52, pp. 14055-14059, 2013.
Mooberry, et al., Mol Pharmacol. 72:132-40, 2007.
Nguyen, et al., "A common pharmacophore for a diverse set of colchicine site inhibitors using structure-based approach." J Med Chem. 48, pp. 6107-6116, 2005.
Palermo, et al., "Drug-induced inhibition of tubulin polymerization induces mitochondrion-mediated apoptosis in yeast." Cell Cycle. 10, pp. 3208-3209, 2011.
Risinger, et al., "Microtubule dynamics as a target in oncology." Cancer Treat Rev. 25:255-61, 2009.
Sattler, et al., "A novel small molecule met inhibitor induces apoptosis in cells transformed by the oncogenic TPR-MET tyrosine kinase," Cancer Res. 63, pp. 5462-5469, 2003.
Williams, et al., Tetrahedron Lett. 54(32):4292-95, 2013.
Tripathi, et al., Bioorg Med Chem. 16:2235-2242, 2008.

* cited by examiner

POLYSUBSTITUTED PYRROLES HAVING MICROTUBULE-DISRUPTING, CYTOTOXIC AND ANTITUMOR ACTIVITIES AND METHODS OF USE THEREOF

PRIORITY PARAGRAPH

This application is a national phase application under 35 U.S.C. § 371 of International Application No. PCT/US2014/0055781, filed Sep. 16, 2014, claims priority to U.S. provisional application Ser. No. 61/878,360, entitled "*Microtubule Depolymerization and Antiproliferative Disrupting Activities at the Colchicine Site of Alpha, Beta-Tubulin*", filed Sep. 16, 2013. The entire contents of each of the above-referenced disclosures are specifically incorporated herein by reference without disclaimer.

STATEMENT REGARDING FEDERALLY FUNDED RESEARCH

This invention was made with government support under 2R15CA-067236 awarded by the National Institutes of Health. The government has certain rights in the invention.

BACKGROUND

Field of the Invention

Certain embodiments are related generally to the field of oncology and chemistry. More particularly, embodiments are related to design and synthesis of tubulin-binding polysubstituted pyrrole compounds and their medical use for the treatment or prevention of hyperproliferative diseases such as cancer.

Background of the Invention

A large number of targets are under exploration as chemotherapeutic treatments for cancer. The clinical efficacy and commercial successes of paclitaxel and the vinca alkaloids have established tubulin and microtubules as validated targets in cancer therapy (Risinger et al., Cancer Treat. Rev. 35, 255-61 (2009)). Accordingly there have been major ongoing efforts to identify new tubulin-disrupting agents that bind to tubulin and interfere with microtubule/tubulin function. Microtubules are filamentous cytoskeletal polymers composed of tubulin and are extremely important in mitosis, cellular signaling, and homeostasis. Tubulin is a α,β-heterodimer, and these heterodimers align in a head-to-tail orientation forming protofilaments that then associate to form hollow, cylindrical microtubules. Microtubules are dynamic structures, and microtubule dynamics are critically important for normal cellular functions. As components of mitotic spindles in dividing cells, microtubules are very sensitive to microtubule-disrupting agents. Compounds that bind tubulin and target microtubules perturb mitosis and interfere with normal cellular signaling leading to the inhibition of cellular proliferation and initiation of cytotoxicity. These microtubule-targeting agents interact with tubulin at four major binding sites: the taxane and laulimalide/peloruside A sites for microtubule-stabilizing agents, and the vinca and colchicine sites for microtubule-destabilizing agents.

Colchicine was the first drug known to bind to the tubulin protein, inhibit microtubule formation, and cause loss of cellular microtubules. Colchicine itself is not used as an anti-cancer agent due to its low therapeutic index against cancer cells and dose-limiting toxicities. Vinca alkaloids bind their cognate site and induce microtubule depolymerization similar to colchicine. In contrast, paclitaxel and its analogs stabilize microtubules and inhibit microtubule dynamics. As a result, taxanes interfere with the normal microtubule-dependent events, including cell division, which culminates in apoptosis. Paclitaxel together with docetaxel, nab-paclitaxel and cabazitaxel forms the drug category of the taxanes. Taxanes and vinca alkaloids have achieved notable success in cancer chemotherapy, but no colchicine-site targeting agents have been approved for systemic use against cancer (Dumontet and Jordan, *Nature Reviews Drug Discovery*, 9, 790-803 (2010)).

A major drawback to using many microtubule-targeting agents as anti-cancer drugs in the clinic is innate and acquired drug resistance. This resistance commonly arises due to overexpression of the drug efflux pump protein, P-glycoprotein (Pgp). This membrane-associated transporter is expressed in many cancer cell lines and in patients. Expression of Pgp reduces intracellular drug concentrations and limits overall drug cytotoxicity. The poor clinical response of some patients to the taxanes and vinca alkaloids can be attributed to the expression of Pgp. In contrast, many cochicine-site directed microtubule-targeting agents do not act as substrates for Pgp-mediated efflux.

Another significant mechanism of drug resistance is the abnormal expression of the β-III-tubulin isoform. Of the known β-tubulin human subtypes, expression of class III β-tubulin can lead to drug resistance to both taxanes and vinca alkaloids and is associated with poor prognosis in patients (Seve and Dumontet *Lancet Oncol*. 9, 168-175 (2008)). Thus, there is an ongoing need to identify new microtubule-targeting agents that are not limited by such resistance mechanisms.

Another drawback to the taxanes, such as paclitaxel and related analogs, is their high molecular weight and low water solubility. These properties dictate that their clinical application is limited to intravenous routes of administration. There is therefore an ongoing need for smaller molecular weight compounds with higher water solubility that would have the potential for alternative routes of delivery, particularly oral delivery.

Despite some success, the discovery of new, more efficacious colchicine-site-directed inhibitors is becoming increasingly important because of drug resistance to the tubulin-binding agents used clinically. In any case, the true therapeutic potential of the colchicine site on tubulin has not been fully explored because of the dynamic nature of tubulin and its ability to interact with such a wide variety of natural and synthetic structural subtypes (podophyllotoxins, arylindoles, sulfonamides, 2-methoxyestradiols, and flavonoids) at the colchicine binding site. To date, these limitations have prevented the determination of an atomic-level, three-dimensional structure of tubulin with inhibitors bound at the colchicine-binding site that would have the atomic resolution required for drug design (Bhattacharyya et al., *Med. Res. Rev.* 28, 155-83 (2008)).

Two potential cholchine binding sites on β-tubulin have been mapped using covalent adducts with two related chloroacetly colchicine derivatives (Bai et al., *J. Biol. Chem.* 275, 40443-52 (2000)). The first site was entirely encompassed within β-tubulin with the 2- and 3-chloroacetyl thiocholchine ester derivatives forming adducts with Cys-354. The second potential site was located at the α/β interface of tubulin and involved forming adducts with Cys-241 that are less stable. A more comprehensive pharmacophore model for structurally diverse cholchicine-like tubulin inhibitors has been reported using a combination of docking and molecular dynamics. This model described a cleft at the alpha/beta interface as the colchicine-binding site (Nguyen et al., *J. Med. Chem.* 48, 6107-16 (2005)). However, the degree of resolution still requires considerable computational effort to be useful to predict new potential inhibitor structures bound to the site. In addition, the model was unable to correctly predict the conformations of some of the colchicine-site inhibitor molecules.

Recently, a more comprehensive approach combining ensemble docking and structure activity relationships with multiple diverse chemical series, hydropathic analyses and 3D-QSAR provided an atomic-scale colchicine site model more consistent with target structure conformation and at higher resolution than the 3.6 Angstrom resolution protein structure currently available for tubulin (Da et al., *J. Med. Chem.* 56, 7382-95 (2013)).

Accordingly, provided herein is the first evidence that this new model can be used predictably for rational drug design to identify a select subset of pyrrole-based colchicine site inhibitors that provide new compounds with dramatically and unexpectedly improved potency and cytoxic activity to cancer cells with demonstrated antitumor activity.

Combretastatin A-4 (CA-4) is a naturally occurring polymethoxylated stilbenoid phenol that resembles portions of the colchicine structure. CA-4 binds tubulin at the colchicine site and inhibits polymerization. CA-4 has potent cytotoxicity against multiple cancer cell lines. However, only the cis-configuration of CA-4 is biologically active, while the corresponding trans-form exhibits little biological activity. Photochemical isomerization of cis-CA-4 to its trans isomer hinders its use therapeutically. Other limitations of CA-4 are due to its low water solubility and high lipophilicity, which lead to poor formulatability.

Consequently, more soluble forms of CA-4 have been investigated. The corresponding monophosphate prodrug (CA-4P) is currently being evaluated in clinical trials as a treatment for solid tumors to possibly overcome this limitation. CA-4P is by itself essentially inactive, but is readily converted by endogenous phosphatases in vivo to CA-4. In Phase 1 dose escalation studies, intravenous administration of CA-4P induced significant side effects: most notably cardiovascular modifications due to prolongation of the QTc interval (Cooney et al., *Clin. Cancer Res.* 10, 96-100 (2004)). These cardiovascular side effects present a difficult challenge to using CA-4P as a therapeutic agent, and point to the need to identify safer compounds. A number of related CA4 analogs are in clinical trials, refueling the search for novel colchicine site agents.

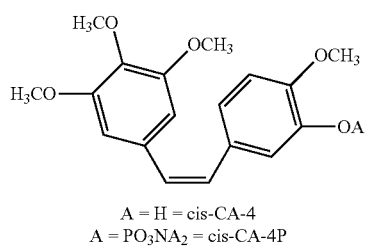

A = H = cis-CA-4
A = PO$_3$NA$_2$ = cis-CA-4P

A variety of small molecules with diverse molecular scaffolds have been shown to bind tubulin at the colchicine site (Lu et al., *Pharm. Res.* 29, 2943-71 (2012)). Many of these incorporate the 3,4,5-trimethoxyphenyl moiety found in CA-4 and are made with rigid heterocyclic or carbocyclic cores to prevent photoisomerization.

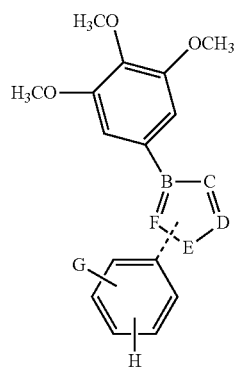

More recently, several structurally diverse tubulin polymerization inhibitors have also been identified including 2-(3-indolyl)-4-(3,4,5-trimethoxybenzoyl)-imidazoles (Chen et al., *J. Med. Chem.* 55, 7285-89 (2012)), 3-(3,4,5-trimethoxyphenyl-thio)indoles (LaRegina et al, *J. Med. Chem.* 54, 8394-06 (2011)) and substituted cyclohexandiones (Canela et al, *J. Med. Chem.* 57, 3924-38 (2014)).

Certain tetrasubstituted pyrroles have also been reported with potent cytotoxicity against murine and human cancer cell lines (Gupton et al., *Arch. Pharm. Pharm. Med. Chem.* 333, 3-9 (2000)). Notably, among this series, 4-[(3,4-dimethoxy)-phenyl]-3,5-dibromopyrrole 2-carboxylic acid ethyl ester (JG-03-14) was identified as a potent microtubule depolymerizer (Mooberry et al., *Mol. Pharmacology*, 72, 132-40 (2007)). JG-03-14 exhibited antiproliferative activity against a variety of cancer cell lines with an average IC$_{50}$ value of 62 nM. JG-03-14 caused a dose-dependent loss of cellular microtubules, formation of aberrant mitotic spindles, and accumulation of cells in the G2/M phase of the cell cycle. These events culminated in the initiation of apoptosis. JG-03-14 inhibited the polymerization of purified tubulin in vitro, consistent with a direct interaction between JG-03-14 and tubulin. JG-03-14 potently inhibited the binding of [$^3$H]colchicine to tubulin, suggesting that it bound to tubulin at a site overlapping the colchicine site. Moreover, JG-03-14 is a poor substrate for transport by P-glycoprotein. After i.p. dosing at relatively high doses, JG-03-14 had antitumor effects in the PC-3 xenograft model, in which it caused greater than 50% reduction in tumor burden after 14 days of treatment.

While active in animal models, JG-03-14 lacked sufficient potency to be considered as a clinical candidate. Surprisingly, the corresponding 4-[(3,4,5-trimethoxy)-phenyl]-3,5-dibromopyrrole 2-carboxylic acid ethyl ester was more than 350-fold less active than JG-03-14 in vitro against cancer cell lines (Da et al., *J. Med. Chem.* 56, 7382-95 (2013)).

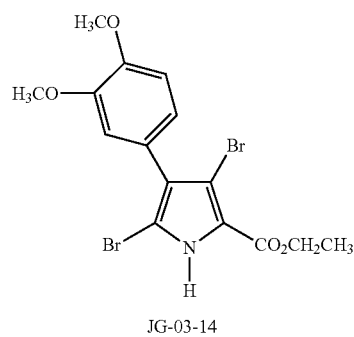

JG-03-14

International patent application WO2011/042477 assigned to Karo Bio AB describes substituted 4-hydroxyphenyl pyrroles and imidazoles as estrogen receptor ligands.

International Patent application WO2010/103065 assigned to BASF SE describes fungicidal compositions containing substituted pyrrole compounds.

International patent application WO2009/121033 assigned to the University of Southern California describes certain nitrogen heterocycle compounds and their use for treating various diseases.

International patent application WO2008/155081 assigned to Syngenta Participations AG describes substitutd aromatic heterocyclic compounds as fungicides.

International patent application WO2009/062371 assigned to Shanghai Hengrui Pharmaceutical Co., LTD describes certain N-oxazolidinonylmethyl pyrroles as CETP inhibitors and their use for treatment of hyperlipidemia and atherosclosis.

Japanese patent JP07196608 assigned to Nippon Soda Co. describes the preparation of pyrrole derivatives as incsecticides, acaricides and agrochemical fungicides.

Japanese patent JP54103865 assigned to Nippon Soda Co. describes phenylpyrrole derivatives and their use as fungicides.

Japanese patent JP46007247 assigned to Fujisawa Pharmaceutical Co., LTD describes formyl-substituted pyrrole carboxylates.

Japanese patent JP46005457 assigned to Fujisawa Pharmaceutical Co., LTD describes 4-phenyl-5-aminomethylpyrroles.

International patent application WO2012/120135 assigned to Novartis AG describes the preparation of isoxazole derivatives for controlling parasites.

International patent application WO2012/031090 assigned to Harvard College, USA describes small molecule inhibitors of ebola and lassa fever viruses and their methods of use.

International patent application WO2003/057669 assigned to Takeda Chemical Industries, LTD describes the preparation of pyrrole derivatives as androgen receptor antagonists.

US patent U.S. Pat. No. 5,502,051 assigned to Arzneimittelwerk Dresden G.m.b.H., Germany describes analgesic and anticonvulsant 3-aminopyrroles.

U.S. patent application 2014/0135333 assigned to Theravance, Inc. describes certain substituted pyrrole carboxamides as antihypertensive agents.

The 3-ethyl-5-methyl-4-acetyl-pyrrole 2-carboxamide, XD-14, has been reported to have interesting lead anticancer activity due to its interaction with histone bromo domains [Lucas et al., *Angew. Chem. Intl. Ed.* 52, 1-6 (2013)].

Palermo et al. report [*Cell Cycle*, 10, 3208-09 (2011)] that whereas 5-bromo-3-[(3,4,5-trimethoxyphenyl)thio]indole is a potent inhibitor of tubulin polymerization that induces apoptosis in yeast, N-(3,4,5-trimethoxyphenyl)pyrrole 2-carboxylic acid lacks significant activity.

International patent application WO2011/138409 assigned to the University of Bayreuth and Martin Luther University describes certain 4,5-diaryl-imidazoles containing pendant 4-(3,4-dimethoxy-5-halo)phenyl or 4-(5-amino) phenyl groups as combretastatin analogs with potent anticancer activity.

International patent application WO2009/065600 assigned to the Technische Universitaet in Dresden, Germany describes a method to design novel modulators of myosin using critical residues in myosin's interaction with pentabromopseudilin that can be used to design new compounds and pharmaceutical compositions for treating myosin-related diseases.

Various pyrrole-fused chromenes containing a pendant (3,4-dimethoxy-5-bromo)phenyl moiety have been reported as potent anti-cancer agents that inhibit tubulin polymerization [Kemnitzer et al., *J. Med. Chem.* 51, 417-23 (2008)].

The 2,4-dimethyl-5-vinylogous-pyrrol-3-carboxamide, SU11274, has been reported as a potent Met inhibitor that induced cell cycle arrest and dose-dependently reduced cancer cell growth [Sattler et al., *Cancer Res.* 63, 5462-69 (2003)].

The synthesis of isopentabromopseudilin has also been described [Hanefeld and Laatsch, *Liebigs Ann. Chem.* 865-69 (1991)].

European patent 0358047 assigned to American Cyanamid Co. describes the preparation of various phenylpyrrole derivatives and their method of use to control phytopathogenic fungi.

British patent 8803788 assigned to American Cyanamid Co. describes the preparation of various arylpyrrole derivatives and their method of use as pesticides.

European patent 312723 assigned to American Cyanamid Co. describes the preparation of various arylpyrrole derivatives and their method of use as molluscides.

Japanese patent 42006746 assigned to Fujisawa Pharmaceutical Co. describes the preparation of trihalopyrrole derivatives and their use as bactericides and fungicides.

It is therefore an object of the present invention to provide improved pyrrole compounds, pharmaceutical compositions containing such compounds and methods using such compounds for the treatment of abnormal cellular proliferation diseases, particularly cancer, including drug resistant cancer.

SUMMARY

Certain embodiments are directed to the design and synthesis of tubulin-binding polysubstituted pyrrole compounds that disrupt the cellular cytoskeleton network as well as methods for using these compounds to inhibit proliferation of a hyperproliferative cell, and their medical use for the treatment or prevention of hyperproliferative diseases or conditions, such as cancer. In certain aspects the methods are directed to the treatment or prevention of drug resistant cancer.

It has been discovered that certain polysubstituted 4-(2, 3,4-trimethoxy)phenyl-pyrroles, in contrast to the 4-[(3,4,5-trimethoxy)phenyl]-3,5-dibromo-pyrrole 2-carboxylic acid ethyl ester (JG-03-14 analog), are potent microtubule depolymerizing agents that cause loss of cellular microtubules, interrupt mitosis, inhibit proliferation, cause cytotoxicity, and have the ability to overcome drug resistance in cancer cells.

Certain embodiments are directed to polysubstituted 4-[(2,3,4-trimethoxy)phenyl]-pyrrole compounds of Formula I or Formula II and derivatives, analogs, tautomeric forms, stereoisomers, polymorphs, pharmaceutically acceptable salts, pharmaceutically acceptable solvates, pharmaceutically acceptable hydrates, pharmaceutically acceptable prodrugs, and pharmaceutical compositions containing them or their mixtures.

These unsymmetrical polysubstituted 4-[(2,3,4-trimethoxy)phenyl]-pyrrole compounds of Formula II have significantly lower molecular weights than the taxane derivatives. In particular, water-solubilizing functional groups can be readily introduced into the unsymmetrical polysubstituted 4-[(2,3,4-trimethoxy)phenyl]-pyrrole compounds of Formula II providing the opportunity for more flexible dosing, particularly oral delivery.

In certain aspects polysubstituted 4-[(2,3,4-trimethoxy)phenyl]-pyrrole compounds of Formula I or Formula II have antiproliferative and/or cytotoxic activities. In a further aspect, the compounds are effective in drug resistant cells. For example, the compounds provide a poor substrate for the drug efflux pump, P-glycoprotein (PgP), and retain their antiproliferative and cytotoxic activities in both paclitaxel-sensitive and paclitaxel-resistant cancer cells.

Certain embodiments are directed to methods of treating a hyperproliferative disease, such as cancer. In certain aspect cancer includes, but is not limited to leukemia, lymphoma, non-small cell lung cancer, colon cancer, central nervous system cancer, melanoma, ovarian cancer, renal cancer, bladder cancer, prostate cancer, pancreatic cancer, breast cancer, and/or pediatric cancers. In certain aspects the cancer is a drug resistant cancer.

Other embodiments are discussed throughout this application. Any embodiment discussed with respect to one aspect of the invention applies to other aspects of the invention as well and vice versa. Each embodiment described herein is understood to be embodiments that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. Embodiments may be better understood by reference to one or more of these drawings in combination with the detailed description of the specification.

DESCRIPTION

Figure 1:
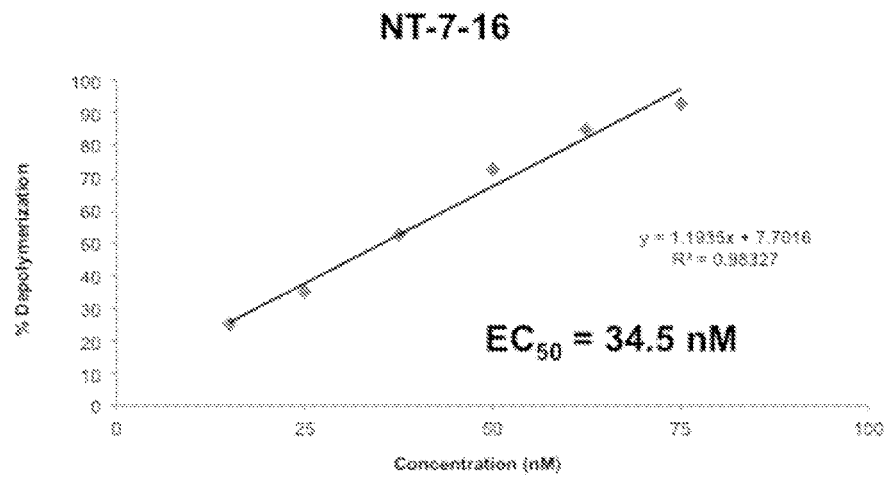
FIG. 1 is a graph showing the concentration-dependent effects of NT-7-16 on cellular microtubule disruption in A-10 cells that was used to calculate an $EC_{50}$, the concentration that causes 50% loss of cellular microtubules.

Certain embodiments are directed to polysubstituted 4-(2,3,4-trimethoxyphenyl)pyrrole compounds of Formula I. In certain aspects the compounds described herein have antiproliferative and/or cytotoxic activities. In a further aspect, the compounds described herein are effective against drug resistant cells. In still a further aspect the compounds described herein inhibit paclitaxel-sensitive and paclitaxel-resistant cells.

In one embodiment, compounds, pharmaceutical compositions, as well as methods of treatment or prophylaxis of a proliferative disease, and in particular cancer, comprise administering to a host in need thereof a compound of Formula I or a pharmaceutically acceptable salt, solvate, hydrate or prodrug thereof.

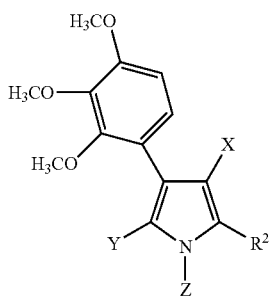

Formula I

Certain embodiments are directed to compounds having a chemical formula of Formula I where X and Y are the same or different, and are independently selected from chloro, bromo, iodo, and fluoro (i.e., a halo).

In certain aspects Z is selected from the group consisting of $R^1$, —OH, —$OR^1$, —$NH_2$, —N(H)—$R^1$, —$NR^1R^{10}$, —C(O)—$R^1$, —C(O)—$OR^1$, —C(O)—C(O)—$OR^1$, —C(O)—C(O)—$NR^1R^{10}$, —C(O)—$NH_2$, —C(O)—N(H)—$R^1$, —C(O)—$NR^1R^{10}$, —C(O)—N(H)—C(O)—$R^1$, —C(O)—N(H)—$S(O)_2$—$R^1$, —$S(O)_2$—$R^1$, —$S(O)_2NR^1R^{10}$, and —C(O)H. In certain aspects $R^1$ and $R^{10}$ are the same or different, and are independently selected from the group consisting of hydrogen, $C_1$-$C_8$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more substituent independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, amino, aminoalkyl, —$NR^{11}R^{12}$, oxo, imino, cyano, carboxy, carboxyalkyl, alkoxycarbonyl, —$OR^5$, —$SR^5$, —$C(O)R^5$, —C(O)—$NH_2$—C(O)—N(H)$R^{11}R^{12}$, —$S(O)_n$—$R^5$ (where n is 0, 1, 2, or 3), —$S(O)_2$—$NH_2$, —$S(O)_2$—N(H)$R^{11}$ and —$S(O)_2$—$NR^{11}R^{12}$; wherein $R^5$ is selected from the group consisting of hydrogen, $C_1$-$C_6$ straight alkyl, $C_3$-$C_6$ branched alkyl, $C_3$-$C_6$ cyclic alkyl, aryl, heteroaryl, heterocycle, and acyl, wherein all may be substituted by one or more substituent independently selected from the group consisting of halo, alkyl, lower alkyl, alkenyl, cycloalkyl, acyl, hydroxy, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^{11}$, —$C(O)R^{11}$, —C(O)—$NH_2$, —C(O)—N(H)$R^{11}$, —C(O)—$NR^{11}R^{12}$, —$S(O)_n$—$R^{11}$ (n is 0, 1, 2, or 3), —$S(O)_2$—$NH_2$, —$S(O)_2$—N(H)$R^{11}$ and —$S(O)_2$—$NR^{11}R^{12}$; and $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

$R^2$ is independently selected from $R^3$, —C(O)—$OR^3$, cyano, —C(O)—OH, —C(O)$R^3$, —C(O)—N(H)—OH, —C(O)—$NH_2$, —C(NH)—N(H)—OH, —$S(O)_2$—$R^3$, $S(O)_2$ $NH_2$, —C(O)—C(O)—$OR^3$, —C(O)—C(O)—OH, —C(O)—N(H)—$R^3$, —C(O)—$NR^3R^{10}$, —C(O)—N(H)—C(O)—$R^3$, —C(O)—N(H)—$S(O)_2$—$R^3$, $S(O)_2NH$—C(O)—$R^3$, —$S(O)_2NR^3R^{10}$, heteroaryl, heteroaralkyl, heteroaroyl, heterocycle, C(O)—heterocycle, and heterocyclicalkyl. In certain aspects $R^{10}$ is as described above. In other aspects $R^3$ is independently selected from the group consisting of $C_1$-$C_6$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more substituent independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^6$, —$SR^6$, —$C(O)R^6$, —C(O)—$NH_2$, —C(O)—N(H)$R^{11}$, —C(O)—$NR^{11}R^{12}$, —$S(O)_n$—$R^6$ (n is 0, 1, or 2), —$S(O)_2$—$NH_2$, —$S(O)_2$—N(H)$R^{11}$ and —$S(O)_2$—$NR^{11}R^{12}$. In certain aspects $R^6$ is selected from the group consisting of hydrogen, $C_1$-$C_6$ straight alkyl, $C_3$-$C_6$ branched alkyl, $C_3$-$C_6$ cyclic alkyl, aryl, heteroaryl, heterocycle, and acyl, wherein all may be substituted by one or more substituent independently selected from the group consisting of halo, alkyl, lower alkyl, alkenyl, cycloalkyl, acyl, hydroxy, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^{11}$, —$C(O)R^{11}$, —C(O)—$NH_2$, —C(O)—N(H)$R^{11}$, —C(O)—$NR^{11}R^{12}$, —$S(O)_n$—$R^{11}$ (n is 0, 1, 2, or 3), —$S(O)_2$—$NH_2$, —$S(O)_2$—N(H)$R^{11}$ and —$S(O)_2$—$NR^{11}R^{12}$. In a further aspect $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

In certain aspects Z and $R^2$ taken together can optionally form a 4- to 12-membered saturated or unsaturated heterocyclic or carbocyclic ring, wherein all may be substituted by one or more substituent independently selected from the group consisting of halo, alkyl, lower alkyl, alkenyl, alkynyl, cycloalkyl, acyl, hydroxy, hydroxyalkyl, haloalkoxy, thioalkyl, heterocyclic, heteroaryl, aryl, amino, aminoalkyl, —$NR^{11}R^{12}$, imino, oxo, thiono, thiol, cyano, carboxy, carboxyalkyl, alkoxycarbonyl, —$OR^{11}$, —$C(O)R^{11}$, —C(O)—$NH_2$, —C(O)—N(H)$R^{11}$, —C(O)—$NR^{11}R^{12}$, —$S(O)_n$—$R^{11}$ (n is 0, 1, 2, or 3), —$S(O)_2$—$NH_2$, —$S(O)_2$—N(H)$R^{11}$ and —$S(O)_2$—$NR^{11}R^{12}$, where $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

In certain aspects $NR^{11}R^{12}$ can optionally form a 4- to 12-membered saturated or unsaturated heterocyclic or carbocyclic ring, wherein all may be substituted by one or more substituent independently selected from the group consisting of halo, alkyl, lower alkyl, alkenyl, alkynyl, cycloalkyl, acyl, hydroxy, hydroxyalkyl, haloalkoxy, thioalkyl, heterocyclic, heteroaryl, aryl, amino, aminoalkyl, imino, oxo, thiono, thiol, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$S(O)_n$—$R^{11}$, (n is 0, 1, 2, or 3) —$S(O)_2$—$NH_2$, and —$S(O)_2$—$N(H)R^{11}$; where $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

A further embodiment is directed to a compound of Formula I, wherein Z is H. In certain aspects X and Y are the same or different and are independently selected from the group halo. In certain aspects $R^2$ is independently selected from $R^3$, —$C(O)$—$OR^3$, cyano, —$C(O)$—$OH$, —$C(O)R^3$, —$C(O)$—$N(H)$—$OH$, —$C(O)$—$NH_2$, —$C(NH)$—$N(H)$—$OH$, —$S(O)_2$—$R^3$, $S(O)_2NH_2$, —$C(O)$—$C(O)$—$OR^3$, —$C(O)$—$C(O)$—$OH$, —$C(O)$—$N(H)$—$R^3$, —$C(O)$—$NR^3R^{10}$, —$C(O)$—$N(H)$—$C(O)$—$R^3$, —$C(O)$—$N(H)$—$S(O)_2$—$R^3$, $S(O)_2NH$—$C(O)$—$R^3$, —$S(O)_2NR^3R^{10}$, heteroaryl, heteroaralkyl, heteroaroyl, heterocycle, C(O)-heterocycle, and heterocyclicalkyl. In certain aspects $R^3$ is independently selected from the group consisting of $C_1$-$C_8$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, amino, aminoalkyl, —$NR^{11}R^{12}$, imino, oxo, cyano, carboxy, carboxyalkyl, alkoxycarbonyl, —$OR^6$, —$SR^6$, —$C(O)R^6$, —$C(O)$—$NH_2$, —$C(O)$—$N(H)R^{11}$, —$C(O)$—$NR^{11}R^{12}$, —$S(O)_n$—$R^6$ (n is 0, 1, or 2) —$S(O)_2$—$NH_2$, —$S(O)_2$—$N(H)R^{11}$ and —$S(O)_2$—$NR^{11}R^{12}$. In certain aspects $R^6$ is independently selected from the group consisting of hydrogen, $C_1$-$C_6$ straight alkyl, $C_1$-$C_6$ branched alkyl, $C_1$-$C_6$ cyclic alkyl, aryl, heteroaryl, heterocycle, and acyl, wherein all may be substituted by one or more independently selected from the group consisting of halo, alkyl, lower alkyl, alkenyl, cycloalkyl, acyl, hydroxy, hydroxyalkyl, heterocyclic, heteroaryl, aryl, amino, aminoalkyl, —$NR^{11}R^{12}$, oxo, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$C(O)$—$NR^{11}R^{12}$, —$S(O)_n$—$R^{11}$ (n is 0, 1, or 2), —$S(O)_2$—$NH_2$, —$S(O)_2$—$N(H)R^{11}$ and —$S(O)_2$—$NR^{11}R^{12}$. In certain aspects $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

In a further aspect $NR^{11}R^{12}$ taken together optionally form a 4- to 12-membered saturated or unsaturated heterocyclic or carbocyclic ring, wherein all may be substituted by one or more independently selected from the group consisting of halo, alkyl, lower alkyl, alkenyl, alkynyl, cycloalkyl, acyl, hydroxy, hydroxyalkyl, haloalkoxy, thioalkyl, heterocyclic, heteroaryl, aryl, amino, aminoalkyl, oxo, thiono, thiol, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$S(O)_n$—$R^{11}$ (n is 0, 1, or 2), —$S(O)_2$—$NH_2$, and —$S(O)_2$—$N(H)R^{11}$; where $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, alkoxy, hydroxy, hydroxyalkyl, heterocyclic, heteroaryl, aryl, amino, aminoalkyl, and carboxy.

Certain embodiments are directed to a compound of Formula I where Z is H. In certain aspects X and Y are the same or different and are independently selected from the group halo. In certain aspects $R^2$ is independently selected from the group consisting of —$C(O)$—$OR^3$, cyano, —$C(O)$—$OH$, —$C(O)R^3$, —$C(O)$—$N(H)$—$OH$, —$C(NH)$—$N(H)$—$OH$, —$S(O)_2$—$R^3$, $S(O)_2NH_2$, —$C(O)$—$C(O)$—$OR^3$, —$C(O)$—$C(O)$—$OH$, heteroaryl, heteroaralkyl, heteroaroyl, heterocycle, C(O)-heterocycle, and heterocyclicalkyl; where $R^3$ is independently selected from the group consisting of $C_1$-$C_5$ straight alkyl, and $C_3$-$C_5$ branched alkyl, wherein all may be optionally substituted by one or more independently selected from the group consisting of halo, acyl, hydroxy, alkoxy, haloalkoxy, thioalkyl, hydroxyalkyl, heterocyclic, heteroaryl, aryl, amino, aminoalkyl, alkylamino, dialkylamino, imino, oxo, cyano, carboxy, carboxyalkyl, and alkoxycarbonyl.

Certain embodiments are directed to a compound of Formula I where Z is H. In certain aspects X and Y are the same and are selected from the group halo. In certain aspects $R^2$ is independently selected from the group consisting of —$C(O)$—$OR^3$ and cyano; where $R^3$ is independently selected from the group consisting of $C_1$-$C_5$ straight alkyl.

A further embodiment is directed to a compound of Formula I where Z is H. in certain aspects X and Y are the same and are selected from the group consisting of bromo and chloro. In a further aspect $R^2$ is independently selected from the group consisting of —$C(O)$—$OR^3$ and cyano; where $R^3$ is independently selected from the group consisting of methyl, ethyl and n-propyl.

Certain embodiments are directed to compounds including 3,5-Dihalo-4-[2,3,4 -Trimethoxyphenyl)pyrrole-2-carboxylic acids and carboxylic acid esters; 2-Substituted 3,5 -Dihalo-4-[2,3,4-Trimethoxyphenyl)pyrroles (e.g., 2-Cyano-3,5-Dihalo-4-[2,3,4-Trimethoxy-phenyl)-pyrroles); N-Substituted 3,5-Dihalo-4-[2,3,4-Trimethoxyphenyl)pyrrole-2-carboxylic acid esters; and N-Substituted 2-Cyano-3,5-Dihalo-4-[2,3,4-Trimethoxy-phenyl)-pyrroles. Further aspects are directed to 3,5-Dibromo-4-(2,3,4-trimethoxyphenyl)-1H-pyrrole-2 -carboxylic acid ethyl ester (NT-7-16) or 3,5-Dichloro-4-(2,3,4-trimethoxyphenyl)-1H-pyrrole-2-carboxylic acid ethyl ester.

Certain embodiments are directed to compounds of Formula II or its pharmaceutically acceptable salt, solvate or hydrate.

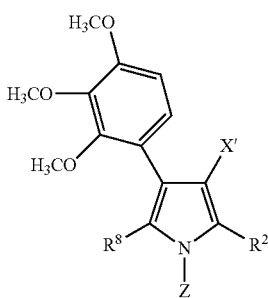

Formula II

Certain embodiment are directed to a compound of Formula II where Z is selected from the group consisting of $R^1$, —OH, —$OR^1$, —$NH_2$, —N(H)—$R^1$, —$NR^1R^{10}$, —C(O)—$R^1$, —C(O)—$OR^1$, —C(O)—C(O)—$OR^1$, —C(O)—C(O)—$NR^1R^{10}$, —C(O)—$NH_2$, —C(O)—N(H)—$R^1$, —C(O)—$NR^1R^{10}$, —C(O)—N(H)—C(O)—$R^1$, —C(O)—N(H)—$S(O)_2$—$R^1$, —$S(O)_2$—$R^1$, —$S(O)_2NR^1R^{10}$, and —C(O)—H.

In certain aspects $R^1$ and $R^{10}$ are the same or different and are independently selected from the group consisting of hydrogen, $C_1$-$C_8$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, amino, aminoalkyl, —$NR^{11}R^{12}$, oxo, imino, cyano, carboxy, carboxyalkyl, alkoxycarbonyl, —$OR^5$, —$SR^5$, —$C(O)R^5$, —C(O)—$NH_2$, —C(O)—$N(H)R^{11}$, —C(O)—$NR^{11}R^{12}$, —$OPO_3H_2$, —$PO_4H_2$, —$PO_3H_2$, —$P(R^5)O_2H$, —$OSO_3H$, —$SO_3H$, —$S(O)_n$—$R^5$ (n is 0, 1, or 2) —$S(O)_2$—$NH_2$, —$S(O)_2$—$N(H)R^{11}$ and —$S(O)_2$—$NR^{11}R^{12}$.

In certain aspects $R^2$ is independently selected from $R^3$, —C(O)—$OR^3$, cyano, —C(O)—OH, —$C(O)R^3$, —C(O)—N(H)—OH, —C(O)—$NH_2$, —C(NH)—N(H)—OH, —$S(O)_2$—$R^3$, $S(O)_2NH_2$, —C(O)—C(O)—$OR^3$, —C(O)—C(O)—OH, —C(O)—N(H)—$R^3$, —C(O)—$NR^3R^{10}$, —C(O)—N(H)—C(O)—$R^3$, —C(O)—N(H)—$S(O)_2$—$R^3$, $S(O)_2NH$—C(O)—$R^3$, —$S(O)_2NR^3R^{10}$, heteroaryl, heteroaralkyl, heteroaroyl, heterocycle, C(O)-heterocycle, and heterocyclicalkyl.

In certain aspects $R^3$ is independently selected from the group consisting of $C_1$-$C_6$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^6$, —$SR^6$, —$C(O)R^6$, —C(O)—$NH_2$, —C(O)—$N(H)R^{11}$, —C(O)—$NR^{11}R^{12}$, —$S(O)_n$—$R^6$ (n is 0, 1, or 2), —$S(O)_2$—$NH_2$, —$S(O)_2$—$N(H)R^{11}$ and —$S(O)_2$—$NR^{11}R^{12}$.

In certain aspects $R^8$ is independently selected from the group consisting of —$C(O)R^{13}$, —C(O)H, $HC(NOR^7)$, $HC(NO(CO)R^7)$, —C(O)—NHOH—, —$C(NR^7)$—NHOH, —$C(NR^7)$—$NH_2$, $C_1$-$C_8$ straight alkyl, $C_3$-$C_8$ branched alkyl, $C_3$-$C_8$ cyclic alkyl, alkenyl, alkynyl, carboxy, cyano, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aroyl, aralkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, lower alkyl, cycloalkyl, alkenyl, alkynyl, acyl, alkanoyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —C(O)—$NH_2$, —C(O)—$NHOR^7$, —$C(NR^7)$—NHOH, —$C(NR^7)$—$NH_2$, C(O)—$N(H)R^{11}$, —C(O)—$NR^{11}R^{12}$, —$NHC(O)R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2), —$S(O)_2$—$NH_2$, —$S(O)_2$—$N(H)R^{11}$ and —$S(O)_2$—$NR^{11}R^{12}$.

In certain aspects $R^5$, $R^6$ and $R^7$ are the same or different and are independently selected from the group consisting of hydrogen, $C_1$-$C_6$ straight alkyl, $C_3$-$C_6$ branched alkyl, $C_3$-$C_6$ cyclic alkyl, aryl, heteroaryl, heterocycle, and acyl, wherein all may be substituted by one or more independently selected from the group consisting of halo, alkyl, lower alkyl, alkenyl, cycloalkyl, acyl, hydroxy, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^{11}$, —$C(O)R^{11}$, —C(O)—$NH_2$, —C(O)—$N(H)R^{11}$, —C(O)—$NR^{11}R^{12}$, —$S(O)_n$—$R^{11}$ (n is 0, 1, or 2), —$S(O)_2$—$NH_2$, —$S(O)_2$—$N(H)R^{11}$ and —$S(O)_2$—$NR^{11}R^{12}$.

In certain aspects $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, oxo, alkoxy, hydroxy, hydroxyalkyl, heterocyclic, heteroaryl, aryl, imino, amino, aminoalkyl, and carboxy.

In certain aspects X' is independently selected from the group consisting of halo, cyano, —C(O)—$OR^7$, $HC(NOR^7)$, —C(NH)—N(H)—$OR^7$, —$C(NR^7)$—$NH_2$, $R^{14}$, —C(O)—$R^{15}$, —$C(NR^7)$—$NHOR^7$, —$C(NR^7)$—$NHR^7$, C(O)—$N(H)R^{11}$, —C(O)—$NR^{11}R^{12}$, and —C(O)—H.

In certain aspects $R^{13}$ is independently selected from the group consisting $C_1$-$C_8$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —C(O)—$NH_2$, —C(O)—$NHOR^7$, —$C(NR^7)$—NHOH, —$C(NR^7)$—$NH_2$, C(O)—$N(H)R^{11}$, —C(O)—$NR^{11}R^{12}$, —NHC(O) $R^7$, —$OPO_3H_2$, —$PO_4H_2$, —$PO_3H_2$, —$P(R^7)$ $O_2H$, —$OSO_3H$, —$SO_3H$, —$S(O)_n$—$R^7$, —$S(O)_2$—$NH_2$, —$S(O)_2$—$N(H)R^{11}$ and —$S(O)_2$—$NR^{11}R^{12}$.

In certain aspects $R^{14}$ is independently selected from the group consisting of $C_1$-$C_6$ straight alkyl, $C_3$-$C_6$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, haloalkoxy, thioalkyl, hydroxyalkyl, heterocyclic, heteroaryl, aryl, amino, aminoalkyl, -alkylamino, imino, oxo, cyano, carboxy, carboxyalkyl, alkoxycarbonyl, —$OR^7$, —$SR^7$, —$C(O)R^7$, —$C(O)$—$NH_2$, —$C(O)$—$NHOR^7$, —$C(NR^7)$—$NHOH$, —$C(NR^7)$—$NH_2$, $C(O)$—$N(H)R^{11}$, —$C(O)$—$NR^{11}R^{12}$, —$NHC(O)$ $R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2), —$S(O)_2$—$NH_2$, —$S(O)_2$—$N(H)R^{11}$ and —$S(O)_2$—$NR^{11}R^{12}$.

In certain aspects $R^{15}$ is independently selected from the group consisting of $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, heterocyclic, amino, aminoalkyl, alkylamino, imino, oxo, cyano, carboxy, carboxyalkyl, and alkoxycarbonyl.

In certain aspects Z and $R^2$ taken together or Z and $R^8$ taken together optionally form a 4- to 12-membered saturated or unsaturated heterocyclic or carbocyclic ring, wherein all may be substituted by one or more independently selected from the group consisting of halo, alkyl, lower alkyl, alkenyl, alkynyl, cycloalkyl, acyl, hydroxy, hydroxyalkyl, haloalkoxy, thioalkyl, heterocyclic, heteroaryl, aryl, amino, aminoalkyl, —$NR^{11}R^{12}$, imino, oxo, thiono, thiol, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$C(O)$—$NR^{11}R^{12}$, —$S(O)_n$—$R^{11}$ (n is 0, 1, or 2), —$S(O)_2$—$NH_2$, —$S(O)_2$—$N(H)R^{11}$ and —$S(O)_2$—$NR^{11}R^{12}$.

In certain aspects $NR^{11}R^{12}$ taken together optionally form a 4- to 12-membered saturated or unsaturated heterocyclic or carbocyclic ring, wherein all may be substituted by one or more independently selected from the group consisting of halo, alkyl, lower alkyl, alkenyl, alkynyl, cycloalkyl, acyl, hydroxy, hydroxyalkyl, haloalkoxy, thioalkyl, heterocyclic, heteroaryl, aryl, amino, aminoalkyl, imino, oxo, thiono, thiol, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$S(O)_n$—$R^{11}$ (0, 1, or 2), —$S(O)_2$—$NH_2$, and —$S(O)_2$—$N(H)R^{11}$.

In certain aspects Z, $R^2$, X', and $R^8$ must be different.

Other embodiments are directed to a compound of Formula II or its pharmaceutically acceptable salt, solvate or hydrate, wherein Z is H.

In certain aspects $R^2$ is independently selected from —$C(O)$—$OR^3$, cyano, —$C(O)$—$OH$, —$C(O)R^3$, —$C(O)$—$N(H)$—$OH$, —$C(O)$—$NH_2$, —$C(NH)$—$N(H)$—$OH$, —$S(O)_2$—$R^3$, $S(O)_2NH_2$, —$S(O)_2NH$—$C(O)$—$OR^3$, —$C(O)$—$C(O)$—$OH$, —$C(O)$—$N(H)$—$R^3$, —$C(O)$—$NR^3R^{10}$, —$C(O)$—$N(H)$—$C(O)$—$R^3$, —$C(O)$—$N(H)$—$S(O)_2$—$R^3$, $S(O)_2NH$—$C(O)$—$R^3$, —$S(O)_2NR^3R^{10}$, heteroaryl, heteroaralkyl, heteroaroyl, heterocycle, C(O)-heterocycle, and heterocyclicalkyl.

In certain aspects $R^3$ is independently selected from the group consisting of $C_1$-$C_6$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, alkyl, lower alkyl, alkenyl, alkynyl, cycloalkyl, acyl, hydroxy, alkoxy, haloalkoxy, thioalkyl, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^6$, —$SR^6$, —$C(O)R^6$, —$C(O)$—$NH_2$, —$C(O)$—$N(H)R^{11}$, —$C(O)$—$NR^{11}R^{12}$, —$S(O)_n$—$R^6$ (n is 0, 1, or 2), —$S(O)_2$—$NH_2$, —$S(O)_2$—$N(H)R^{11}$ and —$S(O)_2$—$NR^{11}R^{12}$.

In certain aspects $R^8$ is independently selected from the group consisting of —$C(O)R^{13}$, —$HC(NOR^7)$, $HC(NO(CO)R^7)$, —$C(O)$—$NHOH$—, —$C(NR^7)$—$NHOH$, —$C(NR^7)$—$NH_2$, $C_1$-$C_8$ straight alkyl, $C_3$-$C_8$ branched alkyl, $C_3$-$C_8$ cyclic alkyl, alkenyl, alkynyl, carboxy, cyano, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aroyl, aralkyl, heteroaryl, heteroaroyl, heteroaralkyl, heterocycle, —(CO)heterocycle and heterocyclicalkyl, wherein all may be optionally substituted by one or more substituent independently selected from the group consisting of halo, alkyl, lower alkyl, cycloalkyl, alkenyl, alkynyl, acyl, alkanoyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —$C(O)$—$NH_2$, —$C(O)$—$NHOR^7$, —$C(NR^7)$—$NHOH$, —$C(NR^7)$—$NH_2$, $C(O)$—$N(H)R^{11}$, —$C(O)$—$NR^{11}R^{12}$, —$NHC(O)R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2) —$S(O)_2$—$NH_2$, —$S(O)_2$—$N(H)R^{11}$ and —$S(O)_2$—$NR^{11}R^{12}$.

In certain aspects $R^6$ and $R^7$ are the same or different and are independently selected from the group consisting of hydrogen, $C_1$-$C_6$ straight alkyl, $C_3$-$C_6$ branched alkyl, $C_3$-$C_6$ cyclic alkyl, aryl, heteroaryl, heterocycle, and acyl, wherein all may be substituted by one or more independently selected from the group consisting of halo, alkyl, lower alkyl, alkenyl, cycloalkyl, acyl, hydroxy, hydroxyalkyl, heterocyclic, heteroaryl, aryl, imino, amino, aminoalkyl, —$NR^{11}R^{12}$, oxo, cyano, carboxy, carboxyalkyl, alkoxycarbonyl, —$OR^{11}$, —$C(O)R^{11}$, —$C(O)$—$NH_2$, —$C(O)$—$N(H)R^{11}$, —$C(O)$—$NR^{11}R^{12}$, —$S(O)_nR^{11}$ (n is 0, 1, or 2) —$S(O)_2$—$NH_2$, —$S(O)_2$—$N(H)R^{11}$ and —$S(O)_2$—$NR^{11}R^{12}$.

In certain aspects $R^{11}$ and $R^{12}$ are independently selected from the group consisting of alkyl, alkenyl, heterocyclic, heteroaryl and aryl, wherein all may be substituted by one or more independently selected from the group consisting of halo, alkyl, lower alkyl, acyl, oxo, alkoxy, hydroxy, hydroxyalkyl, heterocyclic, heteroaryl, aryl, imino, amino, aminoalkyl, and carboxy.

In certain aspects X' is independently selected from the group consisting of halo, cyano, —$C(O)$—$OR^7$, $HC(NOR^7)$, —$C(NH)$—$N(H)$—$OR^7$, —$C(NR^7)$—$NH_2$, $R^{14}$, —$C(O)$—$R^{15}$, —$C(NR^7)$—$NHOR^7$, —$C(NR^7)$—$NHR^7$, $C(O)$—$N(H)R^{11}$, —$C(O)$—$NR^{11}R^{12}$, and —$C(O)$—$H$.

In certain aspects $R^{13}$ is independently selected from the group consisting $C_1$-$C_8$ straight alkyl, $C_3$-$C_8$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —C(O)—$NH_2$, —C(O)—$NHOR^7$, —$C(NR^7)$—NHOH, —$C(NR^7)$—$NH_2$, C(O)—$N(H)R^{11}$—C(O)—$NR^{11}R^{12}$, —$NHC(O)R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2) —$S(O)_2$—$NH_2$, —$S(O)_2$—$N(H)R^{11}$ and —$S(O)_2$—$NR^{11}R^{12}$.

In certain aspects $R^{14}$ is independently selected from the group consisting of $C_1$-$C_6$ straight alkyl, $C_3$-$C_6$ branched alkyl, $C_3$-$C_8$ cyclic alkyl, alkenyl, alkynyl, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aralkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —C(O)—$NH_2$, —C(O)—$NHOR^7$, —$C(NR^7)$—NHOH, —$C(NR^7)$—$NH_2$, C(O)—$N(H)R^{11}$, —C(O)—$NR^{11}R^{12}$, —$NHC(O)R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2) —$S(O)_2$—$NH_2$, —$S(O)_2$—$N(H)R^{11}$ and —$S(O)_2$—$NR^{11}R^{12}$.

In certain aspects $R^{15}$ is independently selected from the group consisting of $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, heterocyclic, amino, aminoalkyl, alkylamino, imino, oxo, cyano, carboxy, carboxyalkyl, and alkoxycarbonyl.

In certain aspects Z, $R^2$, X', and $R^8$ must be different.

Certain embodiments are directed to a compound of Formula II or its pharmaceutically acceptable salt, solvate or hydrate, wherein Z is H.

In certain aspects $R^2$ is independently selected from —C(O)—$OR^3$, cyano, —C(O)—OH, —$C(O)R^3$, —C(O)—N(H)—OH, —C(O)—$NH_2$, —C(NH)—N(H)—OH, —$S(O)_2$—$R^3$, $S(O)_2NH_2$, —C(O)—C(O)—$OR^3$, —C(O)—C(O)—OH, —C(O)—N(H)—$R^3$, —C(O)—$NR^3R^{10}$, —C(O)—N(H)—C(O)—$R^3$, —C(O)—N(H)—$S(O)_2$—$R^3$, $S(O)_2NH$—C(O)—$R^3$, —$S(O)_2NR^3R^{10}$, heteroaryl, heteroaralkyl, heteroaroyl, heterocycle, C(O)-heterocycle, and heterocyclicalkyl.

In certain aspects $R^3$ is independently selected from the group consisting of $C_1$-$C_5$ straight alkyl, and $C_3$-$C_5$ branched alkyl, wherein all may be optionally substituted by one or more independently selected from the group consisting of halo, acyl, hydroxy, alkoxy, hydroxyalkyl, amino, aminoalkyl, alkylamino, dialkylamino, imino, oxo, cyano, carboxy, carboxyalkyl, and alkoxycarbonyl.

In certain aspects $R^8$ is independently selected from the group consisting of —$C(O)R^{13}$, —HC(NOR^7), HC(NO(CO)$R^7$), —C(O)—NHOH—, —$C(NR^7)$—NHOH, —$C(NR^7)$—$NH_2$, $C_1$-$C_5$ straight alkyl, $C_3$-$C_5$ branched alkyl, $C_3$-$C_5$ cyclic alkyl, alkenyl, alkynyl, carboxy, cyano, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aroyl, aralkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, lower alkyl, acyl, alkanoyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —$C(O)R^7$, —C(O)—$NH_2$, —C(O)—$NHOR^7$, —$C(NR^7)$—NHOH, —$C(NR^7)$—$NH_2$, C(O)—N(H)$R^{11}$, —C(O)—$NR^{11}R^{12}$, —$NHC(O)R^7$, —$OPO_3H_2$, —$PO_4H_2$, —$PO_3H_2$, —$P(R^7)O_2H$, —$OSO_3H$, —$SO_3H$, —$S(O)_n$—$R^7$ (n is 0, 1, or 2), —$S(O)_2$—$NH_2$, —$S(O)_2$—$N(H)R^{11}$ and —$S(O)_2$—$NR^{11}R^{12}$; where $R^7$, $R^{11}$ and $R^{12}$ are independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

In certain aspects X' is independently selected from the group consisting of —$R^{14}$ and —C(O)—$R^{15}$.

In certain aspects $R^{13}$ is independently selected from the group consisting $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, acyloxyalkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, hydroxyalkyl, heterocyclic, heteroaryl, amino, aminoalkyl, -alkylamino, imino, oxo, cyano, carboxy, carboxyalkyl, and alkoxycarbonyl.

In certain aspects $R^{14}$ is independently selected from the group consisting of $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, heterocyclic, amino, aminoalkyl, alkylamino, imino, oxo, cyano, carboxy, carboxyalkyl, and alkoxycarbonyl.

In certain aspects $R^{15}$ is independently selected from the group consisting of $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, heterocyclic, amino, aminoalkyl, alkylamino, imino, oxo, cyano, carboxy, carboxyalkyl, and alkoxycarbonyl.

In certain aspects Z, $R^2$, X', and $R^8$ must be different.

Other embodiments are directed to compounds of Formula II or pharmaceutically acceptable salt, solvate or hydrate thereof, wherein Z is H.

In certain aspects $R^2$ is independently selected from —C(O)—$OR^3$, cyano, —C(O)—OH, heteroaryl, heteroaralkyl, heteroaroyl, heterocycle, and C(O)-heterocycle.

In certain aspects $R^3$ is independently selected from the group consisting of $C_1$-$C_5$ straight alkyl.

In certain aspects $R^8$ is independently selected from the group consisting of —C(O)$R^{13}$, —HC(NO$R^7$), HC(NO(CO)$R^7$), —C(O)—NHOH—, —C($NR^7$)—NHOH, —C($NR^7$)—$NH_2$, $C_1$-$C_5$ straight alkyl, $C_3$-$C_5$ branched alkyl, $C_3$-$C_5$ cyclic alkyl, alkenyl, alkynyl, carboxy, cyano, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aroyl, aralkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, lower alkyl, acyl, alkanoyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —C(O)$R^7$, —C(O)—$NH_2$, —C(O)—NHO$R^7$, —C($NR^7$)—NHOH, —C($NR^7$)—$NH_2$, C(O)—N(H)$R^{11}$, —C(O)—$NR^{11}R^{12}$, —NHC(O)$R^7$, —$OPO_3H_2$, —$PO_4H_2$, —$PO_3H_2$, —P($R^7$)$O_2H$, —$OSO_3H$, —$SO_3H$, —S(O)$_n$—$R^7$ (n is 0, 1, or 2), —S(O)$_2$—$NH_2$, —S(O)$_2$—N(H)$R^{11}$ and —S(O)$_2$—$NR^{11}R^{12}$; where $R^7$, $R^{11}$ and $R^{12}$ are independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

In certain aspects X' is independently selected from the group consisting of —$R^{14}$ and —C(O)—$R^{15}$.

In certain aspects $R^{13}$ is independently selected from the group consisting $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, acyloxyalkyl, heteroaryl, heteroaralkyl, heterocycle, and heterocyclicalkyl, wherein all may be optionally substituted by one or more independently selected from the group consisting of halo, lower alkyl, cycloalkyl, alkenyl, alkynyl, acyl, hydroxy, alkoxy, hydroxyalkyl, heterocyclic, heteroaryl, amino, aminoalkyl, -alkylamino, imino, oxo, cyano, carboxy, carboxyalkyl, and alkoxycarbonyl.

In certain aspects $R^{14}$ is independently selected from the group consisting of hydroxyalkyl, alkoxyalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, amino, aminoalkyl, alkylamino, imino, oxo, cyano, carboxy, carboxyalkyl, and alkoxycarbonyl.

In certain aspects $R^{15}$ is independently selected from the group consisting of $C_1$-$C_5$ straight alkyl, $C_3$-$C_5$ branched alkyl, $C_3$-$C_5$ cyclic alkyl, alkenyl, and alkynyl, wherein all may be optionally substituted by one or more independently selected from the group consisting of halo, acyl, hydroxy, alkoxy, amino, aminoalkyl, alkylamino, imino, oxo, cyano, carboxy, carboxyalkyl, and alkoxycarbonyl.

In certain aspects Z, $R^2$, X', and $R^8$ must be different.

Certain embodiments are directed to compounds of Formula II or pharmaceutically acceptable salt, solvate or hydrate thereof, wherein Z is H.

In certain aspects $R^2$ is independently selected from —C(O)—$OR^3$, and cyano.

In certain aspects $R^3$ is independently selected from the group consisting of $C_1$-$C_5$ straight alkyl.

In certain aspects $R^8$ is independently selected from the group consisting of HC(NO$R^7$), amidoalkyl, aminoalkyl, and alkylaminoalkyl, wherein all may be optionally substituted by one or more independently selected from the group consisting of acyl, alkanoyl, hydroxy, alkoxy, hydroxyalkyl, heterocyclic, heteroaryl, amino, imino, oxo, cyano, carboxy, carboxyalkyl, alkoxycarbonyl, —$OPO_3H_2$, —$PO_4H_2$, —$PO_3H_2$, —P($R^7$)$O_2H$, —$OSO_3H$, and —$SO_3H$.

In certain aspects X' is independently selected from the group consisting of —$R^{14}$ and —C(O)—$R^{15}$.

In certain aspects $R^{14}$ is independently selected from the group consisting of hydroxyalkyl, alkoxyalkyl, aminoalkyl, alkylaminoalkyl, dialkylaminoalkyl, amidoalkyl, carboxyalkyl, alkoxycarbonylalkyl, and acyloxyalkyl, wherein all may be optionally substituted by one or more independently selected from the group consisting of halo, acyl, hydroxy, alkoxy, amino, aminoalkyl, alkylamino, imino, oxo, cyano, carboxy, carboxyalkyl, and alkoxycarbonyl.

In certain aspects $R^{15}$ is independently selected from the group consisting of $C_1$-$C_5$ straight alkyl, $C_3$-$C_5$ branched alkyl, $C_3$-$C_5$ cyclic alkyl, alkenyl, and alkynyl, wherein all may be optionally substituted by one or more independently selected from the group consisting of halo, acyl, hydroxy, alkoxy, amino, aminoalkyl, alkylamino, imino, oxo, cyano, carboxy, carboxyalkyl, and alkoxycarbonyl.

In certain aspects Z, $R^2$, X', and $R^8$ must be different.

Certain embodiments are directed to compounds of Formula II or pharmaceutically acceptable salt, solvate or hydrate thereof, wherein Z is H.

In certain aspects X' is independently selected from the group halo.

In certain aspects $R^2$ is independently selected from —C(O)—$OR^3$, cyano, —C(O)—OH, heteroaryl, heteroaralkyl, heteroaroyl, heterocycle, and C(O)-heterocycle.

In certain aspects $R^3$ is independently selected from the group consisting of $C_1$-$C_5$ straight alkyl, and $C_3$-$C_5$ branched alkyl, wherein all may be optionally substituted by one or more independently selected from the group consisting of halo, acyl, hydroxy, alkoxy, hydroxyalkyl, aryl, amino, aminoalkyl, alkylamino, dialkylamino, imino, oxo, cyano, carboxy, carboxyalkyl, and alkoxycarbonyl.

In certain aspects $R^8$ is independently selected from the group consisting of —C(O)$R^{13}$, —HC(NO$R^7$), HC(NO(CO)$R^7$), —C(O)—NHOH—, —C($NR^7$)—NHOH, —C($NR^7$)—$NH_2$, $C_1$-$C_5$ straight alkyl, $C_3$-$C_5$ branched alkyl, $C_3$-$C_5$ cyclic alkyl, alkenyl, alkynyl, carboxy, cyano, hydroxyalkyl, alkoxyalkyl, haloalkyl, thioalkyl, alkylthioalkyl, aminoalkyl, alkylaminoalkyl, dialkylaminoalkyl, amidoalkyl, carboxyalkyl, alkoxycarbonylalkyl, acyloxyalkyl, sulfonylalkyl, sulfonamidoalkyl, aryl, aroyl, aralkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, lower alkyl, acyl, alkanoyl, hydroxy, alkoxy, haloalkoxy, thioalkyl, hydroxyalkyl, heterocyclic, heteroaryl, aryl, amino, aminoalkyl, alkylamino, imino, oxo, cyano, carboxy, carboxyalkyl, alkoxycarbonyl, —$OR^7$, —$SR^7$, —C(O)$R^7$, —C(O)—$NH_2$, —C(O)—NHO$R^7$, —C($NR^7$)—NHOH, —C($NR^7$)—$NH_2$, C(O)—N (H)R$^{11}$, —C(O)—NR$^{11}$R$^{12}$, —NHC(O)R$^7$, —OPO$_3$H$_2$, —PO$_4$H$_2$, —PO$_3$H$_2$, —P(R$^7$)O$_2$H, —OSO$_3$H, —SO$_3$H, —S(O)$_n$—R$^7$ (n is 0, 1, or 2), —S(O)$_2$—NH$_2$, —S(O)$_2$—N(H)R$^{11}$ and —S(O)$_2$—NR$^{11}$R$^{12}$.

In certain aspects R$^7$, R$^{11}$ and R$^{12}$ are independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

In certain aspects R$^{13}$ is independently selected from the group consisting C$_1$-C$_8$ straight alkyl, C$_3$-C$_8$ branched alkyl, C$_3$-C$_8$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, acyloxyalkyl, heteroaryl, heteroaralkyl, heterocycle, and heterocyclicalkyl, wherein all may be optionally substituted by one or more independently selected from the group consisting of halo, acyl, hydroxy, alkoxy, hydroxyalkyl, heterocyclic, heteroaryl, amino, aminoalkyl, alkylamino, imino, oxo, cyano, carboxy, carboxyalkyl, and alkoxycarbonyl.

In certain aspects Z, R$^2$, X', and R$^8$ must be different.

Other embodiments are directed to compounds of Formula II or pharmaceutically acceptable salt, solvate or hydrate thereof, wherein Z is H.

In certain aspects X' is independently selected from the group halo.

In certain aspects R$^2$ is independently selected from the group consisting of —C(O)—OR$^3$ and cyano.

In certain aspects R$^3$ is independently selected from the group consisting of C$_1$-C$_5$ straight alkyl.

In certain aspects R$^8$ is independently selected from the group consisting of HC(NOR$^7$), C$_1$-C$_5$ straight alkyl, C$_3$-C$_5$ branched alkyl, C$_3$-C$_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, acyloxyalkyl, sulfonylalkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, acyl, alkanoyl, hydroxy, alkoxy, hydroxyalkyl, heterocyclic, heteroaryl, amino, aminoalkyl, alkylamino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, and —SO$_3$H.

In certain aspects R$^7$ is independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

Certain embodiments are directed to compounds of Formula II or pharmaceutically acceptable salt, solvate or hydrate thereof, wherein Z is H.

In certain aspects R$^2$ is independently selected from the group consisting of —C(O)—OR$^3$ and cyano.

In certain aspects R$^3$ is independently selected from the group consisting of C$_1$-C$_5$ straight alkyl.

In certain aspects X' is independently selected from the group halo.

In certain aspects R$^8$ is independently selected from the group consisting of HC(NOR$^7$), amidoalkyl, aminoalkyl, and alkylaminoalkyl, wherein all may be optionally substituted by one or more independently selected from the group consisting of acyl, alkanoyl, hydroxy, alkoxy, hydroxyalkyl, heterocyclic, heteroaryl, amino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, and —SO$_3$H.

In certain aspects R$^7$ is independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

In certain aspects Certain embodiments are directed to compounds of Formula II or pharmaceutically acceptable salt, solvate or hydrate thereof, wherein Z is H.

In certain aspects X' is bromo or chloro.

In certain aspects R$^2$ is independently selected from the group consisting of —C(O)—OR$^3$ and cyano.

In certain aspects R$^3$ is independently selected from the group consisting of methyl, ethyl and n-propyl.

In certain aspects R$^8$ is independently selected from the group consisting of oximino, O-methyl-oximino, O-ethyl-oximino, O-n-propyl-oximino, aminomethyl, aminoethyl, aminopropyl, aminobutyl, and methylaminomethyl, ethylaminomethyl, propylaminomethyl, butylaminommethyl, methylamino ethyl, ethylamino ethyl, propylamino ethyl, butylamino ethyl, methylaminopropyl, ethylaminopropyl, propylaminopropyl, butylaminopropyl, methylaminobutyl, ethylaminobutyl, propylaminobutyl and butylaminobutyl, wherein all may be optionally substituted by one or more independently selected from the group consisting of acyl, alkanoyl, hydroxy, alkoxy, hydroxyalkyl, heterocyclic, heteroaryl, amino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, and —SO$_3$H.

In certain aspects R$^7$ is independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

In certain aspects the compounds are pharmaceutically acceptable salts, prodrugs, solvates, or hydrates of Formula I or Formula II.

Certain aspects include pharmaceutical compositions comprising a therapeutically effective amount of a compound of Formula I or Formula II and a pharmaceutically acceptable carrier in a form suitable for oral, parenteral, intravenous, intradermal, transdermal, subcutaneous or topical administration.

Certain embodiments are directed to methods for inhibiting the proliferation of and/or causing cytotoxicity to one or more cancerous cells comprising contacting one or more live cancerous cells with a compound of Formula I or Formula II, as described herein, or a pharmaceutically acceptable salt, prodrug, solvate or hydrate of the compound of Formula I or Formula II.

Other embodiments are directed to methods of treating a patient having cancer comprising administering to the patient a therapeutically effective amount of a compound of Formula I or Formula II, as described herein, or a pharmaceutical acceptable salt, prodrug, solvate, or hydrate of the compound of Formula I or Formula II.

In some embodiments, the compound is a salt. Such salts may be anhydrous or associated with water as a hydrate. In some embodiments, the compound is a prodrug.

In certain embodiments, the compounds described herein may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan. Certain compounds of the invention may possess asymmetric carbon atoms (optical centers) or double bonds. The racemates, enantiomers, diastereomers, geometric isomers and individual isomers are all intended to be encompassed within the scope of the invention.

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula. Compounds of the present disclosure include, but are not limited to, compounds of Formula I or Formula II and all pharmaceutically acceptable forms thereof.

Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts.

I. Definitions

As used herein, the term "therapeutically effective amount" refers to that amount of a compound described herein that brings about a desired effect in a patient. The desired effect will vary depending on the illness being treated. For example, the desired effect may be reducing tumor size, destroying cancerous cells, preventing tumor growth, preventing metastasis and/or preventing angiogenesis, any one of which may be the desired therapeutic response. On its most basic level, a therapeutically effective amount is that amount needed to inhibit the proliferation of a cancerous cell. Any amount of inhibition of proliferation will yield a benefit to a patient and is therefore within the scope of the invention.

As used herein, the term "patient" refers to warm-blooded animals or mammals, and in particular humans, who are in need of the therapy described herein.

The term "host", as used herein, refers to a unicellular or multicellular organism, including cell lines and animals, and preferably a human.

As used herein, the term "having cancer" means that the patient has been diagnosed with cancer.

The term "prodrug(s)" includes any compounds that become compounds of Formula I when administered to a patient, e.g., upon metabolic processing of the prodrug. Examples of prodrugs include, but are not limited to acetate, formate, benzoate, carbomethoxy, carboethoxy and like derivatives of functional groups (such as alcohol, carboxylic acid, ether, ester, or amine groups) in the compounds of Formula I or Formula II.

The term "Pharmaceutically acceptable" refers to those items generally recognized for use in animals, and more particularly in humans. The term "Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

The terms "Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

The terms "alkyl" or "alk", alone or in combination, unless otherwise specified, refers to a saturated straight or branched primary, secondary, or tertiary hydrocarbon from 1 to 8 carbon atoms, including, but not limited to methyl, ethyl, propyl, isopropyl, butyl, isobutyl, t-butyl, and sec-butyl. The term "lower alkyl" alone or in combination refers to an alkyl having from 1 to 4 carbon atoms. The alkyl group may be optionally substituted with any moiety that does not otherwise interfere with the reaction or that provides an improvement in the process or physical properties, including but not limited halo, haloalkyl, hydroxyl, carboxyl, acyl, aryl, acyloxy, oxo, imino, amino, amido, carboxyl derivatives, alkylamino, dialkylamino, arylamino, aminoalkyl, alkoxy, aryloxy, cyano, thiol, imino, oxo, sulfonyl, sulfanyl, sulfinyl, sulfamonyl, ester, carboxylic acid, amide, thioether, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CF_2H$.

The term "alkenyl", alone or in combination, means a non-cyclic alkyl of 2 to 10 carbon atoms having one or more unsaturated carbon-carbon bonds. The alkenyl group may be optionally substituted with any moiety that does not otherwise interfere with the reaction or that provides an improvement in the process or the physical properties, including but not limited to but limited to halo, haloalkyl, hydroxyl, carboxyl, acyl, aryl, acyloxy, oxo, imino, amino, amido, carboxyl derivatives, alkylamino, dialkylamino, arylamino, aminoalkyl, alkoxy, aryloxy, cyano, thiol, imino, oxo, sulfonyl, sulfanyl, sulfinyl, sulfamonyl, ester, carboxylic acid, amide, thioether, either unprotected, or protected as necessary, as known to those skilled in the art, for example, as taught in Greene et al., *Protective Groups in Organic Synthesis*, John Wiley & Sons, Second Edition, 1991, hereby incorporated by reference.

The term "alkynyl", alone or in combination, means a non-cyclic alkyl of 2 to 10 carbon atoms having one or more triple carbon-carbon bonds, including but not limited to ethynyl and propynyl. The alkynyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, oxo, imino, amino, amido, carboxyl derivatives, alkylamino, dialkylamino, arylamino, aminoalkyl, alkoxy, aryloxy, cyano, thiol, imino, oxo, sulfonyl, sulfanyl, sulfinyl, sulfamonyl, ester, carboxylic acid, amide, thioether, either unprotected, or protected as necessary, as known to those skilled in the art, for example, as taught in Greene et al., *Protective Groups in Organic Synthesis*, John Wiley & Sons, Second Edition, 1991, hereby incorporated by reference.

The terms "carboxy", "carboxyl", "COOH" and "C(O)OH" are used interchangeably.

The terms "alkoxycarbonyl" and "carboalkoxy" are used interchangeably. Used alone or in combination, the terms refer to the radical —C(O)OR, wherein R is alkyl or lower alkyl as defined herein.

The term "thio", alone or in combination, means the radical —S—.

The term "thiol", alone or in combination, means the radical —SH.

The term "thiono" refers to a sulfur atom attached by a double bond (=S).

The term "hydroxy", alone or in combination means the radical —OH.

The term "sulfonyl", alone or in combination means the radical —S(O)2-.

The term "oxo" refers to an oxygen atom attached by a double bond (=O).

The term "imino" refers to a nitrogen attached by a double bond (=N).

The term "oximino" refers to a nitrogen atom attached by a double bond and also bound to oxygen (=N—O).

The terms "carbocycle" and "carbocyclic", alone or in combination, means any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The term "cycloalkyl", alone or in combination, means a saturated or partially unsaturated cyclic alkyl, having from 3 to 10 carbon atoms, including but not limited to mono- or bi-cyclic ring systems such as cyclopropyl, cyclobutyl, cyclopentyl, cyclohexenyl, and cyclohexyl.

The term "aryl", alone or in combination, means a carbocyclic aromatic system containing one, two or three rings wherein such rings may be attached together in a pendent manner or may be fused. The "aryl" group can be optionally substituted with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthio, haloalkoxy, haloalkyl, hydroxyl, carboxyl, acyl, oxo, imino, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis," John Wiley and Sons, Second Edition, 1999. In addition, adjacent groups on an "aryl" ring may combine to form a 5- to 7-membered saturated or partially unsaturated carbocyclic, aryl, heteroaryl or heterocyclic ring, which in turn may be substituted as above.

The term "heterocyclic" or "heterocycle", alone or in combination, refers to a nonaromatic cyclic group that may be partially (containing at least one double bond) or fully saturated and wherein the ring contains at least one heteroatom selected from oxygen, sulfur, nitrogen, or phosphorus.

The terms "heteroaryl" or "heteroaromatic", alone or in combination, refer to an aromatic ring containing at least one heteroatom selected from sulfur, oxygen, nitrogen or phosphorus. The heteroaryl or heterocyclic ring may optionally be substituted by one or more substituents listed as optional substituents for aryl. In addition, adjacent groups on the heteroaryl or heterocyclic ring may combine to form a 5- to 7-membered carbocyclic, aryl, heteroaryl or heterocyclic ring, which in turn may be substituted as above. Nonlimiting examples of heterocylics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isoxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "aroyl", alone or in combination, refers to an aryl group bound to the molecule through a carbonyl, —C(O)— group.

The term "aryloxy", alone or in combination, refers to an aryl group bound to the molecule through an oxygen atom.

The term "heteroaroyl", alone or in combination, refers to a heteroaryl group bound to the molecule through a carbonyl, —C(O)— group.

The term "heteroaryloxy", alone or in combination, refers to a heteroaryl group bound to the molecule through an oxygen atom.

The term "aralkoxy", alone or in combination, refers to an aryl group attached to an alkyl group, which is attached to the molecule through an oxygen atom.

The term "heterocyclearalkoxy" refers to a heterocyclic group attached to an aryl group attached to an alkyl-O— group. The heterocyclic, aryl and alkyl groups can be optionally substituted as described above.

The terms "halo" and "halogen", alone or in combination, refer to chloro, bromo, iodo and fluoro.

The terms "alkoxy" or "alkylthio", alone or in combination, refers to an alkyl group, as defined above, bonded through an oxygen linkage (—O—) or a sulfur linkage (—S—), respectively. The terms "lower alkoxy" or "lower alkylthio", alone or in combination, refers to a lower alkyl group as defined above bonded through an oxygen linkage (—O—) or a sulfur linkage (—S—), respectively.

The term "acyl", alone or in combination, refers to a group of the formula C(O)R', wherein R' is an alkyl, aryl, alkaryl or aralkyl group, or optionally substituted alkyl, aryl, aralkyl or alkaryl, wherein these groups are as defined above.

The term "alkanoyl", alone or in combination, refers to a group of the formula C(O)R', wherein R' is an alkyl or optionally substituted alkyl group, wherein these groups are as defined above.

The term "amidoalkyl", alone or in combination, refers to a group of the formula —NHC(O)R', wherein R' is an alkyl group or optionally substituted alkyl group, wherein these groups are as defined above, and includes related (—NHC(O)OR') carbamate and (—NHC(O)NHR') urea derivatives.

The term "acetyl", alone or in combination, refers to the radical —C(O)CH$_3$.

The term "amino", alone or in combination, denotes the radical —NH$_2$ or —NH—.

The term "nitro", alone or in combination, denotes the radical —NO$_2$.

The term "substituted", means that one or more hydrogen on the designated atom or substituent is replaced with a selection from the indicated group, provided that the designated atom's normal valency is not exceeded, and the that the substitution results in a stable compound. When a substituent is "oxo" (keto) (i.e., =O) or "imino" (i.e., =NH or =NR) then 2 hydrogens on the atom are replaced.

II. Pharmaceutical Compositions

Certain embodiments are directed to pharmaceutical compositions of one or more polysubstituted 4-[(2,3,4-trimethoxy)phenyl]-pyrrole compounds of Formula I or Formula II that include at least one pharmaceutically acceptable carrier, excipient or diluent and a therapeutically effective amount of the compound of any of the embodiments described herein. In some such embodiments, the compound is present in an amount effective for the treatment of cancer.

Further provided are pharmaceutical formulations of one or more polysubstituted 4-[(2,3,4-trimethoxy)phenyl]-pyrrole compounds of Formula I or Formula II that include at least one pharmaceutically acceptable carrier, and a therapeutically effective amount of the composition of matter of any of the embodiments described herein in combination with at least one additional compound such as a cytotoxic agent.

The pharmaceutical compositions or formulations for the administration of the compounds described herein may conveniently be presented in unit dosage form and may be prepared by any of the methods well known in the art. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases. Any host organism, including a patient, mammal, and specifically a human, suffering from any of the above-described conditions can be treated by the administration of a composition comprising an effective amount of the compound of the invention or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems*, Sixth Edition, Williams & Wilkins (1995).

An effective dose for any of the conditions described herein can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the conditions described herein are those ranging from 0.1 mg/kg to 500 mg/kg of body weight per day as a single daily dose or divided daily doses. Preferred dosages for the described conditions range from 5-1500 mg per day. A more particularly preferred dosage for the desired conditions ranges from 25-750 mg per day. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients, which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The compound or its salts can be administered as a component of an elixir, suspension, syrup, wafer, chewing gum or the like. A syrup may contain, in addition to the active compounds, sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

A. Pharmaceutically Acceptable Salt Formulations

The one or more polysubstituted 4-[(2,3,4-trimethoxy)phenyl]-pyrrole compounds of Formula I or Formula II may also be formulated as pharmaceutically acceptable salts. In cases where compounds are sufficiently basic or acidic to form stable nontoxic acid or base salts, administration of a compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, oxalic, mandelic, malonate, tartarate, succinate, benzoate, ascorbate, α-ketoglutarate and α-glycerophosphate and the like. Suitable inorganic salts may also be formed, including, hydrochloride, phosphate, sulfate, nitrate, bicarbonate and carbonate salts and the like. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of higher metals (ferric), and salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, isopropyamine, trimethylamine, histidine, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salts, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

B. Pharmaceutically Acceptable Prodrugs

The invention also includes pharmaceutically acceptable prodrugs of the polysubstituted 4-[(2,3,4-tri-methoxy)phenyl]-pyrrole compounds of Formula I or Formula II. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability, or otherwise alter the properties of the compound. A number of prodrug ligands are known. Many have been described (Landis, *Therapeutic Delivery*, 4, 225-237 (2013), Moridani, *Methods and Principles in Medicinal Chemistry*, 47, 81-109 (2011), and De Clercq and Field, *Brit. J. Pharmacol*, 147, 1-11 (2006)). Any of these can be used in combination with the disclosed compounds to achieve a desired effect.

C. Methods of Use

In one embodiment, administration of a sufficient quantity of one or more polysubstituted 4-[(2,3,4-tri-methoxy)phenyl]-pyrrole compounds of Formula I or Formula II to inhibit the proliferation and cause cytotoxicity of one or more cancerous cells is provided. In certain aspects one or more live cancerous cells are contacted with an effective antiproliferative or cytotoxic amount of a compound of Formula I.

In terms of "treating" or "treatment", as used herein, the invention contemplates administration of a sufficient quantity of one or more polysubstituted 4-[(2,3,4-tri-methoxy) phenyl]-pyrrole compounds of Formula I or Formula II to a subject (e.g., human) to prevent, alleviate, reduce, or inhibit the progress of proliferation of one or more hyperproliferative cells (e.g., cancer cells and/or tumors).

The one or more polysubstituted 4-[(2,3,4-trimethoxy) phenyl]-pyrrole compounds of Formula I or Formula II and compositions containing such compounds may be administered by a variety of routes including, for example, oral (e.g., tablets, gel capsules, powders, granules, oral suspensions or solutions), sublingual or bucal, subcutaneous, intramuscular, intraperitoneal, intravenous, transdermal, topical, implants, intrathecal, intranasal, aerosol, local, or rectal.

The compounds described herein may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In still other embodiments, the disorder is cancer. In some such embodiments, the cancer is a solid tumor.

Other embodiments are directed to methods of treating cancer. Such methods typically include administering to a subject an effective amount of a compound described herein or a pharmaceutical composition thereof. In some such embodiments, the subject is a human cancer patient, and the cancer is selected from adenocarcinoma, lung cancer, non-small cell lung carcinoma, breast cancer, colorectal cancer, lymphoma, neuroblastoma, ovarian cancer, pancreatic cancer, mesothelioma, melanoma, glioblastoma, diffuse large B-cell lymphomas, systemic histiocytosis, or inflammatory myofibroblastic tumors. Such methods typically include administering to a subject an effective amount of a compound described herein or a pharmaceutical composition thereof.

In some embodiments, a compound described herein is used in the preparation of a medicament. In some such embodiments, the medicament is for use in treating cancer. In some embodiments, a compound described herein or pharmaceutical formulation thereof is used in treating cancer. In certain aspects the cancer is selected from adenocarcinoma, lung cancer, non-small cell lung carcinoma, breast cancer, colorectal cancer, lymphoma, neuroblastoma, ovarian cancer, pancreatic cancer, mesothelioma, melanoma, glioblastoma, diffuse large B-cell lymphomas, systemic histiocytosis, pediatric cancers, or inflammatory myofibroblastic tumors. In some such embodiments, the cancer is non-small cell lung carcinoma (NSCLC).

The magnitude of a prophylactic or therapeutic dose of a compound of any of the embodiments or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body. The compounds of the invention may also be administered directly to a site affected by a condition, as, for example, in the treatment of an accessible area of skin or an esophageal cancer. As indicated above, the compounds of the invention may be administered via oral, mucosal (including sublingual, bucal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration. Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The one or more polysubstituted 4-[(2,3,4-trimethoxy)phenyl]-pyrrole compounds of Formula I or Formula II can be provided alone or in combination with other compounds.

Some methods of the invention comprise the administration of a compound of the invention and an additional therapeutic agent (i.e., a therapeutic agent other than a compound of the invention). Thus, the compounds of the invention can be used in combination with at least one other therapeutic agent. For example, an additional pharmaceutically active agent, are not limited to, but can be selected from antibiotics, anti-emetic agents, anti-metabolite agents, hormonal agents, antidepressants, antifungal agents, anti-inflammatory agents, antineoplastic agents, antiviral agents, cytotoxic agents, and other anticancer agents, immunological agents, immunomodulatory agents, kinase inhibitors, alpha-interferons, [beta]-interferons, alkylating agents, hormones, and cytokines and combinations thereof. In one embodiment, the invention encompasses administration of an additional chemotherapeutic agent that demonstrates anti-cancer activity. In another embodiment, an additional therapeutic agent that demonstrates cytotoxic activity is administered to a subject such as a cancer patient. These additional pharmaceutically active compounds/agents may be traditional small organic chemical molecule or can be macromolecules such as proteins, antibodies, peptibodies, DNA, RNA or fragments of such macromolecules, or small molecule conjugates thereof.

Compounds of the present invention covered under Formula I or Formula II may also be administered with one or more additional treatment agents, i.e., a chemotherapeutic agent. Suitable candidates for the additional chemotherapeutic agent include for example but are not limited to taxanes (such as paclitaxel, docetaxel), and vinca alkaloids.

The compounds of the invention and the other therapeutic agents can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents or in multiple, separate formulations for each agent. Specifically, the administration of compounds of the present invention may be in conjunction with additional therapies known to those skilled in the art in the prevention or treatment of neoplasia, such as with radiation therapy or with cytostatic or cytotoxic agents. If formulated as a fixed dose, such combination products employ the compounds of this invention within the accepted dosage ranges. Compounds of any of the embodiments described herein may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent. There are large numbers of antineoplastic agents available in commercial use, in clinical evaluation and in pre-clinical development, which may be selected for treatment of neoplasia by combination drug chemotherapy.

Examples of specific pharmaceutically active agents that can be used in the treatment of cancers and that can be used in combination with one or more compounds of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; paclitaxel; thioguanine; idarubicin; dactinomycin; imatinib; gemcitabine; altretamine; asparaginase; bleomycin; capecitabine; carfilzomib; carmustine; cladisat. aq. NaCl solution; afatinib; axitinib; bosutinib; cyclophosphamine; cytarabine; decarazine; docetaxel; enzalutamide; everolimus; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; bertozimib; carbozantimib; cetuximab; azacitidine; ceritinib; clofarabine; cobimetinib; crizotinib; decitabine; desatinib; dexrazoxane; docetaxel; epirubicin; imatinib; oxaliplatin; erlotinib; raloxifene; fulvestrant; letrozole; gefitinib; gemtuzumab; idelalisib; ibrutanib; trastuzumab; olaparib; ixabepilone; lapatinib; lenalidomide; aminolevulinic acid; trametinib; temozolomide; nelarabine; sorafenib; nilotinib; neratinib; pegaspargase; pemetrexed; pomalidomide; pazopanib; ponatinib; regorafinib; rituximab; dasatinib; debrafinib; thalidomide; bexarotene; temsirolimus; bortezomib; veliparib; volasertib; vorinostat; capecitabine; zoledronic acid; anastrozole; sunitinib; aprepitant; and nelarabine; or a pharmaceutically acceptable salt thereof. Additional pharmaceutically active agents that can be used in the treatment of cancers and that can be used in combination with one or more compound of the present invention include: vascular endothelial growth factor (VEGF) inhibitors, endothelial growth factor (EGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand, insulin-like growth factor 1 receptor (IGFR-1) inhibitors, cFMS inhibitors, HER2 and HER3 inhibitors, c-met inhibitors, aurora kinase inhibitors, CDK 4 and/or 6 inhibitors, PI3K inhibitors, mTOR inhibitors, PKB inhibitors, CDK4 and/or CDK6 inhibitors, MEK ihibitors, BTK inhibitors, PKB inhibitors, pan-ErbB tyrosine kinase inhibitors, polo-like kinase inhibitors and B-raf inhibitors.

Other objects, features and advantages of the invention will become apparent to those skilled in the art from the following description and claims.

III. Modeling & Design of Compounds

Previous efforts to model and correlate the activity of various pyrrole analogs related to JG-03-14 with key interactions occurring with the colchicine site of tubulin have been reported. An early paper reported modestly successful attempts to define quantitative relationships between antiproliferative activities and docking models (Tripathi et al., *Bioorg. Med. Chem.* 16, 2235-2242 (2008)). In a later study, two distinct binding modalities were predicted for C-2 analogs in the colchicine site (Da et al., *ACS Med. Chem Lett.* 3, 53-57 (2012)). Another study identified the importance of weak interactions between Cys241β on tubulin with the H-bond acceptors in the 3,4-di-methoxyphenyl group at the pyrrole 4-position in JG-03-14 (Da et al., *Med. Chem. Comm.* 4, 417-21 (2013)). None of these provided a sufficiently detailed model to allow prediction of new structures with improved activity.

Recently, an atomic-scale colchicine site model more consistent with target structure conformation and at an effectively higher resolution than the 3.6 Angstrom resolution X-ray crystallographic protein structure currently available for tubulin has been developed using a combination of ensemble docking and structure activity relationships with multiple diverse chemical series, hydropathic analyses and 3D-QSAR (Da et al., *J. Med. Chem.* 56, 7382-95 (2013)).

The molecules described herein were designed with the help this quantitative molecular model developed expressly for in silico design and testing of small molecules binding at the colchicine site of αβ-tubulin. This model predicts the microtubule depolymerization activity of potential ligands bound at the site. The model is composed of three parts: (1) a set of optimized coordinates for the tubulin protein and active site atoms; (2) an expert system for orienting and docking the ligands within the site; and (3) a scoring function that rewards the type and strength of ligand-site interactions in a manner that quantitatively assesses the potential of the ligand for microtubule depolymerization activity (the scoring function utilizes HINT, a program developed at Virginia Commonwealth University).

With the help of this molecular model, an exemplary family of small molecules that are tetra-substituted pyrroles (C2, C3, C4, C5) has been designed, synthesized and tested for anticancer activity. The model reveals that C2 and C4 are positioned within very well defined subpockets of the site, C3 is positioned near a small hydrophobic indentation of the site and that C5 is at the entrance to the tubulin cavity. The model predicts that the C2-ethyl ester group is ideally positioned to fill its subpocket. Notably, the 3,4-dimethoxyphenyl group in JG-03-14 can be positioned to be even more tightly bound by the addition of a third methoxy group. Thus, a 2,3,4-trimethoxyphenyl group at the pyrrole C-4 position is predicted to have an even tighter interaction with tubulin by additional hydrophobic contacts and through a specific and more directed H-bond acceptor interaction from Cys241β. This is in sharp contrast to the relatively poor potency reported for the corresponding 3,4,5-trimethoxyphenyl analog of JG-03-14 (Da et al., *J. Med. Chem.* 56, 7382-95 (2013)), even though it contains this common moiety found in many other colchicine-site directed inhibitors. It is also noteworthy that Cys241β is mutated to Ser in the β-III isotype of tubulin, which can be expressed in taxane-resistant or vinorelbine-resistant cancers. One would expect that this Ser residue in β-III type tubulin would maintain this key directed H-bond acceptor interaction to these pyrrole compounds, and that these new 4-(2,3,4-trimethoxyphenyl)-pyrroles would advantageously maintain their potency against cancer cells containing drug-resistant β-III isotype tubulin.

Synthesis of the Active Compounds. The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition.

The compounds of the present invention can be readily prepared by those skilled in the art of organic synthesis using commonly known methods. For example, representative 4-[(2,3,4-trimethoxy)phenyl-pyrrole compounds of Formula I or Formula II are prepared through the corresponding intermediate 2-(2,3,4-trimethoxy)phenyl) vinamidinium salt as depicted in Scheme 1 shown below (Gupton et al., *J. Org. Chem.* 55, 4735-40 (1990); Smith et al., *Tetrahedron Lett.* 3965-44 (2013)) followed by halogenation (Gupton et al., *Arch Pharm. Pharm. Med. Chem.* 333, 3-9 (2000)) or through palladium-mediated cross-coupling of the corresponding 4-halopyrrole with a suitable 2,3,4-trimethoxyphenyl boronic acid derivative (Da et al., *Med. Chem. Comm.* 4, 417-21 (2013); Banwell et al., *Eur. J. Org. Chem.* 14, 3043-60 (2006); Handy et al., *J. Org. Chem.* 69, 2362-66 (2004)).

In the above reactions, it may be preferred or necessary to manipulate various functional groups or to protect various sensitive or reactive groups present in the starting materials so as to prevent said groups from interfering with the reactions. Such functional group manipulation can be accomplished by those skilled in the art using methods taught by Michael B. Smith in the *Compendium of Organic Synthetic Methods*, Vols 1-12 (John Wiley & Sons) or by Richard C. Larock in *Comprehensive Organic Transformations: A Guide to Functional Group Preparations*, 2$^{nd}$ Ed. (Wiley-VCH, New York, 1999). Similarly, it may be preferred or necessary to protect various sensitive or reactive groups present in the starting materials or intermediates so as to prevent said groups from interfering with the reactions. Such protection/deprotection reactions may be carried out in a well-known manner as taught by Theodora W. Green and Peter G. M. Wuts, in *Protective Groups in Organic Chemistry Third Edition* (Wiley, 1999) or using methods from references cited therein or of the like. The protecting group may be removed after the reaction in a manner known per se.

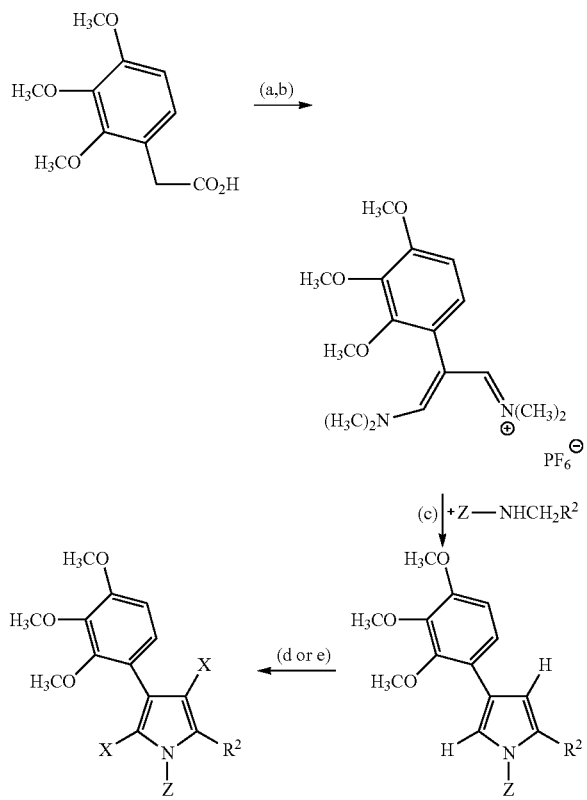

Scheme 1

Where a = POCl$_3$, DMF, heat; b = NaPF$_6$ and H$_2$O; c = NaO-t-Bu, DMF, heat; d = pyridinium tribromide for X = Br, KOH, DMF; e = N-chloro-succinimide for X = Cl, KOH, DMF.

Step 1: The 2,3,4-trimethoxyphenylacetic acid is added in portions as a solid to a pre-formed cooled solution of phosphorous oxychloride in dry dimethyl formamide (DMF). When the addition is complete, the cooling bath is removed and the resulting solution is heated below 90 degrees for about 2 hours. After cooling to room temperature, ice is added, and the reaction mixture is poured into a solution of hexafluorophosphate in water producing an orange precipitate.

The reaction may be carried out at temperatures in the range of −80° C. to +150° C., preferably in the range of 0-5° C. to +80° C. The time of reaction may be from 30 minutes to approximately 24 hours.

Step 2: A mixture of the appropriate glycine derivative and the intermediate 2-(2,3,4-trimethoxyphenyl)vinamidinium salt is added to a cooled solution of sodium t-butoxide in dry DMF. Once the addition is complete, the cooling bath is removed and the reaction mixture is heated at reflux for approximately 24 hours.

The reaction may be carried out in any polar aprotic solvent that does not react with sodium t-butoxide, but is preferably dimethyl formamide. The reaction temperatures are in the range of 0° C. to +150° C., and preferably in the range of +30° C. to +80° C. The time of reaction may be from 30 minutes to approximately 48 hours.

Step 3: The resulting 4-(2,3,4-trimethoxyphenyl)pyrrole was dissolved in DMF containing a base, preferably KOH, and a suitable brominating agent or chlorinating agent is added. The reactivity of the halogenating agent must be gentle enough so as to avoid or minimizet halogenation of the 2,3,4-trimethoxyphenyl ring. The preferred brominating agent is pyridinium tribromide and the preferred chlorinating agent is N-chlorosuccinimide.

When carrying out this reaction under basic conditions, the base may be selected from sodium, lithium, potassium, barium, calcium, magnesium, aluminum, ammonium, or quarternary ammonium hydroxides, lower alkoxides (e.g. methoxides, ethoxides, tert-butoxides), carbonates, borates, oxides, hydrides, or amides of lower secondary amines (e.g. diisopropyl amides, methylphenyl amides).

The reaction may be carried out at temperatures in the range of −10° C. to +150° C., preferably in the range of 0-5° C. to +30° C. The time of reaction may be from 30 minutes to approximately 24 hours.

Experimental conditions for the various general synthetic schemes 1-4 are discussed in more detail below.

Scheme 2

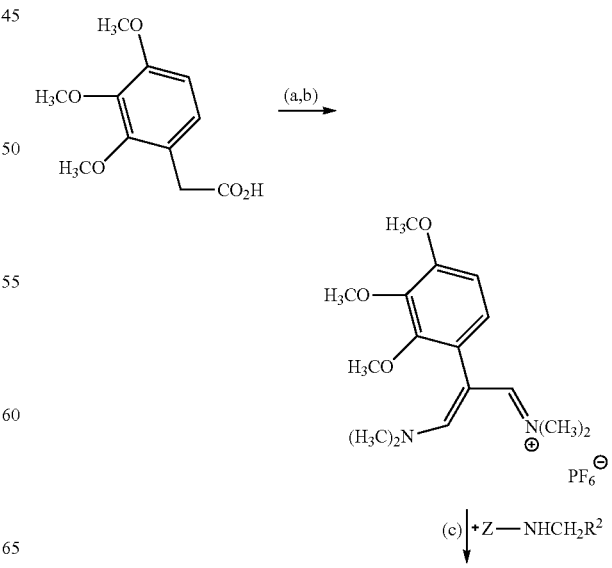

-continued

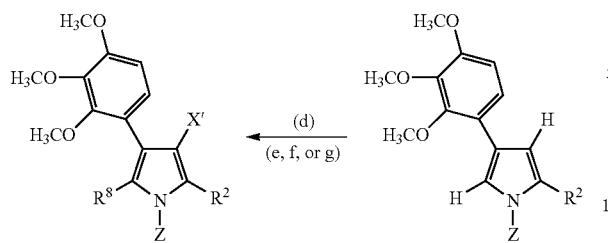

Where a = POCl₃, DMF, heat; b = NaPF₆ and H₂O; c = NaO-t-Bu, DMF, heat; d = POCl₃, DMF, microwave heating; e = pyridinium tribromide for X' = Br, KOH, DMF; f = N-chlorosuccinimide for X' = Cl, KOH, DMF; g = iodine, KOH, DMF, for X' = I.

Step 1: The 2,3,4-trimethoxyphenylacetic acid is added in portions as a solid to a pre-formed cooled solution of phosphorous oxychloride in dry dimethyl formamide (DMF). When the addition is complete, the cooling bath is removed and the resulting solution is heated below 90 degrees for about 2 hours. After cooling to room temperature, ice is added, and the reaction mixture is poured into a solution of hexafluorophosphate in water producing an orange precipitate.

The reaction may be carried out at temperatures in the range of –80° C. to +150° C., preferably in the range of 0-5° C. to +80° C. The time of reaction may be from 30 minutes to approximately 24 hours.

Step 2: A mixture of the appropriate glycine derivative and the intermediate 2-(2,3,4-trimethoxyphenyl)vinamidinium salt is added to a cooled suspension of solid sodium hydride or sodium tert-butoxide in dry DMF. Once the addition is complete, the cooling bath is removed and the reaction mixture is heated at reflux for approximately 24 hours.

The reaction may be carried out in any polar aprotic solvent that does not react with sodium hydride, but is preferably dimethyl formamide. The reaction temperatures are in the range of 0° C. to +150° C., and preferably in the range of +30° C. to +80° C. The time of reaction may be from 30 minutes to approximately 48 hours.

Step 3: The resulting 4-(2,3,4-trimethoxyphenyl)pyrrole was dissolved in DMF containing a base, preferably KOH, and a suitable brominating agent, chlorinating agent, or iodinating agent is added. The reactivity of the halogenating agent must be low enough so as not to halogenate the trimethoxyphenyl ring. The preferred brominating agent is pyridinium tribromide, the preferred chlorinating agent is N-chlorosuccinimide, the preferred iodinating agent is iodine.

When carrying out this reaction under basic conditions, the base may be selected from sodium, lithium, potassium, barium, calcium, magnesium, aluminum, ammonium, or quarternary ammonium hydroxides, lower alkoxides (e.g. methoxides, ethoxides, tert-butoxides), carbonates, borates, oxides, hydrides, or amides of lower secondary amines (e.g. diisopropyl amides, methylphenyl amides).

The reaction may be carried out at temperatures in the range of –10° C. to +150° C., preferably in the range of 0-5° C. to +30° C. The time of reaction may be from 30 minutes to approximately 24 hours.

Scheme 3

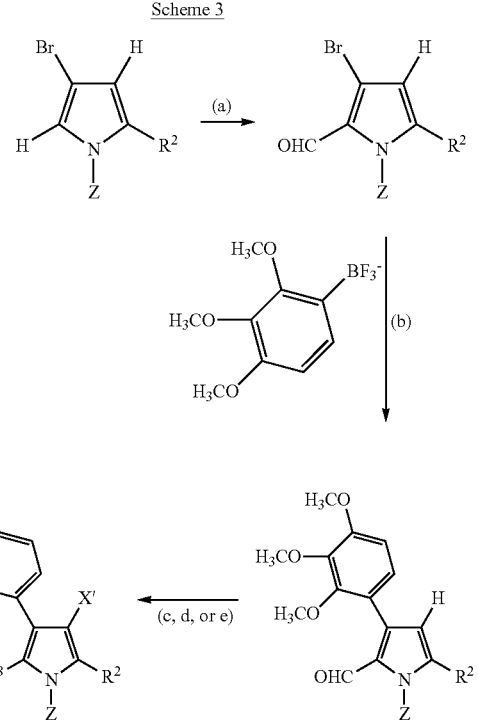

Where a = POCl₃, DMF, heat; b = Pd[(P(phenyl)₃)₄, toluene/ethanol/water, microwave heating; c = pyridinium tribromide for X' = Br, KOH, DMF; d = N-chlorosuccinimide for X' = Cl, KOH, DMF; e = iodine, KOH, DMF, for X' = I.

Scheme 4

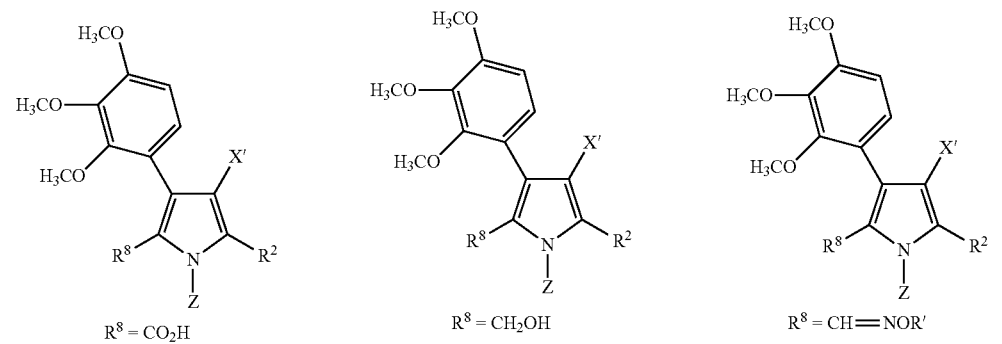

-continued
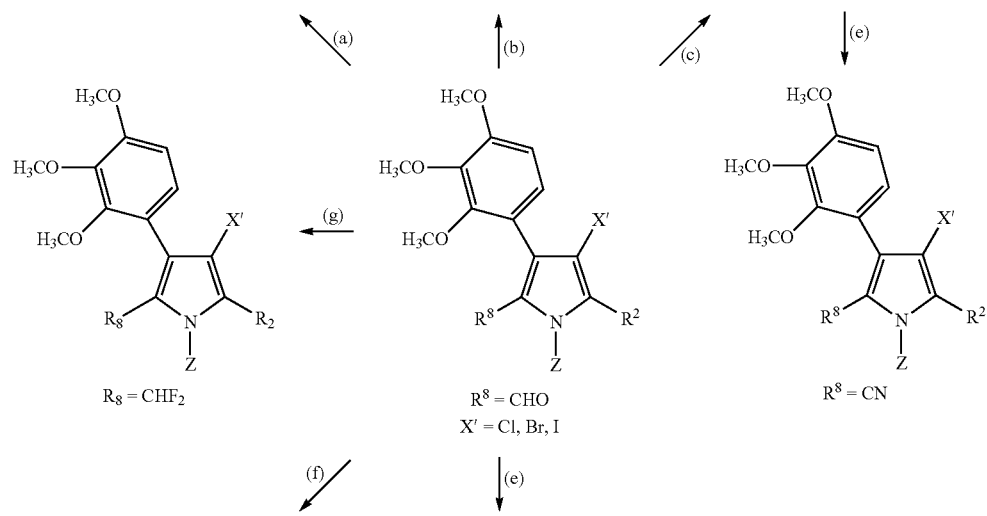
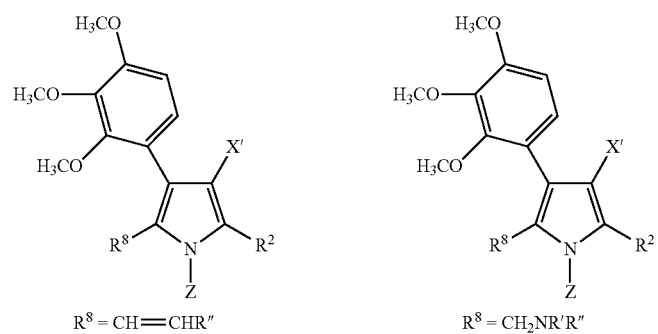
Where a = NaClO$_2$, DMSO/water, RT; b = NaBH$_4$ in isopropanol, heat; c = NH$_2$OR', pyridine, ethanol, heat; d = POCl$_3$, chloroform, RT; e = R'R"NH, NaCNBH$_3$, acetic acid, THF, RT; f = NaH, R" - phosphonium salt, THF, RT or heat; g = DAST, dischloromethane, RT. RT = room temperature.
-continued
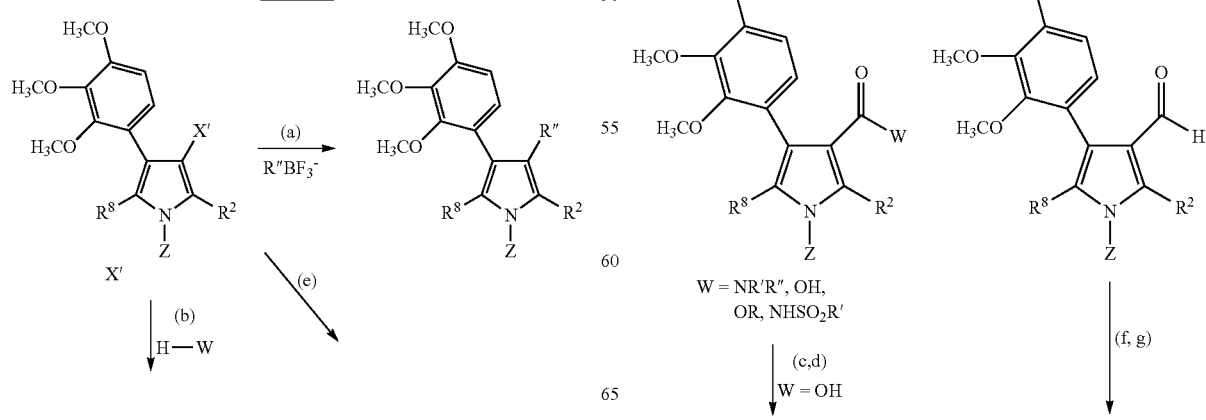

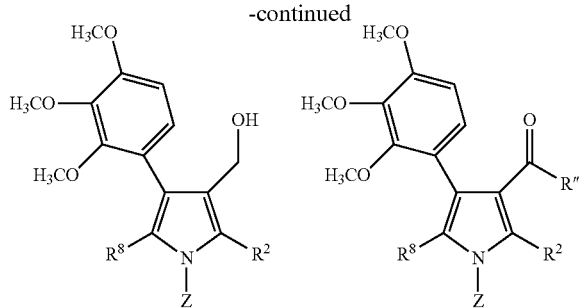

Where a = Pd[(P(phenyl)$_3$)$_4$, toluene/ethanol/water, microwave heating; b = Mo(CO)$_6$, Et$_4$N$^+$Cl$^-$, dioxane, microwave heat; c = HOBt, EDC, dichloromethane, RT; d = NaBH$_4$ THF/water, 0° C.; e = CO, H$_2$, toluene, Pd(OAc)$_2$, 100° C.; f = R″—Li or R″—MgBr, ether or THF; g = MnO$_2$•RT = room temperature, Bt = 1,2,-benzotriazole.

IV. Examples

The following examples as well as the figures are included to demonstrate preferred embodiments of the invention. It should be appreciated by those of skill in the art that the techniques disclosed in the examples or figures represent compounds and/or techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a similar result without departing from the spirit and scope of the invention. The following examples are understood to be illustrative only and are not intended to limit the scope of the present invention in any way. All intermediates and final products have been completely characterized by conventional proton NMR, mass spectral analyses and standard analytical methods well known to those skilled in the art. The following Examples are provided to illustrate various embodiments of the invention, including the synthesis of several different compounds, which can be used in the practice of the invention, as well as in vitro and in vivo testing of these compounds, but these examples should not be considered as limiting in any way.

Example 1

4-(2,3,4-trimethoxyphenyl)-5-formyl-1H-pyrrole 2-carboxylic acid ethyl ester (NT-7-34)

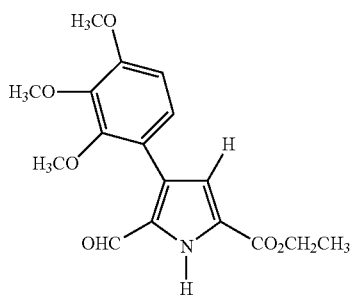

To a 20 mL microwave vial was added 4-bromo-5-formyl pyrrole 2-carboxylic acid ethyl ester (0.5 g, 2.032 mmol), 2,3,4-trimethoxyphenyl trifluoroborate (0.723 g, 2.64 mmol), Pd-tetrakis(triphenylphosphine) (0.023 g, 0.02 mmol), Hunig's base (0.341 g, 2.64 mmol) in 3:1 toluene; ethanol with 20 drops of water. The reaction mixture was microwaved for 110° C. for 2 hours. After cooling the reaction mixture to room temperature, it was filtered through a short silica plug and the resulting mixture was evaporated in vacuo. The crude product was dried using a Kulgelrohr apparatus to give a reddish brown solid (0.75 g, 110%). The crude residue was subjected to flash chromatography on a Biotage SP-1 instrument with a silica column in which case 0.51 g (75% yield) of a dark brown solid was obtained upon elution with seven column volumes of hexane/ethyl acetate gradient. This solid exhibited the following properties: m.p. 138-140° C.; $^1$H NMR (acetone-d$_6$, 500 MHz) δ 1.36 (t, J=7.2 Hz, 3H), 3.66 (s, 3H), 3.88 (s, 3H), 3.91 (s, 3H), 4.36 (q, J=7.2 Hz, 2H), 6.89 (d, J=8.5 Hz, 1H), 6.96 (s, 1H), 7.11 (d, J=8.5 Hz, 1H), 9.63 (s, 1H); $^{13}$C NMR (acetone-d$_6$, 75 MHz) δ 180.3, 159.0, 154.6, 152.0, 142.4, 130.9, 130.7, 126.7, 124.6, 117.1, 107.5, 104.9, 60.9, 60.4, 60.2, 55.5, 13.6; IR (neat) 1709 and 1660 cm$^{-1}$; HRMS (ES) m/z calcd for C$_{17}$H$_{19}$NO$_6$ [M+Na]$^+$ 356.1105, found 356.1077.

Example 2

3-Bromo-4-(2,3,4-trimethoxyphenyl)-5-formyl-1H-pyrrole 2-carboxylic acid ethyl ester (NT-7-30)

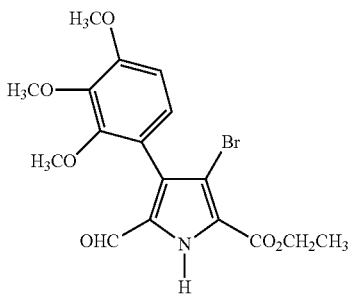

To a 100 mL round bottom flask equipped with a stir bar, was added 4-(2,3,4-tri-methoxyphenyl)-5-formyl pyrrole 2-carboxyic acid ethyl ester (0.100 g, 0.300 mmol) and potassium hydroxide (0.034 g, 0.6 mmol) in 15 mL of DMF. The reaction mixture was allowed to stir for 15 minutes at room temperature, after which N-bromo succinimide (0.053 g, 0.33 mmol) was added and the reaction mixture was stirred overnight at room temperature. The reaction mixture was diluted with 30 mL water and 15 mL of sodium thiosulfate solution was added to the reaction mixture. It was extracted with ethyl acetate (3×15 mL). The combined ethyl acetate layers were dried over anhydrous sodium sulfate, filtered and concentrated to give a dark brown solid (0.12 g, 96%). This solid exhibited the following properties: m.p. 158-160° C.; $^1$H NMR (CDCl$_3$) δ 1.43 (t, J=7.2 Hz, 3H), 3.68 (s, 3H), 3.93 (s, 3H), 3.94 (s, 3H), 4.45 (q, J=7.2 Hz, 2H), 6.81 (d, J=8.5 Hz, 1H), 7.04 (d, J=8.5 Hz, 1H), 9.45 (s, 1H); $^{13}$C NMR (CDCl$_3$) δ 181.0, 159.5, 154.5, 151.8, 142.3, 131.2, 130.2, 126.7, 124.6, 116.7, 107.2, 105.3, 61.6, 60.2, 56.0, 14.2; IR (neat) 1708 and 1660 cm$^{-1}$; HRMS (ES) m/z calcd for C$_{17}$H$_{18}$NNaBrO$_6$ 434.0210, 436.0192 found 434.0199, 436.0186.

Example 3

3-Chloro-4-(2,3,4-trimethoxyphenyl)-5-formyl-1H-pyrrole 2-carboxylic acid ethyl ester (KL-4-44)

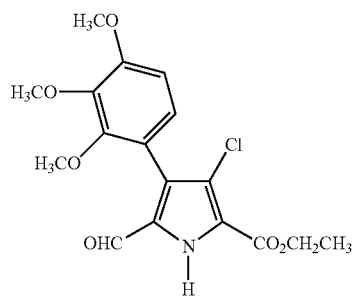

To a 100 mL round bottom flask equipped with a stir bar, was added 4-(2,3,4-tri-methoxyphenyl)-5-formyl pyrrole 2-carboxylic acid ethyl ester (Ex. 1, 0.350 g, 1.05 mmol) and potassium hydroxide (0.118 g, 2.1 mmol) in 15 mL of DMF. The reaction mixture was allowed to stir for 15 minutes at room temperature, after which N-chlorosuccinimide (0.140 g, 1.05 mmol) was added and the reaction mixture was stirred overnight at room temperature. The reaction mixture was diluted with 30 mL water and 15 mL of sodium thiosulfate solution was added to the reaction mixture. It was extracted with ethyl acetate (3×15 mL). The combined ethyl acetate layers were dried over anhydrous sodium sulfate, filtered and concentrated to give a dark brown solid (0.33 g, 86%). This solid exhibited the following properties: m.p. 193-195° C.; $^1$H NMR (CDCl$_3$) δ 1.43 (t, J=7.2 Hz, 3H), 3.68 (s, 3H), 3.93 (s, 3H), 3.94 (s, 3H), 4.45 (q, J=7.2 Hz, 2H), 6.81 (d, J=8.5 Hz, 1H), 7.04 (d, J=8.5 Hz, 1H), 9.45 (s, 1H); $^{13}$C NMR (CDCl$_3$) δ 181.0, 159.4, 154.5, 151.8, 142.3, 131.1, 130.1, 126.7, 124.6, 116.7, 107.2, 105.3, 61.6, 61.1, 56.0, 14.2; IR (neat) 1696 and 1669 cm$^{-1}$; HRMS (ES) m/z calcd for C$_{17}$H$_{18}$NNaClO$_6$ 390.0710 found 390.0715.

Example 4

3-Iodo-4-(2, 3, 4-trimethoxyphenyl)-5-formyl-1H-pyrrole 2-carboxylic acid ethyl ester (NT-9-3)

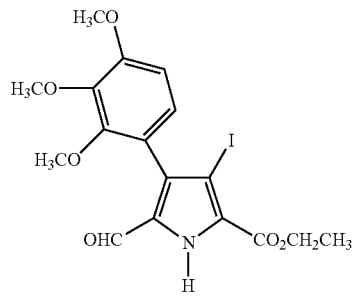

To a 100 mL round bottom flask equipped with a stir bar, was added 4-(2,3,4-tri-methoxyphenyl)-5-formyl pyrrole 2-carboxylic acid ethyl ester (Ex. 1, 0.250 g, 0.75 mmol) and potassium hydroxide (0.168 g, 3.0 mmol) in 15 mL of DMF. The reaction mixture was allowed to stir for 15 minutes at room temperature, after which iodine (0.38 g, 1.5 mmol) was added and the reaction mixture was stirred overnight at room temperature. The reaction mixture was diluted with 30 mL water and 15 mL of sodium thiosulfate solution was added to the reaction mixture. It was extracted with ethyl acetate (3×15 mL). The combined ethyl acetate layers were dried over anhydrous sodium sulfate, filtered and concentrated to give a yellow solid (0.340 g, 98%). This solid exhibited the following properties: m.p. 126-128° C.; $^1$H NMR (CDCl$_3$) δ 1.45 (t, J=7.2 Hz, 3H), 3.66 (s, 3H), 3.95 (s, 3H), 3.94 (s, 3H), 4.44 (q, J=7.2 Hz, 2H), 6.80 (d, J=8.5 Hz, 1H), 6.99 (d, J=8.5 Hz, 1H), 9.42 (s, 1H); $^{13}$C NMR (CDCl$_3$) δ 181.7, 160.4, 153.9, 151.2, 142.6, 130.7, 130.6, 127.3, 125.7, 119.5, 116.4, 107.6, 61.3, 61.0, 60.9, 56.0, 14.3; IR (neat) 1712 and 1661 cm$^{-1}$; HRMS (ES) m/z calcd for C$_{17}$H$_{18}$NIO$_6$ 460.0022 found 460.0252.

Example 5

3-Bromo-5-(hydroxymethyl)-4-(2,3,4-trimethoxyphenyl)-1H-pyrrole 2-carboxylic acid ethyl ester (AH-3-19)

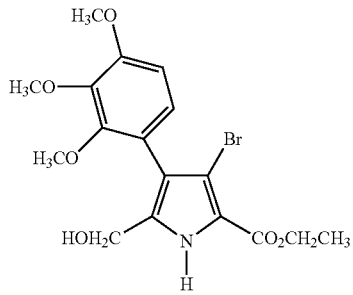

To a 100 mL round bottom flask equipped with a magnetic stir bar, was added 3-bromo-4-(2,3,4-trimethoxyphenyl)-5-formyl pyrrole ethyl ester (Ex. 2, 0.300 g, 0.73 mmol), and sodium borohydride (0.110 g, 2.91 mmol) in 35 mL of isopropanol. The reaction mixture was refluxed for 2 hours. The reaction mixture was allowed to cool to room temperature and was evaporated in vacuo. The crude residue was diluted with 30 mL ethyl acetate and the organic layer was washed with water (2×30 mL) and brine (2×30 mL). The organic extract was dried with anhydrous sodium sulfate and was evaporated in vacuo and dried using a Kugelrohr apparatus to give a viscous oil (0.290 g, 86%). The product exhibited the following characteristics: b.p. 72° C. at 0.37 Torr; $^1$H NMR (CDCl$_3$, 500 MHz) δ 1.28 (t, J=7.2 Hz, 3H), 3.61 (s, 3H), 3.93 (s, 3H), 3.95 (s, 3H), 4.43 (m, 4H), 6.80 (d, J=8.4 Hz, 1H), 6.99 (d, J=8.4 Hz, 1H); $^{13}$C NMR (CDCl$_3$, 125 MHz) δ 160.4, 153.5, 151.72, 142.3, 134.0, 127.1, 120.7, 119.5, 119.3, 107.7, 104.9, 61.4, 61.4, 61.2, 56.7, 56.0, 14.3; IR (neat) 1685 cm$^{-1}$; HRMS (ES) m/z calcd for C$_{17}$H$_{20}$NNaBrO$_6$ 436.0366, 438.0348 found 436.0255, 438.0192.

Example 6

3-Bromo-4-(2,3,4-trimethoxyphenyl)-5-(difluoromethinyl)-1H-pyrrole 2-carboxylic acid ethyl ester (NT-7-31)

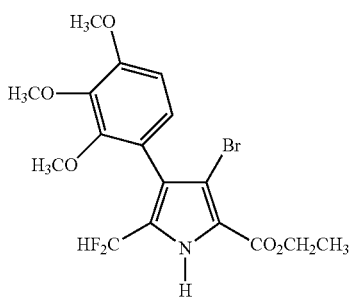

To a 100 mL round bottom flask equipped with a stir bar, was added DAST (0.156 g, 0.97 mmol) in 20 mL of dichloromethane. 3-Bromo-4-(2,3,4-trimethoxyphenyl)-5-formyl pyrrole 2-carboxyic acid ethyl ester (Ex. 2) was slowly added to the reaction mixture, which was stirred at room temperature overnight. The reaction mixture was diluted with 25 mL of water and the organic layer was washed with water (2×15 mL) of brine (2×15 mL), dried over anhydrous sodium sulfate, filtered, evaporated and dried using a Kulgelrohr apparatus to give a pale yellow solid (0.095 g, 91%). This solid exhibited the following properties: m.p. 149-151° C.; $^1$H NMR (acetone-$d_6$) δ 1.36 (t, J=7.2 Hz, 3H), 3.65 (s, 3H), 3.86 (s, 3H), 3.91 (s, 3H), 4.36 (q, J=7.2 Hz, 2H), 6.65 (t, J=53.4 Hz, 1H), 6.86 (d, J=8.7 Hz, 1H), 6.94 (d, J=8.4 Hz, 1H); $^{13}$C NMR (acetone-$d_6$) δ 159.0, 154.4, 151.9, 142.4, 126.6, 126.2 (t, J=25 Hz, 1C), 123.8 (t, J=5.7 Hz, 1C,), 121.5, 117.6, 109.5 (t, J=189 Hz, 1C), 107.4, 104.5, 60.4, 60.2, 60.1, 55.4, 13.7; IR (neat) 1703 and 1660 cm$^{-1}$; HRMS (ES) m/z calcd for $C_{17}H_{18}NBrF_2O_5$ 434.0409, 436.0391 found 434.0242, 436.0217.

Example 7

3-Bromo-5-vinyl-4-(2,3,4-trimethoxyphenyl)-1H-pyrrole 2-carboxylic acid ethyl ester (MW-4-62)

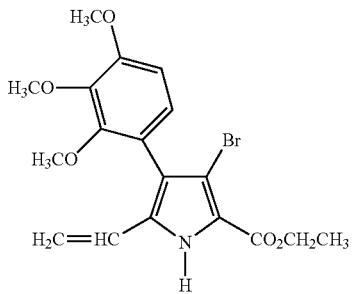

To a 20 mL microwave vial equipped with a magnetic stir bar, was added 60% NaH (0.049 g, 1.21 mmol) and methyltriphenylphosphonium iodide (0.245 g, 0.608 mmol) in 6 mL of anhydrous THF. The reaction mixture was allowed to stir for 30 minutes under a nitrogen atmosphere. Then 3-bromo-5-formyl-4-(2,3,4-trimethoxyphenyl)-1H-pyrrole-2-carboxylic acid ethyl ester (Ex. 2, 0.100 g, 0.243 mmol), dissolved in 6 mL of anhydrous THF, was added dropwise to the reaction mixture. The reaction mixture was subjected to microwave conditions for 2 hours at 40° C. After completion, excess NaH was quenched by the addition of 5 mL of methanol. The reaction mixture was diluted with 100 mL water and was extracted with ethyl acetate (3×25 mL). The organic layers were combined, dried over anhydrous sodium sulfate and evaporated in vacuo. The crude product was dried using a Kulgelrohr apparatus to give a tacky yellow solid. The crude residue was subjected to flash chromatography on a Biotage SP-1 instrument with a silica column in which case 0.140 g (50% yield) of a pale yellow solid was obtained upon elution with five column volumes of a hexane/ethyl acetate gradient. This solid exhibited the following properties: $^1$H NMR (CDCl$_3$, 500 MHz) δ 1.43 (t, J=7.2 Hz, 3H), 3.68 (s, 3H), 3.92 (s, 3H), 3.93 (s, 3H), 4.41 (q, J=7.2 Hz, 2H), 5.19 (d, J=11 Hz, 1H), 5.50 (d, J=18 Hz, 1H), 6.37 (dd, J=18 Hz, J=11 Hz, 1H), 6.74 (d, J=8.7 Hz, 1H), 6.88 (d, J=8.7 Hz, 1H), 9.49 (s, 1H); $^{13}$C NMR (CDCl$_3$, 125 MHz) δ 160.4, 153.7, 152.5, 142.3, 131.9, 126.9, 125.4, 123.3, 119.6, 119.2, 113.4, 107.0, 106.3, 61.1, 61.0, 60.9, 55.9, 14.4; IR (neat) 1668 cm$^{-1}$; HRMS (ES) m/z calcd for $C_{18}H_{21}N_1BrO_5$ 432.0417, 434.0399 found 432.0411, 434.0367.

Example 8

Cis-3-Bromo-5-(3-methoxy-3-oxoprop-1-en-1-yl)-4-(2,3,4-trimethoxyphenyl)-1H-pyrrole-2-carboxylic acid ethyl ester (Ex. 8a, NT-8-77-fr4) and Trans-3-Bromo-5-(3-methoxy-3-oxoprop-1-en-1-yl)-4-(2,3,4-trimethoxyphenyl)-1H-pyrrole-2-carboxylic acid ethyl ester (Ex. 8b, NT-8-77-fr6)

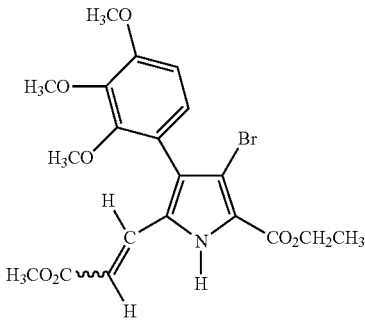

To a 100 mL round bottom flask equipped with a magnetic stir bar, was added 3-bromo-5-formyl-4-(2,3,4-trimethoxyphenyl)-1H-pyrrole-2-ethyl ester (Ex. 2, 0.1 g, 0.243 mmol), methyl (triphenylphosphoranylidene)acetate (0.090 g, 0.29 mmol) in 15 mL of anhydrous THF. The reaction mixture was allowed to stir for 24 hours at room temperature. The reaction mixture was evaporated in vacuo to give a pale yellow residue, which was diluted with 50 mL water and was extracted with ethyl acetate (3×15 mL). The organic layers were combined, dried over anhydrous sodium sulfate and evaporated in vacuo. The crude product was dried using a Kulgelrohr apparatus to give a pale yellow solid. The crude residue was subjected to flash chromatography on a Biotage SP-1 instrument with a silica column in which case 0.040 g (35% yield) of the cis-isomer of 3-bromo-5-(3-methoxy-3- oxoprop-1-en-1-yl)-4-(2,3,4-trimethoxyphenyl)-1H-pyrrole-2-carboxylic acid ethyl ester (Ex. 8, NT-8-77-fr4) was obtained upon elution with four column volumes of hexane/ethyl acetate gradient.

The cis-isomer of 3-bromo-5-(3-methoxy-3-oxoprop-1-en-1-yl)-4-(2,3,4-trimethoxy-phenyl)-1H-pyrrole-2-carboxylic acid ethyl ester (Ex. 8a, NT-8-77-fr4) exhibited the following properties: m.p. 174-176° C.; $^1$H NMR (acetone-$d_6$) δ 1.42 (t, J=7.2 Hz, 3H), 3.63 (s, 3H), 3.85 (s, 3H), 3.86 (s, 3H), 3.92 (s, 3H), 4.42 (q, J=7.2 Hz, 2H), 5.85 (d, J=12.6 Hz, 1H), 6.60 (d, J=12.6 Hz, 1H), 6.88 (s, 2H); $^{13}$C NMR (acetone-$d_6$) δ 167.2, 160.7, 154.2, 152.3, 142.3, 132.3, 129.4, 128.5, 127.7, 126.6, 122.2, 118.5, 116.4, 107.1, 61.6, 61.1, 61.0, 55.9, 51.7, 14.3; IR (neat) 1696 and 1669 cm$^{-1}$; HRMS (ES) m/z calcd for $C_{20}H_{22}NBrO_7$ [M+Na]$^+$ 490.0472, 492.0454 found 490.0461, 492.0446.

The corresponding trans-isomer of 3-bromo-5-(3-methoxy-3-oxoprop-1-en-1-yl)-4-(2,3,4-trimethoxy-phenyl)-1H-pyrrole-2-carboxylic acid ethyl ester (Ex. 8b, NT-8-77-fr6 (0.074 g, 65% yield) was obtained upon elution with six column volumes of a hexane/ethyl acetate gradient and the resulting material exhibited the following properties: m.p. 187-189° C.; $^1$H NMR (acetone-$d_6$) δ 1.37 (t, J=7.2 Hz, 3H), 3.65 (s, 3H), 3.66 (s, 3H), 3.86 (s, 3H), 3.93 (s, 3H), 4.36 (q, J=7.2 Hz, 2H), 6.39 (d, J=16.2 Hz, 1H), 6.89 (s, 2H), 7.32 (d, J=16.2 Hz, 1H); $^{13}$C NMR (acetone-$d_6$) δ 167.1, 160.6, 154.1, 152.3, 142.2, 132.3, 129.4, 128.5, 127.7, 126.6, 122.2, 118.4, 116.4, 107.1, 61.6, 61.1, 61.0, 55.9, 51.7, 14.3; IR (neat) 1696 and 1669 cm$^{-1}$; HRMS (ES) m/z calcd for $C_{20}H_{22}NBrO_7$ [M+Na]$^+$ 490.0472, 492.0454; found 490.0461, 492.0446.

Example 9

3-Bromo-4-(2,3,4-trimethoxyphenyl)-5-carboxy-1H-pyrrole 2-carboxylic acid ethyl ester (NT-9-18)

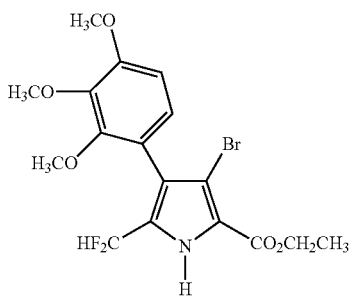

To a 100 mL round bottom flask equipped with a magnetic stir bar, was added 3-bromo-4-(2,3,4-trimethoxyphenyl)-5-formyl-1H-pyrrole 2-carboxlic acid ethyl ester (Ex. 2, 0.100 g, 0.243 mmol) which was previously dissolved in 10 mL of DMSO. Sodium hydrogen phosphate, (NaHPO$_4$.H$_2$O) (0.034 g, 0.243 mmol), dissolved in 5 mL of water, was added and the reaction mixture was cooled in ice bath at 0° C. Sodium chlorite (0.066 g, 0.73 mmol), dissolved in 5 mL water, was added drop-wise by means of a dropping funnel. After the addition was over, the ice bath was removed and the reaction mixture was stirred for 24 h at room temperature. The reaction mixture was cooled in an ice bath and was acidified to pH 2 by drop-wise addition of 6M HCl. It was then diluted with 5 mL of brine and was extracted with ethyl acetate (3×15 mL). The organic phase was dried over anhydrous sodium sulfate and was concentrated in vacuo to give a light yellow solid (0.090 g, 86%); m.p. 173-175° C.; $^1$H NMR (acetone-$d_6$, 300 MHz) δ 1.37 (t, J=7.2 Hz, 3H), 3.65 (s, 3H), 3.81 (s, 3H), 3.88 (s, 3H), 4.35 (q, J=7.2 Hz, 2H), 6.76 (d, J=8.5 Hz, 1H), 6.83 (d, J=8.5 Hz, 1H); $^{13}$C NMR (acetone-$d_6$, 75 MHz) δ 180.2, 158.8, 153.9, 152.2, 142.1, 128.0, 126.5, 125.8, 122.1, 120.1, 106.9, 105.7, 60.6, 60.0, 59.9, 55.3, 13.6; IR (neat) 3277, 1718 and 1701 cm$^{-1}$; HRMS (ES, M+Na) m/z calcd for $C_{17}H_{19}NBrO_7Na$, 450.0159 found 450.0268.

Example 10

Cis/Trans-3-Bromo-4-(2,3,4-trimethoxyphenyl)-5-oximino-1H-pyrrole 2-carboxylic acid ethyl ester (NT-7-45), Cis-3-Bromo-4-(2,3,4-trimethoxyphenyl)-5-oximino-1H-pyrrole 2-carboxylic acid ethyl ester (NT-8-6-fr6/7), and Trans-3-Bromo-4-(2,3,4-trimethoxyphenyl)-5-oximino-1H-pyrrole 2-carboxylic acid ethyl ester (NT-8-6-fr8)

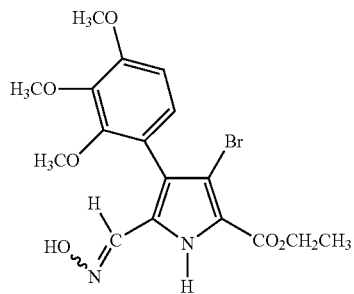

To a 100 mL round bottom flask equipped with a stir bar, was added 4-(2',3',4'-trimethoxyphenyl)-5-formyl-pyrrole-2-ethyl ester (0.13 g, 0.315 mmol), hydroxyl amine hydrochloride (0.022 g, 0.315 mmol), 0.1 mL of pyridine in 15 mL of ethanol. The reaction mixture was allowed to reflux for 2 hours. The reaction mixture was cooled and evaporated to give a crude residue. Water (10 mL) was added to the residue and the solution was cooled in an ice bath and stirred until the oxime crystallized. The solid was filtered and washed with water (2×15 mL) and dried to give cis/trans-3-Bromo-4-(2,3,4-trimethoxyphenyl)-5-oximino-1H-pyrrole 2-carboxylic acid ethyl ester (NT-7-45), as an orange solid (0.091 g, 68%): $^1$H NMR (acetone-$d_6$) δ 1.36 (t, J=5.0 Hz, 3H), 1.40 (t, J=5.0 Hz, 3H), 3.64 (s, 3H), 3.65 (s, 3H), 3.86 (s, 3H), 3.87 (s, 3H), 3.91 (s, 3H), 3.92 (s, 3H), 4.35 (q, J=5.0 Hz, 2H), 4.39 (q, J=5.0 Hz, 2H), 6.88-6.94 (m, 4H), 7.05 (s, 1H) and 7.75 (s, 1H); $^{13}$C NMR (acetone-$d_6$) δ 159.1, 159.0, 154.5, 154.2, 153.3, 142.5, 142.4, 139.4, 135.7, 127.0, 126.8, 126.7, 126.1, 125.3, 124.8, 120.9, 120.2, 118.5, 118.2, 107.5, 107.4, 105.2, 104.6, 60.7, 60.3, 60.2, 60.1, 60.0, 55.5, 55.4 and 13.7; Low res MS (DI, M+) 426, 428.

This solid mixture was subjected to flash chromatography on Biotage Isolera instrument with a silica column in which case 0.04 g (30% yield) of the cis isomer and 0.045 g (34% yield) of the trans isomer.

(cis-3-Bromo-4-(2,3,4-trimethoxyphenyl)-5-oximino-1H-pyrrole 2-carboxylic acid ethyl ester, NT-8-6-fr6/7) exhibited the following properties: m.p. 141-143° C.; $^1$H NMR (acetone-$d_6$) δ 1.39 (t, J=7.2 Hz, 3H), 3.64 (s, 3H), 3.86 (s, 3H), 3.91 (s, 3H), 4.39 (q, J=7.2 Hz, 2H), 6.87 (d, J=8.4 Hz, 1H), 6.93 (d, J=8.4 Hz, 1H), 7.03 (s, 1H); $^{13}$C NMR (acetone-$d_6$) δ 159.1, 154.2, 152.2, 142.4, 139.4, 127.0, 126.69, 124.7, 120.9, 118.4, 107.4, 105.2, 60.2, 60.1, 55.4, 13.7; IR (neat) 1710 cm$^{-1}$; HRMS (ES) m/z calcd for $C_{17}H_{19}NNaBrO_6$ 449.0319, 451.0301; found 449.0314, 451.0296.

(trans-3-Bromo-4-(2,3,4-trimethoxyphenyl)-5-oximino-1H-pyrrole 2-carboxylic acid ethyl ester, NT-8-6-fr8) exhibited the following properties: m.p. 125-126° C.; $^1$H NMR (acetone-$d_6$) δ 1.39 (t, J=7.2 Hz, 3H), 3.64 (s, 3H), 3.86 (s, 3H), 3.91 (s, 3H), 4.39 (q, J=7.2 Hz, 2H), 6.88 (d, J=8.4 Hz, 1H), 6.93 (d, J=8.4 Hz, 1H), 7.74 (s, 1H); $^{13}$C NMR (acetone-$d_6$) δ 159.1, 154.2, 152.2, 142.4, 139.4, 127.1, 126.7, 124.8, 121.0, 118.4, 107.5, 105.2, 60.3, 60.1, 55.4, 13.7; IR (neat) 1710 cm$^{-1}$; HRMS (ES) m/z calcd for $C_{17}H_{19}NNaBrO_6$ 449.0319, 451.0301; found 449.0313, 451.0297.

Example 11

3-Bromo-4-(2,3,4-trimethoxyphenyl)-5-cyano-1H-pyrrole 2-carboxylic acid ethyl ester (KL-3-95)

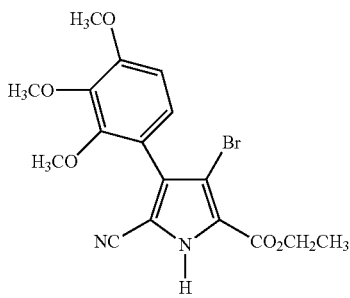

To a 100 mL round bottom flask equipped with a magnetic stir bar, was added 4-(2,3,4-trimethoxyphenyl)-5-oximino-1H-pyrrole-2-carboxylic acid ethyl ester (Ex. 10a, 0.100 g, 0.234 mmol) dissolved in 20 mL of anhydrous chloroform. The reaction mixture was allowed to cool in an ice bath for 5 minutes. Phosphorus oxychloride (0.036 g, 0.234 mmol) was dissolved in 10 mL of anhydrous chloroform and the resulting mixture was added dropwise to the reaction mixture. The reaction mixture was stirred in an ice bath for 30 minutes and overnight at room temperature. The reaction mixture was diluted with 30 mL of water. The organic layer was washed with water (3×25 mL) and brine (1x 15 mL), dried over anhydrous sodium sulfate, filtered, evaporated and dried to give a light brown solid. The crude product was purified using a s silica plug and eluting with 30 mL of hexane:ethyl acetate (1:1), evaporated and dried to give a golden solid (0.085 g, 89%). This solid exhibited the following properties: m.p. 173-176° C.; $^1$H NMR (CDCl$_3$) δ 1.45 (t, J=7.2 Hz, 3H), 3.83 (s, 3H), 3.93 (s, 6H), 4.45 (q, J=7.2 Hz, 2H), 6.75 (d, J=8.4 Hz, 1H), 6.97 (d, J=8.4 Hz, 1H); $^{13}$C NMR (CDCl$_3$) δ 159.2, 154.8, 152.0, 142.2, 133.0, 126.0, 124.2, 116.3, 111.9, 106.9, 104.9, 104.8, 62.1, 61.2, 61.2, 56.0, 14.2; IR (neat) 2221 and 1729 cm$^{-1}$; HRMS (ES, M+1) m/z calcd for $C_{17}H_{17}N_2O_5Br$, 409.0230 found 409.0283.

Example 12

Cis/Trans-3-Bromo-4-(2,3,4-trimethoxyphenyl)-5-(O-methyl-oximino)-1H-pyrrole-2-carboxylic acid ethyl ester (NT-7-46)

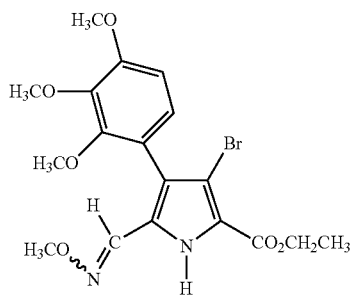

To a 100 mL round bottom flask equipped with a stir bar, was added 4-(2,3,4-trimethoxyphenyl)-5-formyl-1H-pyrrole 2-carboxylic cid ethyl ester (Ex. 2, 0.13 g, 0.315 mmol), methoxylamine hydrochloride (0.0260 g, 0.315 mmol), and 0.1 mL pyridine in 15 mL of ethanol. The reaction mixture was allowed to reflux for 2 hours. The reaction mixture was cooled and evaporated to give a crude residue. Water (10 mL) was added to the residue and the solution was cooled in an ice bath and stirred until the O-methyl-oxime crystallized. The solid was filtered and washed with water (2×15 mL) and dried to give a pale yellow solid (0.095 g, 71%). The crude residue was subjected to flash chromatography on Biotage Isolera instrument with a silica column in which case a mixture of cis/trans-isomers were obtained. This mixture of isomers exhibited the following properties: m.p. 125-128° C.; $^1$H NMR (acetone-$d_6$) δ 1.35-1.41 (m, 6H), 3.63 (s, 3H), 3.64 (s, 3H), 3.84 (s, 3H), 3.85 (s, 3H), 3.86 (s, 3H), 3.90 (s, 3H), 3.91 (s, 3H), 4.06 (s, 3H), 4.34-4.39 (m, 4H), 6.87-6.92 (m, 4H), 7.00 (s, 1H), 7.68 (s, 1H); IR (neat) 1707 cm$^{-1}$; HRMS (ES) m/z calcd for $C_{18}H_{21}BrN_2O_6$ 441.0656, 443.0638 found 441.0248, 443.0176.

Example 13

5-(Aminomethylene)-3-Bromo-4-(2,3,4-trimethoxyphenyl)-1H-pyrrole 2-carboxylic acid ethyl ester (NT-944)

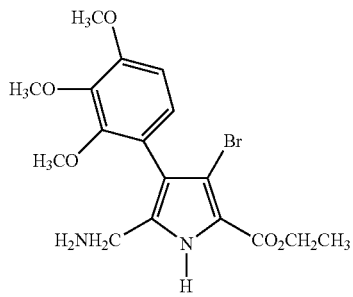

To a 100 mL round bottom flask equipped with a magnetic stir bar, was added 3-bromo-5-formyl-4-(2,3,4-trimethoxyphenyl)-1H-pyrrole 2-carboxylic acid ethyl ester (0.2 g, 0.48 mmol), and 1.0 M ammonia solution in dioxane (0.4 mL, 2.9 mmol) in 10 mL THF. The reaction mixture was stirred for 1 hour after which sodium cyanoborohydride (0.3 g, 1.44 mmol) and glacial acetic acid (0.5 mL) were added. The reaction mixture was stirred for 24 hours at room temperature after which the reaction mixture was diluted with 50 mL of water and was extracted with ethyl acetate (3×15 mL). The organic layers were combined, dried over anhydrous sodium sulfate and evaporated in vacuo. The crude product was dried using a Kulgelrohr apparatus to give 0.125 g of dark brown solid. The crude residue was subjected to flash chromatography on a Biotage SP-1 instrument with a silica column in which case 0.059 g (35%) of dark red solid was obtained upon elution with 9 column volumes of hexane/ethyl acetate gradient. This solid exhibited the following properties: m.p. 176-178° C.; $^1$H NMR (CDCl$_3$, 300 MHz) δ 1.41 (t, J=7.2 Hz, 3H), 3.73 (s, 3H), 3.91 (s, 3H), 3.93 (s, 3H), 3.50 (m, 2H), 4.41 (q, J=7.2 Hz, 2H), 6.74 (d, J=8.7 Hz, 1H), 6.87 (d, J=8.7 Hz, 1H); $^{13}$C NMR (CDCl$_3$, 75 MHz) δ 159.7, 154.0, 152.5, 142.1, 126.6, 124.4, 121.4, 118.6, 106.7, 105.8, 61.3, 61.1, 55.9, 14.2; IR (neat) 1686 cm$^{-1}$; HRMS (ES) m/z calcd for C$_{17}$H$_{21}$N$_2$BrO$_5$ [M+H]$^+$ 413.0707, 415.0688; found 413.0249, 415.0256.

Example 14

3-Chloro-5-(Aminomethylene)-4-(2,3,4-trimethoxyphenyl)-1H-pyrrole 2-carboxylic acid ethyl ester (NT-946)

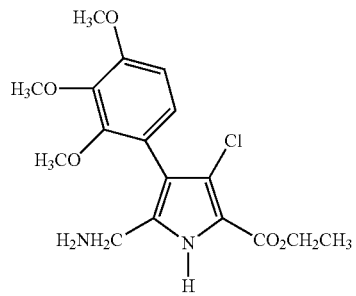

To a 100 mL round bottom flask equipped with a magnetic stir bar, was added 3-chloro-5-formyl-4-(2,3,4-trimethoxyphenyl)-1H-pyrrole 2-carboxylic acid ethyl ester (Ex. 3, 0.200 g, 0.544 mmol), and 1.0 M ammonia solution in dioxane (0.38 mL, 3.27 mmol) in 10 mL of THF. The reaction mixture was stirred for 1 hour after which sodium cyanoborohydride (0.6 g, 3.27 mmol) and glacial acetic acid (0.5 mL) were added. The reaction mixture was stirred for 24 hours at room temperature after which the reaction mixture was diluted with 50 mL water and was extracted with ethyl acetate (3×15 mL). The organic layers were combined, dried over anhydrous sodium sulfate and evaporated in vacuo. The crude product was dried using Kulgelrohr apparatus to give 0.142 g of dark brown solid. The crude residue was subjected to flash chromatography on a Biotage SP-1 instrument with a silica column in which case 0.072 g (36%) of dark red solid was obtained upon elution with 9 column volumes of hexane/ethyl acetate gradient. This solid exhibited the following properties: m.p. 143-145° C.; $^1$H NMR (CDCl$_3$, 300 MHz) δ 1.42 (t, J=7.2 Hz, 3H), 3.74 (s, 3H), 3.75 (m, 2H), 3.92 (s, 3H), 3.94 (s, 3H), 4.41 (q, J=7.2 Hz, 2H), 6.75 (d, J=8.7 Hz, 1H), 6.88 (d, J=8.7 Hz, 1H); $^{13}$C NMR (CDCl$_3$, 75 MHz) δ 159.8, 154.0, 152.6, 142.1, 126.6, 124.5, 121.4, 118.7, 106.8, 105.8, 61.3, 61.1, 55.9, 14.3; IR (neat) 1686 cm$^{-1}$; HRMS (ES) m/z calcd for C$_{17}$H$_{21}$N$_2$ClO$_5$ [M+H]$^+$ 369.1212, 371.1189; found 369.0933, 371.1039.

Example 15

3-Bromo-5-(Dimethylaminomethylene)-4-(2,3,4-trimethoxyphenyl)-1H-pyrrole 2-carboxylic acid ethyl ester (NT-9-43)

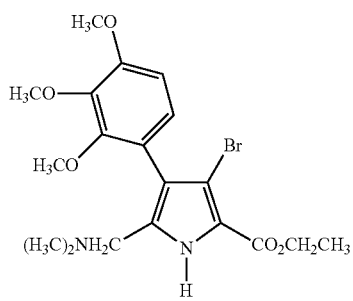

To a 100 mL round bottom flask equipped with a magnetic stir bar, was added 3-bromo-5-formyl-4-(2,3,4-trimethoxyphenyl)-1H-pyrrole 2-carboxylic acid ethyl ester (Ex. 2, 0.200 g, 0.64 mmol) and 1.0 M dimethylamine in THF (0.06 mL, 8.0 mmol) in 10 mL of THF. The reaction mixture was stirred for 1 hour after which sodium cyanoborohydride (0.35 g, 1.082 mmol) and glacial acetic acid (0.5 mL) were added. The reaction mixture was stirred for 24 hours at room temperature after which the reaction mixture was diluted with 50 mL water and was extracted with ethyl acetate (3×15 mL). The organic layers were combined, dried over anhydrous sodium sulfate and evaporated in vacuo. The crude product was dried using a Kulgelrohr apparatus to give 0.137 g of yellow solid. The crude residue was subjected to flash chromatography on a Biotage SP-1 instrument with a silica column in which case 0.210 g (30%) of pale yellow solid was obtained upon elution with 12 column volumes of hexane/ethyl acetate gradient. This solid exhibited the following properties: m.p. 163-165° C.; $^1$H NMR (CDCl$_3$, 300 MHz) δ 1.42 (t, J=7.2 Hz, 3H), 2.29 (s, 6H), 3.35 (d, J=15 Hz 1H), 3.60 (s, 3H), 3.64 (d, J=15 Hz 1H), 3.92 (s, 3H), 3.94 (s, 3H), 4.39 (q, J=7.2 Hz, 2H), 6.75 (d, J=8.7 Hz, 1H), 6.92 (d, J=8.7 Hz, 1H); $^{13}$C NMR (CDCl$_3$, 75 MHz) δ 159.9, 153.4, 152.0, 142.1, 130.3, 126.8, 122.1, 119.5, 119.2, 107.0, 104.9, 61.1, 60.9, 60.5, 55.8, 54.2, 44.4, 14.3; IR (neat) 1733 cm$^{-1}$; HRMS (ES) m/z calcd for C$_{19}$H$_{25}$N$_2$BrO$_5$ [M+H]$^+$ 441.1020, 443.1002; found 441.1141, 443.1059.

Example 16

3-Chloro-5-(Dimethylaminomethylene)-4-(2,3,4-trimethoxyphenyl)-1H-pyrrole 2-carboxylic acid ethyl ester (NT-9-49)

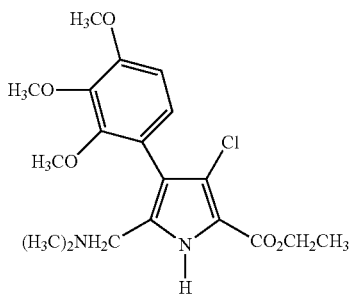

To a 100 mL round bottom flask equipped with a magnetic stir bar, was added 3-chloro-5-formyl-4-(2,3,4-trimethoxyphenyl)-1H-pyrrole 2-carboxylic acid ethyl ester (0.300 g, 0.81 mmol) and 1.0 M dimethylamine in THF (0.6 mL, 4.9 mmol) in 10 mL of THF. The reaction mixture was stirred for 1 hour after which sodium cyanoborohydride (1.00 g, 4.9 mmol) and glacial acetic acid (0.5 mL) were added. The reaction mixture was stirred for 24 hours at room temperature after which the reaction mixture was diluted with 50 mL water and was extracted with ethyl acetate (3×15 mL). The organic layers were combined, dried over anhydrous sodium sulfate and evaporated in vacuo. The crude product was dried using a Kulgelrohr apparatus to give 0.281 g of dark brown solid. The crude residue was subjected to flash chromatography on a Biotage SP-1 instrument with a silica column in which case 0.050 g (35%) of pale yellow solid was obtained upon elution with 9 column volumes of hexane/ethyl acetate gradient. This solid exhibited the following properties: m.p. 143-145° C.; $^1$H NMR (CDCl$_3$, 300 MHz) δ 1.41 (t, J=7.2 Hz, 3H), 2.41 (s, 6H), 3.58 (s, 3H), 3.61 (d, J=9.0 Hz 1H), 3.71 (d, J=9.0 Hz 1H), 3.90 (s, 3H), 3.91 (s, 3H), 4.36 (q, J=7.2 Hz, 2H), 6.74 (d, J=8.7 Hz, 1H), 6.88 (d, J=8.7 Hz, 1H); $^{13}$C NMR (CDCl$_3$, 75 MHz) δ 159.9, 153.4, 152.0, 142.1, 130.3, 126.8, 122.1, 119.5, 119.2, 107.0, 104.9, 61.0, 60.9, 60.5, 55.8, 54.2, 44.4, 14.3; IR (neat) 1691 cm$^{-1}$; HRMS (ES) m/z calcd for C$_{19}$H$_{25}$N$_2$ClO$_5$ [M+H]$^+$ 397.1525, 399.1503; found 397.2207, 399.2183.

Example 17

3-Bromo-5-(N-Propylaminomethylene)-4-(2,3,4-trimethoxyphenyl)-1H-pyrrole 2-carboxylic acid ethyl ester (NT-9-33)

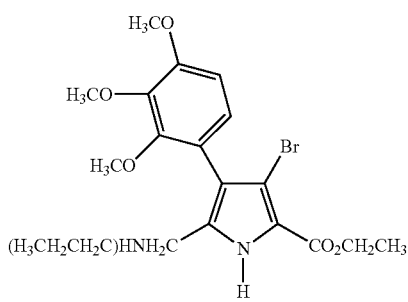

To a 100 mL round bottom flask equipped with a magnetic stir bar, was added 3-bromo-5-formyl-4-(2,3,4-trimethoxyphenyl)-1H-pyrrole 2-carboxylic acid ethyl ester (0.300 g, 0.73 mmol) and n-propyl amine (0.36 mL, 4.34 mmol) in 15 mL of THF. The reaction mixture was stirred for 1 hour after which sodium cyanoborohydride (0.068 g, 1.095 mmol) and glacial acetic acid (0.5 mL) were added. The reaction mixture was stirred for 24 hours at room temperature after which the reaction mixture was diluted with 50 mL of water and was extracted with ethyl acetate (3×15 mL). The organic layers were combined, dried over anhydrous sodium sulfate and evaporated in vacuo. The crude product was dried using a Kulgelrohr apparatus to give 0.356 g of dark brown solid. The crude residue was subjected to flash chromatography on a Biotage SP-1 instrument with a silica column in which case 0.25 g (76%) of a pale yellow solid was obtained upon elution with 19 column volumes of hexane/ethyl acetate gradient. This solid exhibited the following properties: m.p. 143-145° C.; $^1$H NMR (CDCl$_3$, 300 MHz) δ 0.91 (t, J=7.5 Hz, 3H), 1.41 (t, J=7.2 Hz, 3H), 1.49 (hex, J=7.5 Hz, 2H), 2.57 (t, J=7.8 Hz, 2H), 3.60 (s, 3H), 3.68 (m, 2H), 3.92 (s, 3H), 3.93 (s, 3H), 4.39 (q, J=7.2 Hz, 2H), 6.75 (d, J=8.7 Hz, 1H), 6.95 (d, J=8.7 Hz, 1H); $^{13}$C NMR (CDCl$_3$, 75 MHz) δ 160.1, 153.3, 152.3, 142.2, 126.9, 119.7, 118.7, 107.1, 104.9, 61.2, 61.1, 60.5, 55.9, 51.3, 44.93, 22.4, 14.4, 11.6; IR (neat) 1727 cm$^{-1}$; HRMS (ES) m/z calcd for C$_{20}$H$_{29}$N$_2$BrO$_5$ [M+Na]$^+$ 479.1152, 481.1134; found 479.1837, 481.2068.

Example 18

3-Chloro-5-(N-Propylaminomethylene)-4-(2,3,4-Trimethoxyphenyl)-1H-pyrrole 2-carboxylic acid ethyl ester [NT-9-37(2)]

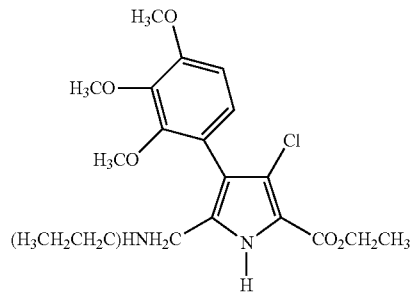

To a 100 mL round bottom flask equipped with a magnetic stir bar, was added 3-chloro-5-formyl-4-(2,3,4-trimethoxyphenyl)-1H-pyrrole 2-carboxylic acid ethyl ester (0.250 g, 0.68 mmol) and n-propyl amine (0.33 mL, 4.0 mmol) in 20 mL of THF. The reaction mixture was stirred for 1 hour after which sodium cyanoborohydride (0.128 g, 2.04 mmol) and glacial acetic acid (0.5 mL) were added. The reaction mixture was stirred for 24 hours at room temperature after which the reaction mixture was diluted with 50 mL water and was extracted with ethyl acetate (3×15 mL). The organic layers were combined, dried over anhydrous sodium sulfate and evaporated in vacuo. The crude product was dried using a Kulgelrohr apparatus to give 0.316 g of dark brown solid. The crude residue was subjected to flash chromatography on a Biotage SP-1 instrument with a silica column in which case 0.21 g (75%) of pale yellow solid was obtained upon elution with 10 column volumes of hexane/ethyl acetate gradient. This solid exhibited the following properties: m.p.

166-168° C.; $^1$H NMR (CDCl$_3$, 300 MHz) δ 0.93 (t, J=7.5 Hz, 3H), 1.42 (t, J=7.2 Hz, 3H), 1.50 (hex, J=7.5 Hz, 2H), 2.57 (m, 2H), 3.61 (s, 3H), 3.63 (m, 2H), 3.93 (s, 3H), 3.94 (s, 3H), 4.39 (q, J=7.2 Hz, 2H), 6.76 (d, J=8.7 Hz, 1H), 6.96 (d, J=8.7 Hz, 1H); $^{13}$C NMR (CDCl$_3$, 75 MHz) δ 160.2, 153.4, 152.2, 142.2, 126.9, 119.5, 118.8, 107.1, 105.0, 61.2, 61.1, 60.5, 55.9, 51.2, 45.0, 22.5, 14.4, 11.6; IR (neat) 1727 cm$^{-1}$; HRMS (ES) m/z calcd for C$_{20}$H$_{27}$N$_2$ClO$_5$ [M]$^+$ 410.1603, 412.1582; found 410.0352, 412.0443.

Example 19

3-Bromo-5-[((N-2-tert-butoxycarbonylamino)-ethyl-amino)-methyl]-4-(2,3,4-trimethoxyphenyl)-1H-pyrrole 2-carboxylic acid ethyl ester (NT-9-56)

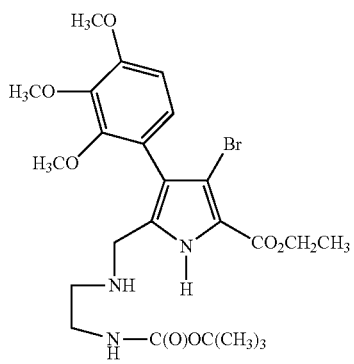

To a 100 mL round bottom flask equipped with a magnetic stir bar, was added 3-bromo-5-formyl-4-(2,3,4-trimethoxyphenyl)-1H-pyrrole 2-carboxylic acid ethyl ester (0.350 g, 0.850 mmol) and N-Boc-ethylenediamine (0.3 mL, 5.00 mmol) in 15 mL of THF. The reaction mixture was stirred for 1 hour after which sodium cyanoborohydride (1.055 g, 5.0 mmol) and glacial acetic acid (0.5 mL) were added. The reaction mixture was stirred for 24 hours at room temperature after which the reaction mixture was diluted with 50 mL of water and extracted with ethyl acetate (3×15 mL). The organic layers were combined, dried over anhydrous sodium sulfate and evaporated in vacuo. The crude product was dried using a Kulgelrohr apparatus to give 0.436 g (93%) of a tacky beige solid. The crude residue was subjected to flash chromatography on a Biotage SP-1 instrument with a silica column in which case 0.310 g (66%) of a beige solid was obtained upon elution with 28 column volumes of hexane/ethyl acetate gradient, having the following properties: m.p. 235-237° C.; $^1$H NMR (CDCl$_3$, 300 MHz) δ 1.42 (broad m, 12H), 2.70 (broad s, 2H), 3.23 (broad s, 2H), 3.62 (broad m, 4H), 3.94, (s, 3H), 3.95 (s, 3H), 4.36 (q, J=7.2 Hz, 2H), 6.76 (d, J=8.7 Hz, 1H) and 6.92 (d, J=8.7 Hz, 1H); $^{13}$C NMR (CDCl$_3$, 75 MHz) δ 161.0, 156.5, 153.3, 152.1, 142.1, 133.4, 127.2, 121.1, 119.6, 119.2, 107.3, 104.9, 79.2, 61.3, 60.8, 55.9, 49.0, 44.9, 39.8, 28.3 and 14.4; IR (neat) 1655 cm$^{-1}$; HRMS (ES, M+H) m/z calcd for C$_{24}$H$_{34}$N$_3$O$_7$Br, 556.1653 found 556.1640.

Example 20

5-[N-((2-Aminoethyl)amino)methyl]-3-Bromo-4-(2,3,4-trimethoxyphenyl)-1H-pyrrole 2-carboxylic acid ethyl ester (NT-9-62)

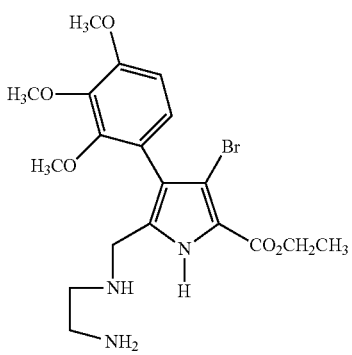

To a 100 mL round bottom flask equipped with a magnetic stir bar, was added 3-bromo-5-[((N-2-tert-butoxycarbonylamino)ethylamino)-methyl]-4-trimethoxyphenyl)-1H-pyrrole-2-carboxylic acid ethyl ester (Ex. 19, 0.310 g, 0.540 mmol), 2M HCl in dioxane (3.5 mL, 2.7 mmol) and 10 mL of dichloromethane. The reaction mixture was stirred for 24 hours at room temperature after which the reaction mixture was diluted with 15 mL of sodium bicarbonate solution (until the solution turned basic) and was then extracted with dichloromethane (3×15 mL). The organic layers were combined, dried over anhydrous sodium sulfate, filtered, and evaporated in vacuo. The crude product was dried using a Kulgelrohr apparatus to give 0.210 g (82%) of a pale orange solid. m.p. 135-137° C.; $^1$H NMR (MeOH-d$_4$, 300 MHz) δ 1.38 (t, J=7.2 Hz), 3.34 (m, 4H), 3.58 (m, 4H), 3.59 (m, 1H), 3.61 (s, 3H), 3.62 (s, 3H), 4.34 (q, J=7.2 Hz, 2H), 6.84 (d, J=9.0 Hz, 1H) and 6.90 (d, J=9.0 Hz, 1H); $^{13}$C NMR (DMSO-d$_6$, 75 MHz) δ 162.8, 159.9, 153.5, 152.3, 142.1, 127.2, 121.4, 119.9, 118.2, 107.9, 104.8, 61.0, 60.2, 56.2, 40.8, 36.2, 29.5 and 14.9; IR (neat) 1656 cm$^{-1}$; HRMS (ES, M+H) m/z calcd for C$_{19}$H$_{26}$N$_3$O$_5$Br, 456.1129 found 456.1249.

Example 21

Cis/Trans-3-chloro-4-(2, 3,4-trimethoxyphenyl)-5-oximino-1H-pyrrole 2-carboxylic acid ethyl ester (NT-9-24)

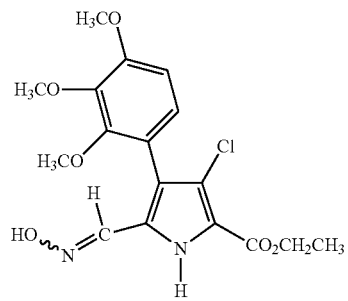

To a 100 mL round bottom flask equipped with a stir bar, was added 3-chloro-4-(2,3,4-trimethoxyphenyl)-5-formyl-1H-pyrrole 2-carboxylic acid ethyl ester (0.130 g, 0.315 mmol), hydroxyl amine hydrochloride (0.05 g, 0.63 mmol), 0.1 mL pyridine in 15 mL of ethanol. The reaction mixture was allowed to reflux with stirring for 2 hours. The reaction mixture was cooled and evaporated to give a crude residue. Water (10 mL) was added to the residue and the solution was cooled in an ice bath and stirred until the oxime crystallized. The solid was filtered and washed with water (2×15 mL) and dried to give an orange solid (0.122 g). The crude residue was subjected to flash chromatography on Biotage Isolera instrument with a silica column in which case 0.083 g (69%) of a pale yellow solid (mixture of isomers) was obtained upon elution with 5 column volumes of hexane/ethyl acetate gradient. This mixture of isomers exhibited the following properties: m.p. 135-140° C.; $^1$H NMR (acetone-$d_6$) δ 1.35-1.41 (m, 6H), 3.66 (s, 3H), 3.67 (s, 3H), 3.86 (s, 3H), 3.87 (s, 3H), 3.89 (s, 3H), 3.90 (s, 3H), 3.91 (s, 3H), 4.34-4.39 (m, 4H), 6.83-6.92 (m, 4H), 7.06 (s, 1H), 7.75 (s, 1H); IR (neat) 1729 and 1675 cm$^{-1}$; HRMS (ES, M+Na) m/z calcd for $C_{17}H_{19}N_2O_6Cl$, 405.0824 found 405.0898.

Example 22

3,5-Dibromo-4-(2,3,4-trimethoxyphenyl)-1H-pyrrole-2-carboxylic acid ethyl ester (NT-7-16)

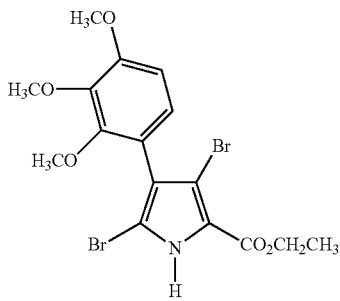

To a 100 mL round bottom flask equipped with a magnetic stirring bar, thermometer, reflux condenser and addition funnel, was added 15 mL of dry DMF, which was immediately cooled to 0-5° C. Phosphorous oxychloride (2.4 ml, 26.5 mmol) was added dropwise via the addition funnel while the reaction temperature was controlled between 10-15° C. with an ice bath. The reaction mixture was then cooled to 0-5° C. and 2,3,4-trimethoxyphenyl acetic acid (2.000 g) was added to the reaction mixture in small portions. After removal of the cooling bath, the reaction mixture was heated at 75-80° C. for 2 hours while ensuring that the reaction temperature never exceeded 90° C. The reaction mixture was then cooled to 30° C. and ~100 g of ice was carefully added to the flask. After the ice had melted, the reaction mixture was poured into a solution of sodium hexafluorophosphate (4.79 g in 100 mL of water) with stirring in which case an orange solid precipitated. The solid was filtered and dried in vacuo to give [3-dimethylamino-2-(2,3,4-trimethoxyphenyl)-allylidene]dimethyl-ammonium hexafluorophosphate as an orange solid (3.300 g, 86% yield), which exhibited the following physical properties: mp 234-236° C.; $^1$H NMR (CDCl$_3$) d 3.4 (s, 12H), 3.9 (s, 3H), 4.2 (s, 6H), 7.0 (s, 2H) and 9.8 (s, 2H); $^{13}$C NMR (CDCl$_3$) 191.5, 165.6, 157.3, 147.2, 140.3, 138.1, 126.5, 120.5, 113.7, 88.7, 60.9, 56.7, 47.6 and 43.4; IR (neat) 1589 cm$^{-1}$; High Resolution MS (IT-TOF) m/z calcd for $C_{16}H_{25}N_2O_3^+$ 293.1860 found 293.1880.

To a 100 mL 3 neck round bottom flask equipped with a magnetic stir bar, was added sodium hydride (0.219 g, 9.1 mmol), t-butanol (2.6 mL, 13.68 mmol) in 30 mL DMF and stirred till effervescence ceases. 2,3,4-Trimethoxyphenyl vinamidinium salt (1.0 g, 2.28 mmol) and ethyl glycine ester hydrochloride (0.954 g, 6.84 mmol) were then added to the reaction mixture. The reaction mixture was refluxed for 24 hours. The reaction mixture was allowed to cool at room temperature and was diluted with 100 mL water. The aqueous solution was extracted with (2×50 mL) ethyl acetate. The organic extract was subsequently washed with water (2×50 mL), brine (2×50 mL) and dried over anhydrous sodium sulfate and evaporated in vacuo. The crude residue was further dried using Kugelrohr apparatus to give a reddish brown solid (0.327 g, 94%). The crude residue was subjected to flash chromatography on a Biotage Isolera instrument with a silica column in which case 0.431 g (62% yield) of 4-(2,3,4-trimethoxyphenyl)-1H-pyrrole-2-carboxylic acid ethyl ester as a pale yellow solid was obtained upon elution with seven column volumes of hexane/ethyl acetate gradient. This solid exhibited the following properties: mp 163-165° C.; $^1$H NMR (acetone-$d_6$) δ 1.39 (t, J=7.0 Hz, 3H), 3.84 (s, 3H), 3.89 (s, 3H), 3.93 (s, 3H), 4.36 (q, J=7.0 Hz, 2H), 6.71 (d, J=8.7 Hz, 1H), 7.20 (d, J=8.7 Hz, 1H), 7.22-7.33 (m, 1H), 7.41-7.42 (m, 1H); $^{13}$C NMR (acetone-$d_6$) δ 161.3, 152.2, 150.9, 142.9, 122.7, 122.2, 122.1, 121.8, 121.6, 113.8, 107.9, 60.9, 60.4, 60.2, 56.1, 14.4; IR (neat) 1712 cm$^{-1}$; High resolution MS (IT-TOF) m/z calcd for $C_{16}H_{20}NO_5$ 306.1336, found 306.1316.

To a 100 mL round bottom flask equipped with a stir bar, was added 4-(2,3,4-trimethoxyphenyl)-1H-pyrrole-2-carboxylic acid ethyl ester (0.25 g, 0.82 mmol) and potassium hydroxide (0.184 g, 3.27 mmol) in 25 mL DMF. The reaction mixture was allowed to stir for 15 minutes at room temperature, after which pyridinium tribromide (0.524 g, 1.63 mmol) was added and the reaction mixture was stirred overnight at room temperature. The reaction mixture was diluted with 50 mL water and 15 mL of sodium thiosulfate solution was added. It was extracted with ethyl acetate (3×15 mL). The combined ethyl acetate layers were dried over anhydrous sodium sulfate, filtered and concentrated to give an orange solid (0.315 g, 83.5%). The crude residue was subjected to flash chromatography on a Biotage SP-1 instrument with a silica column in which case 0.295 g (78% yield) of 3,5-dibromo-4-(2,3,4-trimethoxyphenyl)-1H-pyrrole-2-carboxylic acid ethyl ester as a tan solid was obtained upon elution with five column volumes of hexane/ethyl acetate gradient. This solid exhibited the following properties: mp 203-205° C.; $^1$H NMR (CDCl$_3$) δ 1.33 (t, J=7.2 Hz, 3H), 3.68 (s, 3H), 3.84 (s, 3H), 3.87 (s, 3H), 4.35 (q, J=7.2 Hz, 2H), 6.68 (d, J=8.4 Hz, 1H), 6.82 (d, J=8.4 Hz, 1H); $^{13}$C NMR (CDCl$_3$) δ 160.2, 154.0, 152.5, 142.1, 126.7, 124.2, 121.4, 118.8, 106.8, 106.3, 105.7, 61.3, 61.2, 61.0, 55.8, 14.3; IR (neat) 1708 cm$^{-1}$; High Resolution MS (IT-TOF) m/z calcd for $C_{16}H_{17}NNaBr_2O_5$ 483.9366, 485.9346 found 483.9356, 485.9337.

Example 23

3,5-Dichloro-4-(2,3,4-Trimethoxyphenyl)-1H-pyrrole-2-carboxylic acid ethyl ester (NT-9-21)

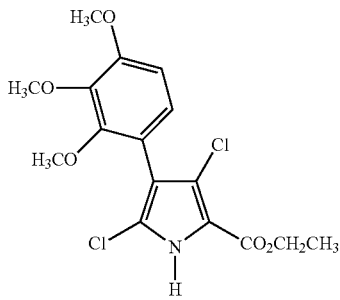

To a 100 mL round bottom flask equipped with a stir bar, was added 4-(2,3,4-trimethoxyphenyl)-1H-pyrrole-2-carboxylic acid ethyl ester (0.25 g, 0.82 mmol) and potassium hydroxide (0.184 g, 3.27 mmol) in 25 mL DMF. The reaction mixture was allowed to stir for 15 minutes at room temperature, after which N-chlorosuccinimide (0.214 g, 1.63 mmol) was added and the reaction mixture was stirred overnight at room temperature. The reaction mixture was diluted with 50 mL water and 15 mL of sodium thiosulfate solution was added. It was extracted with ethyl acetate (3×15 mL). The combined ethyl acetate layers were dried over anhydrous sodium sulfate, filtered and concentrated to give a dark orange solid (0.323 g, 87%). The crude residue was subjected to flash chromatography on a Biotage Isolera instrument with a silica column in which case 0.256 g (69%) of 3,5-dichloro-4-(2,3,4-trimethoxyphenyl)-1H-pyrrole-2-carboxylic acid ethyl ester as an orange solid was obtained upon elution with seven column volumes of hexane/ethyl acetate gradient. This solid exhibited the following properties: m. p. 151-153° C.; $^1$H NMR (CDCl$_3$) δ 1.42 (t, J=7.2 Hz, 3H), 3.74 (s, 3H), 3.92 (s, 3H), 3.94 (s, 3H), 4.42 (q, J=7.2 Hz, 2H), 6.74 (d, J=8.4 Hz, 1H), 6.87 (d, J=8.4 Hz, 1H); $^{13}$C NMR (CDCl$_3$) δ 159.9, 152.8, 137.5, 127.2, 126.6, 121.8, 107.4, 104.7, 103.8, 61.4, 60.9, 56.1, 31.1, 14.3; IR (neat) 1671 cm$^{-1}$; High Resolution MS (IT-TOF) m/z calcd for $C_{16}H_{18}NCl_2O_5$ 374.0557 found 374.0641.

Using the preceding methods, additional unsymmetrical 3,5-disubstituted 4-[2,3,4-tri-methoxyphenyl)pyrrole 2-carboxylic acids, unsymmetrical 3,5-disubstituted 4-[2,3,4-tri-methoxyphenyl)pyrrole 2-carboxylic acid esters and unsymmetrical 3,5-disubstituted 2-cyano-4-[2,3,4-trimethoxyphenyl)pyrroles can be prepared by one skilled in the art using similar methods, as shown in Example Tables 1 through 41 below.

Using the preceding methods, additional substituted 3,5-dihalo-4-[2,3,4-trimethoxy-phenyl)pyrrole-2-carboxylic acids and 2-carboxylic acid esters and 2-cyano-3,5-dihalo-4-[2,3,4-trimethoxy-phenyl)-pyrroles, and 2-substituted 3,5-dihalo-4-[2,3,4-trimethoxy-phenyl)pyrroles and 2-cyano-3,5-dihalo-4-[2,3,4-trimethoxy-phenyl)pyrroles and N-substituted 3,5-dihalo-4-[2,3,4-trimethoxyphenyl)pyrrole-2-carboxylic acid esters and N-substituted 2-cyano-3,5-dihalo-4-[2,3,4-trimethoxy-phenyl)-pyrroles can be prepared by one skilled in the art using similar methods, as shown in Tables 42 through 47.

TABLE 1

Unsymmetrical 5-Aminomethyl-3-halo-4-[2,3,4-Trimethoxyphenyl)-pyrrole 2-carboxylic acid esters, Unsymmetrical 5-Aminomethyl-3-halo-4-[2,3,4-Tri-methoxy-phenyl)pyrrole 2-carboxylic acids, and Unsymmetrical 2-Cyano-5-Amino-methyl-3-halo-4-[2,3,4-Trimethoxy-phenyl)pyrroles.

| Ex. No. | Structure |
|---|---|
| 30A | 3-Cl, CO$_2$CH$_3$ pyrrole with 5-CH$_2$NH$_2$ and 4-(2,3,4-trimethoxyphenyl) |
| 30B | 3-Br, CO$_2$CH$_3$ pyrrole with 5-CH$_2$NH$_2$ and 4-(2,3,4-trimethoxyphenyl) |
| 31A | 3-Cl, CO$_2$—n-Pr pyrrole with 5-CH$_2$NH$_2$ and 4-(2,3,4-trimethoxyphenyl) |
| 31B | 3-Br, CO$_2$—n-Pr pyrrole with 5-CH$_2$NH$_2$ and 4-(2,3,4-trimethoxyphenyl) |
| 32A | 3-Cl, CO$_2$CH(CH$_3$)$_2$ pyrrole with 5-CH$_2$NH$_2$ and 4-(2,3,4-trimethoxyphenyl) |

TABLE 1-continued

Unsymmetrical 5-Aminomethyl-3-halo-4-[2,3,4-Trimethoxyphenyl)-pyrrole 2-carboxylic acid esters, Unsymmetrical 5-Aminomethyl-3-halo-4-[2,3,4-Tri-methoxy-phenyl)pyrrole 2-carboxylic acids, and Unsymmetrical 2-Cyano-5-Amino-methyl-3-halo-4-[2,3,4-Trimethoxy-phenyl)pyrroles.

| Ex. No. | Structure |
|---|---|
| 32B | (structure: 3-bromo-4-(2,3,4-trimethoxyphenyl)-5-(aminomethyl)pyrrole-2-carboxylic acid isopropyl ester, CO₂CH(CH₃)₂) |
| 33A | (structure: 3-chloro-4-(2,3,4-trimethoxyphenyl)-5-(aminomethyl)pyrrole-2-carbonitrile, C≡N) |
| 33B | (structure: 3-bromo-4-(2,3,4-trimethoxyphenyl)-5-(aminomethyl)pyrrole-2-carbonitrile, C≡N) |
| 34A | (structure: 3-chloro-4-(2,3,4-trimethoxyphenyl)-5-(aminomethyl)pyrrole-2-carboxylic acid, CO₂H) |
| 34B | (structure: 3-bromo-4-(2,3,4-trimethoxyphenyl)-5-(aminomethyl)pyrrole-2-carboxylic acid, CO₂H) |

TABLE 2

Unsymmetrical 5-Aminoethyl-3-halo-4-[2,3,4-Trimethoxyphenyl)-pyrrole 2-carboxylic acid esters, Unsymmetrical 5-Aminoethyl-3-halo-4-[2,3,4-Tri-methoxyphenyl)pyrrole 2-carboxylic acids, and Unsymmetrical 2-Cyano-5-Aminoethyl-3-halo-4-[2,3,4-Trimethoxyphenyl)pyrroles.

| Ex. No. | Structure |
|---|---|
| 35A | (structure: 3-chloro-4-(2,3,4-trimethoxyphenyl)-5-(2-aminoethyl)pyrrole-2-carboxylic acid methyl ester, H₂NH₂CH₂C—, CO₂CH₃) |
| 35B | (structure: 3-bromo-4-(2,3,4-trimethoxyphenyl)-5-(2-aminoethyl)pyrrole-2-carboxylic acid methyl ester, CO₂CH₃) |
| 36A | (structure: 3-chloro-4-(2,3,4-trimethoxyphenyl)-5-(2-aminoethyl)pyrrole-2-carboxylic acid ethyl ester, CO₂CH₂CH₃) |
| 36B | (structure: 3-bromo-4-(2,3,4-trimethoxyphenyl)-5-(2-aminoethyl)pyrrole-2-carboxylic acid ethyl ester, CO₂CH₂CH₃) |
| 37A | (structure: 3-chloro-4-(2,3,4-trimethoxyphenyl)-5-(2-aminoethyl)pyrrole-2-carboxylic acid n-propyl ester, CO₂—n-Pr) |

TABLE 2-continued

Unsymmetrical 5-Aminoethyl-3-halo-4-[2,3,4-Trimethoxyphenyl)-pyrrole 2-carboxylic acid esters, Unsymmetrical 5-Aminoethyl-3-halo-4-[2,3,4-Trimethoxyphenyl)pyrrole 2-carboxylic acids, and Unsymmetrical 2-Cyano-5-Aminoethyl-3-halo-4-[2,3,4-Trimethoxyphenyl)pyrroles.

| Ex. No. | Structure |
|---|---|
| 37B | 4-(2,3,4-trimethoxyphenyl)-3-Br-5-(H$_2$NCH$_2$CH$_2$)-pyrrole-2-CO$_2$-n-Pr |
| 38A | 4-(2,3,4-trimethoxyphenyl)-3-Cl-5-(H$_2$NCH$_2$CH$_2$)-pyrrole-2-CN |
| 38B | 4-(2,3,4-trimethoxyphenyl)-3-Br-5-(H$_2$NCH$_2$CH$_2$)-pyrrole-2-CN |
| 39A | 4-(2,3,4-trimethoxyphenyl)-3-Cl-5-(H$_2$NCH$_2$CH$_2$)-pyrrole-2-CO$_2$H |
| 39B | 4-(2,3,4-trimethoxyphenyl)-3-Br-5-(H$_2$NCH$_2$CH$_2$)-pyrrole-2-CO$_2$H |

TABLE 3

Unsymmetrical 5-Aminopropyl-3-halo-4-[2,3,4-Trimethoxyphenyl)-pyrrole 2-carboxylic acid esters, Unsymmetrical 5-Aminopropyl-3-halo-4-[2,3,4-Trimethoxyphenyl)pyrrole 2-carboxylic acids, and Unsymmetrical 2-Cyano-5-Amino-propyl-3-halo-4-[2,3,4-Trimethoxyphenyl)pyrroles.

| Ex. No. | Structure |
|---|---|
| 40A | 4-(2,3,4-trimethoxyphenyl)-3-Cl-5-(H$_2$N(H$_2$C)$_3$)-pyrrole-2-CO$_2$CH$_3$ |
| 40B | 4-(2,3,4-trimethoxyphenyl)-3-Br-5-(H$_2$N(H$_2$C)$_3$)-pyrrole-2-CO$_2$CH$_3$ |
| 41A | 4-(2,3,4-trimethoxyphenyl)-3-Cl-5-(H$_2$N(H$_2$C)$_3$)-pyrrole-2-CO$_2$CH$_2$CH$_3$ |
| 41B | 4-(2,3,4-trimethoxyphenyl)-3-Br-5-(H$_2$N(H$_2$C)$_3$)-pyrrole-2-CO$_2$CH$_2$CH$_3$ |
| 42A | 4-(2,3,4-trimethoxyphenyl)-3-Cl-5-(H$_2$N(H$_2$C)$_3$)-pyrrole-2-CO$_2$-n-Pr |

TABLE 3-continued

Unsymmetrical 5-Aminopropyl-3-halo-4-[2,3,4-Trimethoxyphenyl)-pyrrole 2-carboxylic acid esters, Unsymmetrical 5-Aminopropyl-3-halo-4-[2,3,4-Trimethoxyphenyl)pyrrole 2-carboxylic acids, and Unsymmetrical 2-Cyano-5-Amino-propyl-3-halo-4-[2,3,4-Trimethoxyphenyl)pyrroles.

| Ex. No. | Structure |
|---|---|
| 42B | 3,4-trimethoxyphenyl-3-Br-pyrrole, 5-(CH$_2$)$_3$NH$_2$, 2-CO$_2$-n-Pr |
| 43A | 3,4-trimethoxyphenyl-3-Cl-pyrrole, 5-(CH$_2$)$_3$NH$_2$, 2-CN |
| 43B | 3,4-trimethoxyphenyl-3-Br-pyrrole, 5-(CH$_2$)$_3$NH$_2$, 2-CN |
| 44A | 3,4-trimethoxyphenyl-3-Cl-pyrrole, 5-(CH$_2$)$_3$NH$_2$, 2-CO$_2$H |
| 44B | 3,4-trimethoxyphenyl-3-Br-pyrrole, 5-(CH$_2$)$_3$NH$_2$, 2-CO$_2$H |

TABLE 4

Unsymmetrical 5-Aminobutyl-3-halo-4-[2,3,4-Trimethoxyphenyl)-pyrrole 2-carboxylic acid esters, Unsymmetrical 5-Aminobutyl-3-halo-4-[2,3,4-Trimethoxyphenyl)pyrrole 2-carboxylic acids, and Unsymmetrical 2-Cyano-5-Amino-butyl-3-halo-4-[2,3,4-Trimethoxyphenyl)pyrroles.

| Ex. No. | Structure |
|---|---|
| 45A | 3,4-trimethoxyphenyl-3-Cl-pyrrole, 5-(CH$_2$)$_4$NH$_2$, 2-CO$_2$CH$_3$ |
| 45B | 3,4-trimethoxyphenyl-3-Br-pyrrole, 5-(CH$_2$)$_4$NH$_2$, 2-CO$_2$CH$_3$ |
| 46A | 3,4-trimethoxyphenyl-3-Cl-pyrrole, 5-(CH$_2$)$_4$NH$_2$, 2-CO$_2$CH$_2$CH$_3$ |
| 46B | 3,4-trimethoxyphenyl-3-Br-pyrrole, 5-(CH$_2$)$_4$NH$_2$, 2-CO$_2$CH$_2$CH$_3$ |
| 47A | 3,4-trimethoxyphenyl-3-Cl-pyrrole, 5-(CH$_2$)$_4$NH$_2$, 2-CO$_2$-n-Pr |

TABLE 4-continued

Unsymmetrical 5-Aminobutyl-3-halo-4-[2,3,4-Trimethoxyphenyl)-pyrrole 2-carboxylic acid esters, Unsymmetrical 5-Aminobutyl-3-halo-4-[2,3,4-Trimethoxyphenyl)pyrrole 2-carboxylic acids, and Unsymmetrical 2-Cyano-5-Amino-butyl-3-halo-4-[2,3,4-Trimethoxyphenyl)pyrroles.

| Ex. No. | Structure |
|---|---|
| 47B | (structure) |
| 48A | (structure) |
| 48B | (structure) |
| 49A | (structure) |
| 49B | (structure) |

TABLE 5

Unsymmetrical 5-[(N-Methyl)-Aminomethyl]-3-halo-4-[2,3,4-Trimethoxyphenyl)-pyrrole 2-carboxylic acid esters, Unsymmetrical 5-[(N-Methyl)-Aminomethyl]-3-halo-4-[2,3,4-Trimethoxyphenyl)pyrrole 2-carboxylic acids, and Unsymmetrical 2-Cyano-5-[(N-Methyl)-Aminomethyl]-3-halo-4-[2,3,4-Trimethoxy-phenyl)pyrroles.

| Ex. No. | Structure |
|---|---|
| 50A | (structure) |
| 50B | (structure) |
| 51A | (structure) |
| 51B | (structure) |
| 52A | (structure) |

TABLE 5-continued

Unsymmetrical 5-[(N-Methyl)-Aminomethyl]-3-halo-4-[2,3,4-Trimethoxyphenyl)-pyrrole 2-carboxylic acid esters, Unsymmetrical 5-[(N-Methyl)-Aminomethyl]-3-halo-4-[2,3,4-Trimethoxyphenyl)pyrrole 2-carboxylic acids, and Unsymmetrical 2-Cyano-5-[(N-Methyl)-Aminomethyl]-3-halo-4-[2,3,4-Trimethoxy-phenyl)pyrroles.

| Ex. No. | Structure |
|---|---|
| 52B | 3-Br, 2-CO₂-n-Pr, 5-CH₂NH(CH₃), 4-(2,3,4-trimethoxyphenyl)pyrrole |
| 53A | 3-Cl, 2-CN, 5-CH₂NH(CH₃), 4-(2,3,4-trimethoxyphenyl)pyrrole |
| 53B | 3-Br, 2-CN, 5-CH₂NH(CH₃), 4-(2,3,4-trimethoxyphenyl)pyrrole |
| 54A | 3-Cl, 2-CO₂H, 5-CH₂NH(CH₃), 4-(2,3,4-trimethoxyphenyl)pyrrole |
| 54B | 3-Br, 2-CO₂H, 5-CH₂NH(CH₃), 4-(2,3,4-trimethoxyphenyl)pyrrole |

TABLE 6

Unsymmetrical 5-[(N-Ethyl)-Aminomethyl]-3-halo-4-[2,3,4-Trimethoxyphenyl)-pyrrole 2-carboxylic acid esters, Unsymmetrical 5-[(N-Ethyl)-Aminomethyl]-3-halo-4-[2,3,4-Trimethoxyphenyl)pyrrole 2-carboxylic acids, and Unsymmetrical 2-Cyano-5-[(N-Ethyl)-Aminomethyl]-3-halo-4-[2,3,4-Trimethoxy-phenyl)pyrroles.

| Ex. No. | Structure |
|---|---|
| 55A | 3-Cl, 2-CO₂CH₃, 5-CH₂NH(CH₂CH₃), 4-(2,3,4-trimethoxyphenyl)pyrrole |
| 55B | 3-Br, 2-CO₂CH₃, 5-CH₂NH(CH₂CH₃), 4-(2,3,4-trimethoxyphenyl)pyrrole |
| 56A | 3-Cl, 2-CO₂CH₂CH₃, 5-CH₂NH(CH₂CH₃), 4-(2,3,4-trimethoxyphenyl)pyrrole |
| 56B | 3-Br, 2-CO₂CH₂CH₃, 5-CH₂NH(CH₂CH₃), 4-(2,3,4-trimethoxyphenyl)pyrrole |
| 57A | 3-Cl, 2-CO₂-n-Pr, 5-CH₂NH(CH₂CH₃), 4-(2,3,4-trimethoxyphenyl)pyrrole |

TABLE 6-continued

Unsymmetrical 5-[(N-Ethyl)-Aminomethyl]-3-halo-4-[2,3,4-Trimethoxyphenyl)-pyrrole 2-carboxylic acid esters, Unsymmetrical 5-[(N-Ethyl)-Aminomethyl]-3-halo-4-[2,3,4-Trimethoxyphenyl)pyrrole 2-carboxylic acids, and Unsymmetrical 2-Cyano-5-[(N-Ethyl)-Aminomethyl]-3-halo-4-[2,3,4-Trimethoxy-phenyl)pyrroles.

| Ex. No. | Structure |
|---|---|
| 57B | [structure] |
| 58A | [structure] |
| 58B | [structure] |
| 59A | [structure] |
| 59B | [structure] |

TABLE 7

Unsymmetrical 5-[(N-Propyl)-Aminomethyl]-3-halo-4-[2,3,4-Trimethoxyphenyl)-pyrrole 2-carboxylic acid esters, Unsymmetrical 5-[(N-Propyl)-Aminomethyl]-3-halo-4-[2,3,4-Trimethoxyphenyl)pyrrole 2-carboxylic acids, and Unsymmetrical 2-Cyano-5-[(N-Propyl)-Aminomethyl]-3-halo-4-[2,3,4-Trimethoxy-phenyl)pyrroles.

| Ex. No. | Structure |
|---|---|
| 60A | [structure] |
| 60B | [structure] |
| 61A | [structure] |
| 61B | [structure] |
| 62A | [structure] |

TABLE 7-continued

Unsymmetrical 5-[(N-Propyl)-Aminomethyl]-3-halo-4-[2,3,4-Trimethoxyphenyl)-pyrrole 2-carboxylic acid esters, Unsymmetrical 5-[(N-Propyl)-Aminomethyl]-3-halo-4-[2,3,4-Trimethoxyphenyl)pyrrole 2-carboxylic acids, and Unsymmetrical 2-Cyano-5-[(N-Propyl)-Aminomethyl]-3-halo-4-[2,3,4-Trimethoxy-phenyl)pyrroles.

| Ex. No. | Structure |
|---|---|
| 62B | (structure) |
| 63A | (structure) |
| 63B | (structure) |
| 64A | (structure) |
| 64B | (structure) |

TABLE 8

Unsymmetrical 5-[N-(Aminoethyl)-aminomethyl]-3-halo-4-[2,3,4-Trimethoxyphenyl)-pyrrole 2-carboxylic acid esters, Unsymmetrical 5-[N-(Aminoethyl)-aminomethyl]-3-halo-4-[2,3,4-Tri-methoxyphenyl)pyrrole 2-carboxylic acids, and Unsymmetrical 2-Cyano-5-[N-(Aminoethyl)Aminomethyl]-3-halo-4-[2,3,4-Trimethoxy-phenyl)pyrroles.

| Ex. No. | Structure |
|---|---|
| 65A | (structure) |
| 65B | (structure) |
| 66A | (structure) |
| 66B | (structure) |

TABLE 8-continued

Unsymmetrical 5-[N-(Aminoethyl)-aminomethyl]-3-halo-4-[2,3,4-Trimethoxyphenyl)-pyrrole 2-carboxylic acid esters, Unsymmetrical 5-[N-(Aminoethyl)-aminomethyl]-3-halo-4-[2,3,4-Tri-methoxyphenyl)pyrrole 2-carboxylic acids, and Unsymmetrical 2-Cyano-5-[N-(Aminoethyl)Aminomethyl]-3-halo-4-[2,3,4-Trimethoxy-phenyl)pyrroles.

| Ex. No. | Structure |
|---|---|
| 67A | (4-(2,3,4-trimethoxyphenyl)-3-chloro-pyrrole-2-carboxylic acid isopropyl ester with 5-CH$_2$-NH-CH$_2$CH$_2$-NH$_2$) |
| 67B | (4-(2,3,4-trimethoxyphenyl)-3-bromo-pyrrole-2-carboxylic acid isopropyl ester with 5-CH$_2$-NH-CH$_2$CH$_2$-NH$_2$) |
| 68A | (4-(2,3,4-trimethoxyphenyl)-3-chloro-2-cyano-pyrrole with 5-CH$_2$-NH-CH$_2$CH$_2$-NH$_2$) |
| 68B | (4-(2,3,4-trimethoxyphenyl)-3-bromo-2-cyano-pyrrole with 5-CH$_2$-NH-CH$_2$CH$_2$-NH$_2$) |
| 69A | (4-(2,3,4-trimethoxyphenyl)-3-chloro-pyrrole-2-carboxylic acid with 5-CH$_2$-NH-CH$_2$CH$_2$-NH$_2$) |
| 69B | (4-(2,3,4-trimethoxyphenyl)-3-bromo-pyrrole-2-carboxylic acid with 5-CH$_2$-NH-CH$_2$CH$_2$-NH$_2$) |

TABLE 9

Unsymmetrical 5-[(N-(2-Hydroxyethyl)-aminomethyl]-3-halo-4-[2,3,4-Trimethoxyphenyl)-pyrrole 2-carboxylic acid esters, Unsymmetrical 5-[N-(2-Hydroxyethyl)-aminomethyl]-3-halo-4-[2,3,4-Trimethoxyphenyl)pyrrole 2-carboxylic acids, and Unsymmetrical 2-Cyano-5-[N-(2-Hydroxyethyl)aminomethyl]-3-halo-4-[2,3,4-Trimethoxyphenyl)pyrroles.

| Ex. No. | Structure |
|---|---|
| 70A | (4-(2,3,4-trimethoxyphenyl)-3-chloro-pyrrole-2-carboxylic acid methyl ester with 5-CH$_2$-NH-CH$_2$CH$_2$-OH) |

TABLE 9-continued

Unsymmetrical 5-[(N-(2-Hydroxyethyl)-aminomethyl]-3-halo-4-[2,3,4-Trimethoxyphenyl)-pyrrole 2-carboxylic acid esters, Unsymmetrical 5-[N-(2-Hydroxyethyl)-aminomethyl]-3-halo-4-[2,3,4-Trimethoxyphenyl)pyrrole 2-carboxylic acids, and Unsymmetrical 2-Cyano-5-[N-(2-Hydroxyethyl) aminomethyl]-3-halo-4-[2,3,4-Trimethoxyphenyl)pyrroles.

| Ex. No. | Structure |
|---|---|
| 70B | (H3CO, H3CO, H3CO-phenyl)-pyrrole with Br, CO2CH3, CH2-NH-CH2CH2-OH |
| 71A | (H3CO, H3CO, H3CO-phenyl)-pyrrole with Cl, CO2CH2CH3, CH2-NH-CH2CH2-OH |
| 71B | (H3CO, H3CO, H3CO-phenyl)-pyrrole with Br, CO2CH2CH3, CH2-NH-CH2CH2-OH |
| 72A | (H3CO, H3CO, H3CO-phenyl)-pyrrole with Cl, CO2—n-Pr, CH2-NH-CH2CH2-OH |
| 72B | (H3CO, H3CO, H3CO-phenyl)-pyrrole with Br, CO2—n-Pr, CH2-NH-CH2CH2-OH |
| 73A | (H3CO, H3CO, H3CO-phenyl)-pyrrole with Cl, C≡N, CH2-NH-CH2CH2-OH |
| 73B | (H3CO, H3CO, H3CO-phenyl)-pyrrole with Br, C≡N, CH2-NH-CH2CH2-OH |
| 74A | (H3CO, H3CO, H3CO-phenyl)-pyrrole with Cl, CO2H, CH2-NH-CH2CH2-OH |

TABLE 9-continued

Unsymmetrical 5-[(N-(2-Hydroxyethyl)-aminomethyl]-3-halo-4-[2,3,4-Trimethoxyphenyl)-pyrrole 2-carboxylic acid esters, Unsymmetrical 5-[N-(2-Hydroxyethyl)-aminomethyl]-3-halo-4-[2,3,4-Trimethoxyphenyl)pyrrole 2-carboxylic acids, and Unsymmetrical 2-Cyano-5-[N-(2-Hydroxyethyl)aminomethyl]-3-halo-4-[2,3,4-Trimethoxyphenyl)pyrroles.

| Ex. No. | Structure |
|---|---|
| 74B | (3-Bromo-4-(2,3,4-trimethoxyphenyl)-5-{[(2-hydroxyethyl)amino]methyl}-1H-pyrrole-2-carboxylic acid) |

TABLE 10

Unsymmetrical 5-[N-(2-Sulfoxyethyl)-aminomethyl]-3-halo-4-[2,3,4-Trimethoxyphenyl)-pyrrole 2-carboxylic acid esters, Unsymmetrical 5-[N-(2-Sulfoxyethyl)-aminomethyl]-3-halo-4-[2,3,4-Trimethoxyphenyl)pyrrole-2-carboxylic acids, and Unsymmetrical 2-Cyano-5-[N-(2-Sulfoxyethyl)aminomethyl]-3-halo-4-[2,3,4-Trimethoxyphenyl)pyrroles.

| Ex. No. | Structure |
|---|---|
| 75A | (3-Chloro-4-(2,3,4-trimethoxyphenyl)-5-{[(2-sulfoethyl)amino]methyl}-1H-pyrrole-2-carboxylic acid methyl ester) |
| 75B | (3-Bromo-4-(2,3,4-trimethoxyphenyl)-5-{[(2-sulfoethyl)amino]methyl}-1H-pyrrole-2-carboxylic acid methyl ester) |

TABLE 10-continued

Unsymmetrical 5-[N-(2-Sulfoxyethyl)-aminomethyl]-3-halo-4-[2,3,4-Trimethoxyphenyl)-pyrrole 2-carboxylic acid esters, Unsymmetrical 5-[N-(2-Sulfoxyethyl)-aminomethyl]-3-halo-4-[2,3,4-Trimethoxyphenyl)pyrrole-2-carboxylic acids, and Unsymmetrical 2-Cyano-5-[N-(2-Sulfoxyethyl)aminomethyl]-3-halo-4-[2,3,4-Trimethoxyphenyl)pyrroles.

| Ex. No. | Structure |
|---|---|
| 76A | (3-Chloro-4-(2,3,4-trimethoxyphenyl)-5-{[(2-sulfoethyl)amino]methyl}-1H-pyrrole-2-carboxylic acid ethyl ester) |
| 76B | (3-Bromo-4-(2,3,4-trimethoxyphenyl)-5-{[(2-sulfoethyl)amino]methyl}-1H-pyrrole-2-carboxylic acid ethyl ester) |
| 77A | (3-Chloro-4-(2,3,4-trimethoxyphenyl)-5-{[(2-sulfoethyl)amino]methyl}-1H-pyrrole-2-carboxylic acid n-propyl ester) |
| 77B | (3-Bromo-4-(2,3,4-trimethoxyphenyl)-5-{[(2-sulfoethyl)amino]methyl}-1H-pyrrole-2-carboxylic acid n-propyl ester) |

TABLE 10-continued

Unsymmetrical 5-[N-(2-Sulfoxyethyl)-aminomethyl]-3-halo-4-[2,3,4-Trimethoxyphenyl)-pyrrole 2-carboxylic acid esters, Unsymmetrical 5-[N-(2-Sulfoxyethyl)-aminomethyl]-3-halo-4-[2,3,4-Trimethoxyphenyl) pyrrole-2-carboxylic acids, and Unsymmetrical 2-Cyano-5-[N-(2-Sulfoxyethyl)aminomethyl]-3-halo-4-[2,3,4-Trimethoxyphenyl)pyrroles.

| Ex. No. | Structure |
|---|---|
| 78A | (H₃CO, H₃CO, H₃CO phenyl)-pyrrole with Cl, C≡N, CH₂NH-CH₂CH₂-SO₃H |
| 78B | (H₃CO, H₃CO, H₃CO phenyl)-pyrrole with Br, C≡N, CH₂NH-CH₂CH₂-SO₃H |
| 79A | (H₃CO, H₃CO, H₃CO phenyl)-pyrrole with Cl, CO₂H, CH₂NH-CH₂CH₂-SO₃H |
| 79B | (H₃CO, H₃CO, H₃CO phenyl)-pyrrole with Br, CO₂H, CH₂NH-CH₂CH₂-SO₃H |

TABLE 11

Unsymmetrical 5-[N-(Formamidino)-aminomethyl]-3-halo-4-[2,3,4-Trimethoxyphenyl)-pyrrole 2-carboxylic acid esters, Unsymmetrical 5-[N-(Formami-dino)-aminomethyl]-3-halo-4-[2,3,4-Trimethoxyphenyl)pyrrole 2-carboxylic acids, and Unsymmetrical 2-Cyano-5-[N-(Formamidino) aminomethyl]-3-halo-4-[2,3,4-Trimethoxyphenyl)pyrroles.

| Ex. No. | Structure |
|---|---|
| 80A | (H₃CO, H₃CO, H₃CO phenyl)-pyrrole with Cl, CO₂CH₃, CH₂NH-C(=NH)-NH₂ |
| 80B | (H₃CO, H₃CO, H₃CO phenyl)-pyrrole with Br, CO₂CH₃, CH₂NH-C(=NH)-NH₂ |
| 81A | (H₃CO, H₃CO, H₃CO phenyl)-pyrrole with Cl, CO₂CH₂CH₃, CH₂NH-C(=NH)-NH₂ |
| 81B | (H₃CO, H₃CO, H₃CO phenyl)-pyrrole with Br, CO₂CH₂CH₃, CH₂NH-C(=NH)-NH₂ |

TABLE 11-continued

Unsymmetrical 5-[N-(Formamidino)-aminomethyl]-3-halo-4-[2,3,4-Trimethoxyphenyl)-pyrrole 2-carboxylic acid esters, Unsymmetrical 5-[N-(Formami-dino)-aminomethyl]-3-halo-4-[2,3,4-Trimethoxyphenyl)pyrrole 2-carboxylic acids, and Unsymmetrical 2-Cyano-5-[N-(Formamidino) aminomethyl]-3-halo-4-[2,3,4-Trimethoxyphenyl)pyrroles.

| Ex. No. | Structure |
|---|---|
| 82A | 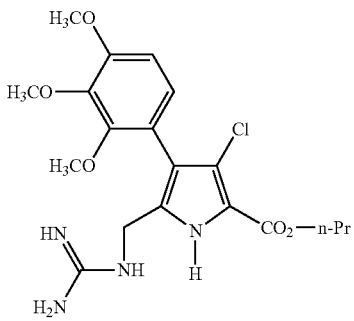 |
| 82B | 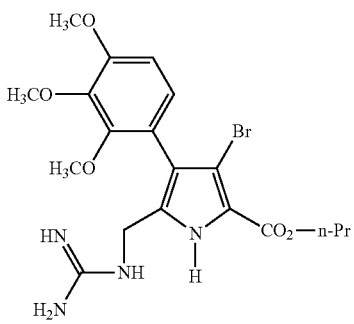 |
| 83A | 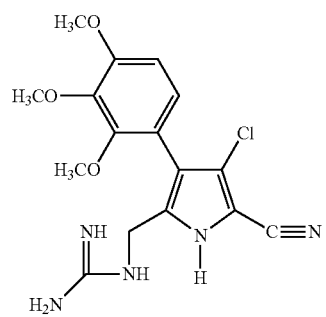 [SMILES: COc1ccc(-c2c(CNC(=N)N)[nH]c(C#N)c2Cl)c(OC)c1OC] |
| 83B | 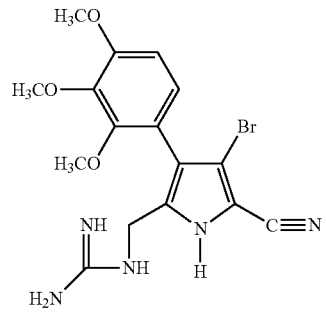 [SMILES: COc1ccc(-c2c(CNC(=N)N)[nH]c(C#N)c2Br)c(OC)c1OC] |
| 84A | 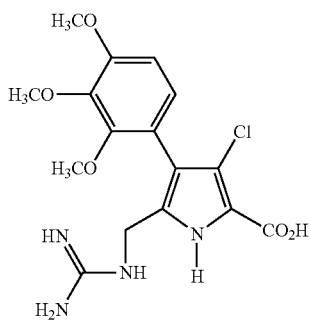 [SMILES: COc1ccc(-c2c(CNC(=N)N)[nH]c(C(=O)O)c2Cl)c(OC)c1OC] |
| 84B | 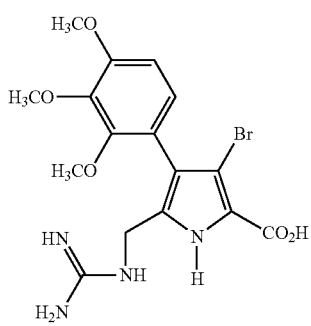 [SMILES: COc1ccc(-c2c(CNC(=N)N)[nH]c(C(=O)O)c2Br)c(OC)c1OC] |

TABLE 12

Unsymmetrical 5-[N-(2-Carboxyethyl)-aminomethyl]-3-halo-4-[2,3,4-Trimethoxyphenyl)-pyrrole 2-carboxylic acid esters, Unsymmetrical 5-[N-(2-Carboxyethyl)-aminomethyl]-3-halo-4-[2,3,4-Trimethoxyphenyl) pyrrole 2-carboxylic acids, and Unsymmetrical 2-Cyano-5-[N-(2-Carboxyethyl)aminomethyl]-3-halo-4-[2,3,4-Trimethoxyphenyl)pyrroles.

| Ex. No. | Structure |
|---|---|
| 85A | 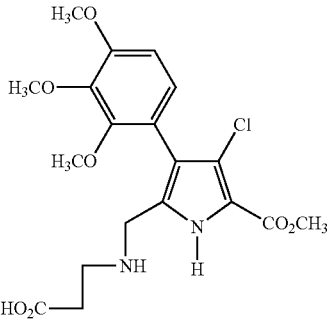 |

TABLE 12-continued

Unsymmetrical 5-[N-(2-Carboxyethyl)-aminomethyl]-3-halo-4-[2,3,4-Trimethoxyphenyl)-pyrrole 2-carboxylic acid esters, Unsymmetrical 5-[N-(2-Carboxyethyl)-aminomethyl]-3-halo-4-[2,3,4-Trimethoxyphenyl) pyrrole 2-carboxylic acids, and Unsymmetrical 2-Cyano-5-[N-(2-Carboxyethyl)aminomethyl]-3-halo-4-[2,3,4-Trimethoxyphenyl)pyrroles.

| Ex. No. | Structure |
|---|---|
| 85B | 3-Br, 4-(2,3,4-trimethoxyphenyl)-5-[[(2-carboxyethyl)amino]methyl]-pyrrole-2-carboxylic acid methyl ester |
| 86A | 3-Cl, 4-(2,3,4-trimethoxyphenyl)-5-[[(2-carboxyethyl)amino]methyl]-pyrrole-2-carboxylic acid ethyl ester |
| 86B | 3-Br, 4-(2,3,4-trimethoxyphenyl)-5-[[(2-carboxyethyl)amino]methyl]-pyrrole-2-carboxylic acid ethyl ester |
| 87A | 3-Cl, 4-(2,3,4-trimethoxyphenyl)-5-[[(2-carboxyethyl)amino]methyl]-pyrrole-2-carboxylic acid n-propyl ester |
| 87B | 3-Br, 4-(2,3,4-trimethoxyphenyl)-5-[[(2-carboxyethyl)amino]methyl]-pyrrole-2-carboxylic acid n-propyl ester |
| 88A | 3-Cl, 4-(2,3,4-trimethoxyphenyl)-5-[[(2-carboxyethyl)amino]methyl]-2-cyano-pyrrole |
| 88B | 3-Br, 4-(2,3,4-trimethoxyphenyl)-5-[[(2-carboxyethyl)amino]methyl]-2-cyano-pyrrole |
| 89A | 3-Cl, 4-(2,3,4-trimethoxyphenyl)-5-[[(2-carboxyethyl)amino]methyl]-pyrrole-2-carboxylic acid |

TABLE 12-continued

Unsymmetrical 5-[N-(2-Carboxyethyl)-aminomethyl]-3-halo-4-[2,3,4-Trimethoxyphenyl)-pyrrole 2-carboxylic acid esters, Unsymmetrical 5-[N-(2-Carboxyethyl)-aminomethyl]-3-halo-4-[2,3,4-Trimethoxyphenyl) pyrrole 2-carboxylic acids, and Unsymmetrical 2-Cyano-5-[N-(2-Carboxyethyl)aminomethyl]-3-halo-4-[2,3,4-Trimethoxyphenyl)pyrroles.

| Ex. No. | Structure |
|---|---|
| 89B | (structure) |

TABLE 13

Unsymmetrical 5-[N-(2-Imidazol-2-carbonyl)-aminomethyl]-3-halo-4-[2,3,4-Trimethoxyphenyl)-pyrrole 2-carboxylic acid esters, Unsymmetrical 5-[N-(2-Imidazol-2-carbonyl)-aminomethyl]-3-halo-4-[2,3,4-Trimethoxyphenyl)pyrrole 2-carboxylic acids, and Unsymmetrical 2-Cyano-5-[N-(2-Imidazol-2-carbonyl)-aminomethyl]-3-halo-4-[2,3,4-Trimethoxyphenyl)pyrroles.

| Ex. No. | Structure |
|---|---|
| 90A | (structure) |
| 90B | (structure) |

TABLE 13-continued

Unsymmetrical 5-[N-(2-Imidazol-2-carbonyl)-aminomethyl]-3-halo-4-[2,3,4-Trimethoxyphenyl)-pyrrole 2-carboxylic acid esters, Unsymmetrical 5-[N-(2-Imidazol-2-carbonyl)-aminomethyl]-3-halo-4-[2,3,4-Trimethoxyphenyl)pyrrole 2-carboxylic acids, and Unsymmetrical 2-Cyano-5-[N-(2-Imidazol-2-carbonyl)-aminomethyl]-3-halo-4-[2,3,4-Trimethoxyphenyl)pyrroles.

| Ex. No. | Structure |
|---|---|
| 91A | (structure) |
| 91B | (structure) |
| 92A | (structure) |

TABLE 13-continued

Unsymmetrical 5-[N-(2-Imidazol-2-carbonyl)-aminomethyl]-3-halo-4-[2,3,4-Trimethoxyphenyl)-pyrrole 2-carboxylic acid esters, Unsymmetrical 5-[N-(2-Imidazol-2-carbonyl)-aminomethyl]-3-halo-4-[2,3,4-Trimethoxyphenyl)pyrrole 2-carboxylic acids, and Unsymmetrical 2-Cyano-5-[N-(2-Imidazol-2-carbonyl)-aminomethyl]-3-halo-4-[2,3,4-Trimethoxyphenyl)pyrroles.

| Ex. No. | Structure |
|---|---|
| 92B | [structure: 3-Br, 4-(2,3,4-trimethoxyphenyl), 5-(N-(imidazol-2-carbonyl)aminomethyl) pyrrole with CO₂-n-Pr] |
| 93A | [structure: 3-Cl, 4-(2,3,4-trimethoxyphenyl), 5-(N-(imidazol-2-carbonyl)aminomethyl) pyrrole with C≡N] |
| 93B | [structure: 3-Br, 4-(2,3,4-trimethoxyphenyl), 5-(N-(imidazol-2-carbonyl)aminomethyl) pyrrole with C≡N] |
| 94A | [structure: 3-Cl, 4-(2,3,4-trimethoxyphenyl), 5-(N-(imidazol-2-carbonyl)aminomethyl) pyrrole with CO₂H] |
| 94B | [structure: 3-Br, 4-(2,3,4-trimethoxyphenyl), 5-(N-(imidazol-2-carbonyl)aminomethyl) pyrrole with CO₂H] |

TABLE 14

Unsymmetrical 5-[N-(Aminoacetyl)-aminomethyl]-3-halo-4-[2,3,4-Trimethoxyphenyl)-pyrrole 2-carboxylic acid esters, Unsymmetrical 5-[N-(Amino-acetyl)-aminomethyl]-3-halo-4-[2,3,4-Trimethoxyphenyl)pyrrole 2-carboxylic acids, and Unsymmetrical 2-Cyano-5-[N-(Aminoacetyl)aminomethyl]-3-halo-4-[2,3,4-Trimethoxyphenyl)pyrroles.

| Ex. No. | Structure |
|---|---|
| 95A | [structure: 3-Cl, 4-(2,3,4-trimethoxyphenyl), 5-(N-(aminoacetyl)aminomethyl) pyrrole with CO₂CH₃] |
| 95B | [structure: 3-Br, 4-(2,3,4-trimethoxyphenyl), 5-(N-(aminoacetyl)aminomethyl) pyrrole with CO₂CH₃] |

TABLE 14-continued

Unsymmetrical 5-[N-(Aminoacetyl)-aminomethyl]-3-halo-4-[2,3,4-Trimethoxyphenyl)-pyrrole 2-carboxylic acid esters, Unsymmetrical 5-[N-(Amino-acetyl)-aminomethyl]-3-halo-4-[2,3,4-Trimethoxyphenyl) pyrrole 2-carboxylic acids, and Unsymmetrical 2-Cyano-5-[N-(Amino-acetyl)aminomethyl]-3-halo-4-[2,3,4-Trimethoxyphenyl)pyrroles.

| Ex. No. | Structure |
|---|---|
| 96A | 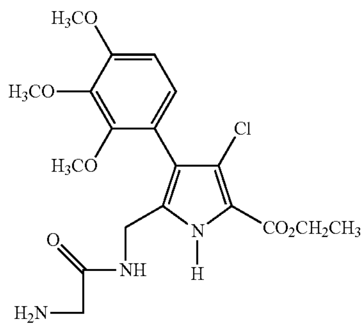 |
| 96B | 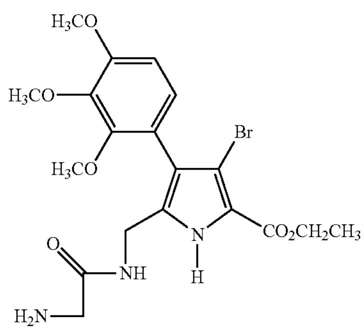 |
| 97A | 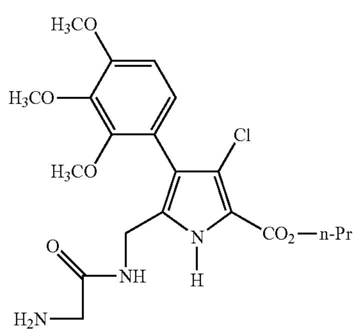 |
| 97B | 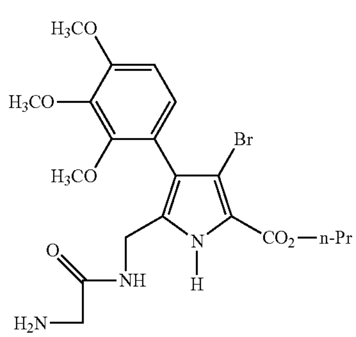 |
| 98A | |
| 98B | |
| 99A | |
| 99B | |

TABLE 15

Unsymmetrical 5-[N-(2-Imidazol-yl)-aminomethyl]-3-halo-4-[2,3,4-Trimethoxyphenyl)-pyrrole 2-carboxylic acid esters, Unsymmetrical 5-[N-(2-Imidazol-yl)-aminomethyl]-3-halo-4-[2,3,4-Trimethoxyphenyl)pyrrole 2-carboxylic acid, and Unsymmetrical 2-Cyano-5-[N-(2-Imidazol-yl)aminomethyl]-3-halo-4-[2,3,4-Trimethoxyphenyl)pyrroles.

| Ex. No. | Structure |
|---|---|
| 100A | 3-Cl, 2-CO$_2$CH$_3$ pyrrole derivative |
| 100B | 3-Br, 2-CO$_2$CH$_3$ pyrrole derivative |
| 101A | 3-Cl, 2-CO$_2$CH$_2$CH$_3$ pyrrole derivative |
| 101B | 3-Br, 2-CO$_2$CH$_2$CH$_3$ pyrrole derivative |
| 102A | 3-Cl, 2-CO$_2$—n-Pr pyrrole derivative |
| 102B | 3-Br, 2-CO$_2$—n-Pr pyrrole derivative |
| 103A | 3-Cl, 2-CN pyrrole derivative |
| 103B | 3-Br, 2-CN pyrrole derivative |

TABLE 15-continued

Unsymmetrical 5-[N-(2-Imidazol-yl)-aminomethyl]-3-halo-4-[2,3,4-Trimethoxyphenyl)-pyrrole 2-carboxylic acid esters, Unsymmetrical 5-[N-(2-Imidazol-yl)-aminomethyl]-3-halo-4-[2,3,4-Trimethoxyphenyl)pyrrole 2-carboxylic acid, and Unsymmetrical 2-Cyano-5-[N-(2-Imidazol-yl)aminomethyl]-3-halo-4-[2,3,4-Trimethoxyphenyl)pyrroles.

| Ex. No. | Structure |
| --- | --- |
| 104A | (structure) |
| 104B | (structure) |

TABLE 16

Unsymmetrical 5-[N-(Carboxymethyl)-aminomethyl]-3-halo-4-[2,3,4-Trimethoxyphenyl)-pyrrole 2-carboxylic acid esters, Unsymmetrical 5-[N-(Carboxymethyl)-aminomethyl]-3-halo-4-[2,3,4-Trimethoxyphenyl)pyrrole 2-carboxylic acids, and Unsymmetrical 2-Cyano-5-[N-(Carboxymethyl)aminomethyl]-3-halo-4-[2,3,4-Trimethoxyphenyl)pyrroles.

| Ex. No. | Structure |
| --- | --- |
| 105A | (structure) |
| 105B | (structure) |
| 106A | (structure) |
| 106B | (structure) |
| 107A | (structure) |

TABLE 16-continued

Unsymmetrical 5-[N-(Carboxymethyl)-aminomethyl]-3-halo-4-[2,3,4-Trimethoxyphenyl)-pyrrole 2-carboxylic acid esters, Unsymmetrical 5-[N-(Carboxymethyl)-aminomethyl]-3-halo-4-[2,3,4-Trimethoxyphenyl) pyrrole 2-carboxylic acids, and Unsymmetrical 2-Cyano-5-[N-(Carboxymethyl)aminomethyl]-3-halo-4-[2,3,4-Trimethoxyphenyl)pyrroles.

| Ex. No. | Structure |
|---|---|
| 107B | (structure) |
| 108A | (structure) |
| 108B | (structure) |
| 109A | (structure) |
| 109B | (structure) |

TABLE 17

Unsymmetrical 5-[N-5-[(2-Amino-2-Carboxypentyl)]-amino-methyl]-3-halo-4-[2,3,4-Trimethoxyphenyl)-pyrrole 2-carboxylic acid esters, Unsymmetrical 5-[N-5-[(2-Amino-2-Carboxypentyl)]-aminomethyl]-3-halo-4-[2,3,4-Trimethoxyphenyl)-pyrrole 2-carboxylic acids, and Unsymmetrical 2-Cyano-5-[N-5-[(2-Amino-2-Carboxy-pentyl)]-aminomethyl]-3-halo-4-[2,3,4-Trimethoxyphenyl)pyrroles.

| Ex. No. | Structure |
|---|---|
| 110A | (structure) |
| 110B | (structure) |

TABLE 17-continued

Unsymmetrical 5-[N-5-[(2-Amino-2-Carboxypentyl)]-amino-methyl]-3-halo-4-[2,3,4-Trimethoxyphenyl)-pyrrole 2-carboxylic acid esters, Unsymmetrical 5-[N-5-[(2-Amino-2-Carboxypentyl)]-aminomethyl]-3-halo-4-[2,3,4-Trimethoxyphenyl)-pyrrole 2-carboxylic acids, and Unsymmetrical 2-Cyano-5-[N-5-[(2-Amino-2-Carboxy-pentyl)]-aminomethyl]-3-halo-4-[2,3,4-Trimethoxyphenyl)pyrroles.

| Ex. No. | Structure |
|---|---|
| 111A | (structure: 2,3,4-trimethoxyphenyl-4-yl, 3-Cl, 2-CO₂CH₂CH₃ pyrrole with 5-CH₂-NH-(CH₂)₄-CH(NH₂)-CO₂H) |
| 111B | (structure: 2,3,4-trimethoxyphenyl-4-yl, 3-Br, 2-CO₂CH₂CH₃ pyrrole with 5-CH₂-NH-(CH₂)₄-CH(NH₂)-CO₂H) |
| 112A | (structure: 2,3,4-trimethoxyphenyl-4-yl, 3-Cl, 2-CO₂-n-Pr pyrrole with 5-CH₂-NH-(CH₂)₄-CH(NH₂)-CO₂H) |
| 112B | (structure: 2,3,4-trimethoxyphenyl-4-yl, 3-Br, 2-CO₂-n-Pr pyrrole with 5-CH₂-NH-(CH₂)₄-CH(NH₂)-CO₂H) |
| 113A | (structure: 2,3,4-trimethoxyphenyl-4-yl, 3-Cl, 2-C≡N pyrrole with 5-CH₂-NH-(CH₂)₄-CH(NH₂)-CO₂H) |
| 113B | (structure: 2,3,4-trimethoxyphenyl-4-yl, 3-Br, 2-C≡N pyrrole with 5-CH₂-NH-(CH₂)₄-CH(NH₂)-CO₂H) |
| 114A | (structure: 2,3,4-trimethoxyphenyl-4-yl, 3-Cl, 2-CO₂H pyrrole with 5-CH₂-NH-(CH₂)₄-CH(NH₂)-CO₂H) |

TABLE 17-continued

Unsymmetrical 5-[N-5-[(2-Amino-2-Carboxypentyl)]-amino-methyl]-3-halo-4-[2,3,4-Trimethoxyphenyl)-pyrrole 2-carboxylic acid esters, Unsymmetrical 5-[N-5-[(2-Amino-2-Carboxypentyl)]-aminomethyl]-3-halo-4-[2,3,4-Trimethoxyphenyl)-pyrrole 2-carboxylic acids, and Unsymmetrical 2-Cyano-5-[N-5-[(2-Amino-2-Carboxy-pentyl)]-aminomethyl]-3-halo-4-[2,3,4-Trimethoxyphenyl)pyrroles.

| Ex. No. | Structure |
|---|---|
| 114B | (structure: 4-(2,3,4-trimethoxyphenyl)-3-Br-pyrrole with 5-CH$_2$-NH-(CH$_2$)$_4$-CH(NH$_2$)-CO$_2$H and 2-CO$_2$H) |

TABLE 18

Unsymmetrical 5-Aminomethyl-3-Substituted-4-[2,3,4-Trimethoxy-phenyl)-pyrrole 2-carboxylic acid esters, Unsymmetrical 5-Aminomethyl-3-Substituted-4-[2,3,4-Trimethoxy-phenyl)pyrrole 2-carboxylic acids, and Unsymmetrical 2-Cyano-5-Aminomethyl-3-Substituted-4-[2,3,4-Trimethoxy-phenyl)pyrroles.

| Ex. No. | Structure |
|---|---|
| 115A | 4-(2,3,4-trimethoxyphenyl)-3-CH$_2$OH-5-CH$_2$NH$_2$-pyrrole-2-CO$_2$CH$_3$ |
| 115B | 4-(2,3,4-trimethoxyphenyl)-3-CH$_2$OH-5-CH$_2$NH$_2$-pyrrole-2-CO$_2$CH$_2$CH$_3$ |
| 116A | 4-(2,3,4-trimethoxyphenyl)-3-CH$_2$OH-5-CH$_2$NH$_2$-pyrrole-2-CO$_2$H |
| 116B | 4-(2,3,4-trimethoxyphenyl)-3-CH$_2$OH-5-CH$_2$NH$_2$-pyrrole-2-C≡N |
| 117A | 4-(2,3,4-trimethoxyphenyl)-3-CHF$_2$-5-CH$_2$NH$_2$-pyrrole-2-CO$_2$CH$_3$ |
| 117B | 4-(2,3,4-trimethoxyphenyl)-3-CHF$_2$-5-CH$_2$NH$_2$-pyrrole-2-CO$_2$CH$_2$CH$_3$ |
| 118A | 4-(2,3,4-trimethoxyphenyl)-3-CHF$_2$-5-CH$_2$NH$_2$-pyrrole-2-CO$_2$H |

TABLE 18-continued

Unsymmetrical 5-Aminomethyl-3-Substituted-4-[2,3,4-Trimethoxy-phenyl)-pyrrole 2-carboxylic acid esters, Unsymmetrical 5-Aminomethyl-3-Substituted-4-[2,3,4-Trimethoxy-phenyl)pyrrole 2-carboxylic acids, and Unsymmetrical 2-Cyano-5-Aminomethyl-3-Substituted-4-[2,3,4-Trimethoxy-phenyl)pyrroles.

| Ex. No. | Structure |
|---|---|
| 118B | (structure: 3-CHF$_2$, 2-CN pyrrole with 2,3,4-trimethoxyphenyl at 4-position and aminomethyl at 5-position) |

TABLE 19

Unsymmetrical 5-Aminomethyl-3-Substituted-4-[2,3,4-Trimethoxy-phenyl)-pyrrole 2-carboxylic acid esters, Unsymmetrical 5-Aminomethyl-3-Substituted-4-[2,3,4-Trimethoxyphenyl)pyrrole 2-carboxylic acids, and Unsymmetrical 2-Cyano-5-Aminomethyl-3-Substituted-4-[2,3,4-Trimethoxyphenyl)pyrroles.

| Ex. No. | Structure |
|---|---|
| 119A | (3-CH$_2$OCH$_3$, 2-CO$_2$CH$_3$ pyrrole with 2,3,4-trimethoxyphenyl at 4-position and aminomethyl at 5-position) |
| 119B | (3-CH$_2$OCH$_3$, 2-CO$_2$CH$_2$CH$_3$ pyrrole with 2,3,4-trimethoxyphenyl at 4-position and aminomethyl at 5-position) |
| 120A | (3-CH$_2$OCH$_3$, 2-CO$_2$H pyrrole with 2,3,4-trimethoxyphenyl at 4-position and aminomethyl at 5-position) |
| 120B | (3-CH$_2$OCH$_3$, 2-CN pyrrole with 2,3,4-trimethoxyphenyl at 4-position and aminomethyl at 5-position) |
| 121A | (3-COCH$_3$, 2-CO$_2$CH$_3$ pyrrole with 2,3,4-trimethoxyphenyl at 4-position and aminomethyl at 5-position) |
| 121B | (3-COCH$_3$, 2-CO$_2$CH$_2$CH$_3$ pyrrole with 2,3,4-trimethoxyphenyl at 4-position and aminomethyl at 5-position) |
| 122A | (3-COCH$_3$, 2-CO$_2$H pyrrole with 2,3,4-trimethoxyphenyl at 4-position and aminomethyl at 5-position) |
| 122B | (3-COCH$_3$, 2-CN pyrrole with 2,3,4-trimethoxyphenyl at 4-position and aminomethyl at 5-position) |

TABLE 20

Unsymmetrical 5-Aminomethyl-3-Substituted-4-[2,3,4-Trimethoxyphenyl)-pyrrole 2-carboxylic acid esters, Unsymmetrical 5-Aminomethyl-3-Substituted-4-[2,3,4-Trimethoxyphenyl)pyrrole 2-carboxylic acids, and Unsymmetrical 2-Cyano-5-Aminomethyl-3-Substituted-4-[2,3,4-Trimethoxyphenyl)pyrroles.

| Ex. No. | Structure |
|---|---|
| 123A | (structure) |
| 123B | (structure) |
| 124A | (structure) |
| 124B | (structure) |
| 125A | (structure) |
| 125B | (structure) |
| 126A | (structure) |
| 126B | (structure) |

TABLE 21

Unsymmetrical 5-Aminomethyl-3-Substituted-4-[2,3,4-Trimethoxyphenyl)-pyrrole 2-carboxylic acid esters, Unsymmetrical 5-Aminomethyl-3-Substituted-4-[2,3,4-Trimethoxyphenyl)pyrrole 2-carboxylic acids, and Unsymmetrical 2-Cyano-5-Aminomethyl-3-Substituted-4-[2,3,4-Trimethoxyphenyl)pyrroles.

| Ex. No. | Structure |
|---|---|
| 127A | (structure) |

TABLE 21-continued

Unsymmetrical 5-Aminomethyl-3-Substituted-4-[2,3,4-Trimethoxyphenyl)-pyrrole 2-carboxylic acid esters, Unsymmetrical 5-Aminomethyl-3-Substituted-4-[2,3,4-Trimethoxyphenyl)pyrrole 2-carboxylic acids, and Unsymmetrical 2-Cyano-5-Aminomethyl-3-Substituted-4-[2,3,4-Trimethoxyphenyl)pyrroles.

| Ex. No. | Structure |
|---|---|
| 127B | 3-vinyl-4-(2,3,4-trimethoxyphenyl)-5-(aminomethyl)-1H-pyrrole-2-carboxylic acid ethyl ester |
| 128A | 3-vinyl-4-(2,3,4-trimethoxyphenyl)-5-(aminomethyl)-1H-pyrrole-2-carboxylic acid |
| 128B | 3-vinyl-4-(2,3,4-trimethoxyphenyl)-5-(aminomethyl)-2-cyano-1H-pyrrole |
| 129A | 3-allyl-4-(2,3,4-trimethoxyphenyl)-5-(aminomethyl)-1H-pyrrole-2-carboxylic acid methyl ester |
| 129B | 3-allyl-4-(2,3,4-trimethoxyphenyl)-5-(aminomethyl)-1H-pyrrole-2-carboxylic acid ethyl ester |
| 130A | 3-allyl-4-(2,3,4-trimethoxyphenyl)-5-(aminomethyl)-1H-pyrrole-2-carboxylic acid |
| 130A | 3-allyl-4-(2,3,4-trimethoxyphenyl)-5-(aminomethyl)-2-cyano-1H-pyrrole |

TABLE 22

Unsymmetical 5-[Aminomethyl]-3-Substituted-4-[2,3,4-Trimethoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxy-phenyl)pyrroles.

| Ex. No. | Structure |
|---|---|
| 131A | 3-(2-methoxycarbonylvinyl)-4-(2,3,4-trimethoxyphenyl)-5-(aminomethyl)-1H-pyrrole-2-carboxylic acid methyl ester |
| 131B | 3-(2-methoxycarbonylvinyl)-4-(2,3,4-trimethoxyphenyl)-5-(aminomethyl)-1H-pyrrole-2-carboxylic acid ethyl ester |

TABLE 22-continued

Unsymmetical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxy-phenyl)pyrroles.

| Ex. No. | Structure |
|---|---|
| 132A | (structure) |
| 132B | (structure) |
| 133A | (structure) |
| 133B | (structure) |
| 134A | (structure) |
| 134B | (structure) |

TABLE 23

Unsymmetrical 5-[(n-Propyl)-Aminomethyl]-3-Substituted-4-[2,3,4-Trimethoxyphenyl)-pyrrole 2-carboxylic acid esters, Unsymmetrical 5-[(n-Propyl)-Aminomethyl]- 3-Substituted-4-[2,3,4-Trimethoxyphenyl) pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 135A | (structure) |
| 135B | (structure) |
| 136A | (structure) |

TABLE 23-continued

Unsymmetrical 5-[(n-Propyl)-Aminomethyl]-3-Substituted-4-[2,3,4-Trimethoxyphenyl)-pyrrole 2-carboxylic acid esters, Unsymmetrical 5-[(n-Propyl)-Aminomethyl]- 3-Substituted-4-[2,3,4-Trimethoxyphenyl) pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 136B | 4-(2,3,4-trimethoxyphenyl)-3-(CH$_2$OH)-5-(CH$_2$NH(CH$_2$)$_2$CH$_3$)-pyrrole-2-CN |
| 137A | 4-(2,3,4-trimethoxyphenyl)-3-(CH$_2$OCH$_3$)-5-(CH$_2$NH(CH$_2$)$_2$CH$_3$)-pyrrole-2-CO$_2$CH$_3$ |
| 137B | 4-(2,3,4-trimethoxyphenyl)-3-(CH$_2$OCH$_3$)-5-(CH$_2$NH(CH$_2$)$_2$CH$_3$)-pyrrole-2-CO$_2$CH$_2$CH$_3$ |
| 138A | 4-(2,3,4-trimethoxyphenyl)-3-(CH$_2$OCH$_3$)-5-(CH$_2$NH(CH$_2$)$_2$CH$_3$)-pyrrole-2-CO$_2$H |
| 138B | 4-(2,3,4-trimethoxyphenyl)-3-(CH$_2$OCH$_3$)-5-(CH$_2$NH(CH$_2$)$_2$CH$_3$)-pyrrole-2-CN |

TABLE 24

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 139A | 4-(2,3,4-trimethoxyphenyl)-3-(CHF$_2$)-5-(CH$_2$NH(CH$_2$)$_2$CH$_3$)-pyrrole-2-CO$_2$CH$_3$ |
| 139B | 4-(2,3,4-trimethoxyphenyl)-3-(CHF$_2$)-5-(CH$_2$NH(CH$_2$)$_2$CH$_3$)-pyrrole-2-CO$_2$CH$_2$CH$_3$ |
| 140A | 4-(2,3,4-trimethoxyphenyl)-3-(CHF$_2$)-5-(CH$_2$NH(CH$_2$)$_2$CH$_3$)-pyrrole-2-CO$_2$H |
| 140B | 4-(2,3,4-trimethoxyphenyl)-3-(CHF$_2$)-5-(CH$_2$NH(CH$_2$)$_2$CH$_3$)-pyrrole-2-CN |
| 141A | 4-(2,3,4-trimethoxyphenyl)-3-(CH=CHCO$_2$CH$_3$)-5-(CH$_2$NH(CH$_2$)$_2$CH$_3$)-pyrrole-2-CO$_2$CH$_3$ |

TABLE 24-continued

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 141B | (structure) |
| 142A | (structure) |
| 142B | (structure) |

TABLE 25

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 143A | (structure) |

TABLE 25-continued

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 143B | (structure) |
| 144A | (structure) |
| 144B | (structure) |
| 145A | (structure) |
| 145B | (structure) |

TABLE 25-continued

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 146A | (structure) |
| 146B | (structure) |

TABLE 26

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 147A | (structure) |
| 147B | (structure) |
| 148A | (structure) |
| 148B | (structure) |
| 149A | (structure) |
| 149B | (structure) |
| 150A | (structure) |

TABLE 26-continued

Unsymmetrical 5-[(n-Propyl)-Aminomethyl]-3-Substituted-4-[2,3,4-Trimethoxyphenyl)pyrrole 2-carboxylic acid esters, Unsymmetrical 5-[n-Propyl]-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 150B | [3-cyclopropyl-4-(2,3,4-trimethoxyphenyl)-5-[(n-propylamino)methyl]-1H-pyrrole-2-carbonitrile] |

TABLE 27

Unsymmetrical 5-[(n-Propyl)-Aminomethyl]-3-Substituted-4-[2,3,4-Trimethoxyphenyl)pyrrole 2-carboxylic acid esters, Unsymmetrical 5-[(n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 151A | methyl 3-(1-hydroxyethyl)-5-[(n-propylamino)methyl]-4-(2,3,4-trimethoxyphenyl)-1H-pyrrole-2-carboxylate |
| 151B | ethyl 3-(1-hydroxyethyl)-5-[(n-propylamino)methyl]-4-(2,3,4-trimethoxyphenyl)-1H-pyrrole-2-carboxylate |
| 152A | 3-(1-hydroxyethyl)-5-[(n-propylamino)methyl]-4-(2,3,4-trimethoxyphenyl)-1H-pyrrole-2-carboxylic acid |
| 152B | 3-(1-hydroxyethyl)-5-[(n-propylamino)methyl]-4-(2,3,4-trimethoxyphenyl)-1H-pyrrole-2-carbonitrile |
| 153A | methyl 3-(cyclopropyl(hydroxy)methyl)-5-[(n-propylamino)methyl]-4-(2,3,4-trimethoxyphenyl)-1H-pyrrole-2-carboxylate |
| 153B | ethyl 3-(cyclopropyl(hydroxy)methyl)-5-[(n-propylamino)methyl]-4-(2,3,4-trimethoxyphenyl)-1H-pyrrole-2-carboxylate |
| 154A | 3-(cyclopropyl(hydroxy)methyl)-5-[(n-propylamino)methyl]-4-(2,3,4-trimethoxyphenyl)-1H-pyrrole-2-carboxylic acid |
| 154B | 3-(cyclopropyl(hydroxy)methyl)-5-[(n-propylamino)methyl]-4-(2,3,4-trimethoxyphenyl)-1H-pyrrole-2-carbonitrile |

TABLE 28

Unsymmetrical 5-[(n-Propyl)-Aminomethyl]-3-Substituted-4-[2,3,4-Trimethoxyphenyl)pyrrole 2-carboxylic acid esters, Unsymmetrical 5-[(n-Propyl)-Aminomethyl]-3-Substituted-4-[2,3,4-Trimethoxyphenyl)pyrrole 2-carboxylic acids, and Unsymmetrical 2-Cyano-5-[(n-Propyl)-Aminomethyl]-3-Substituted-4-[2,3,4-Trimethoxyphenyl)pyrroles.

| Ex. No. | Structure |
|---|---|
| 155A | (structure) |
| 155B | (structure) |
| 156A | (structure) |
| 156B | (structure) |
| 157A | (structure) |
| 157B | (structure) |
| 158A | (structure) |
| 158B | (structure) |

TABLE 29

Unsymmetrical 5-[Aminomethyl]-3-Substituted-4-[2,3,4-Trimethoxyphenyl)pyrrole 2-carboxylic acid esters, Unsymmetrical 5-[Aminomethyl]-3-Substituted-4-[2,3,4-Trimethoxyphenyl)pyrrole 2-carboxylic acids, and Unsymmetrical 2-Cyano-5-[Aminomethyl]-3-Substituted]-3-Substituted-4-[2,3,4-Trimethoxyphenyl)pyrroles.

| Ex. No. | Structure |
|---|---|
| 159A | (structure) |

TABLE 29-continued

Unsymmetrical 5-[Aminomethyl]-3-Substituted-4-[2,3,4-Trimethoxyphenyl)pyrrole 2-carboxylic acid esters, Unsymmetrical 5-[Aminomethyl]-3-Substituted-4-[2,3,4-Trimethoxyphenyl)pyrrole 2-carboxylic acids, and Unsymmetrical 2-Cyano-5-[Aminomethyl]-3-Substituted]-3-Substituted-4-[2,3,4-Trimethoxyphenyl)pyrroles.

| Ex. No. | Structure |
|---|---|
| 159b | (structure) |
| 160A | (structure) |
| 160B | (structure) |
| 161A | (structure) |
| 161B | (structure) |
| 162A | (structure) |
| 162B | (structure) |

TABLE 30

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 163A | (structure) |
| 163B | (structure) |

TABLE 30-continued

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 164A | (structure) |
| 164B | (structure) |
| 165A | (structure) |
| 165B | (structure) |
| 166A | (structure) |
| 166B | (structure) |

TABLE 31

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 167A | (structure) |
| 167B | (structure) |
| 168A | (structure) |

TABLE 31-continued

Unsymmetrical 5-[O-Methyloximino]-3-Substituted-4-[2,3,4-Trimethoxy-phenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 168B | (structure) |
| 169A | (structure) |
| 169B | (structure) |
| 170A | (structure) |
| 170B | (structure) |

TABLE 32

Unsymmetrical 5-[O-Methyloximino]-3-Substituted-4-[2,3,4-Trimethoxy-phenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 171A | (structure) |
| 171B | (structure) |
| 172A | (structure) |
| 172B | (structure) |
| 173A | (structure) |

TABLE 32-continued

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl)pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 173B | (structure) |
| 174A | (structure) |
| 174B | (structure) |

TABLE 33

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 175A | (structure) |
| 175B | (structure) |
| 176A | (structure) |
| 176B | (structure) |
| 177A | (structure) |
| 177B | (structure) |

TABLE 33-continued

Unsymmetrical 5-[O-Methyloximino]-3-Substituted-4-[2,3,4-Tri-methoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 178A | (structure) |
| 178B | (structure) |

TABLE 34

Unsymmetrical 5-[O-Methyloximino]-3-Substituted-4-[2,3,4-Tri-methoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 179A | (structure) |
| 179B | (structure) |
| 180A | (structure) |
| 180B | (structure) |
| 181A | (structure) |
| 181B | (structure) |
| 182A | (structure) |

TABLE 34-continued

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 182B | (structure) |

TABLE 35

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 183A | (structure) |
| 183B | (structure) |
| 184A | (structure) |

TABLE 35-continued

Unsymmetrical 5-[O-Methyloximino]-3-Substituted-4-[2,3,4-Trimethoxyphenyl)pyrrole 2-carboxylic acid esters, Unsymmetrical 5-[O-Methyloximino]-3-Substituted-4-[2,3,4-Trimethoxyphenyl) pyrrole 2-carboxylic acids, and Unsymmetrical 2-Cyano-5-[O-Methyloximino]-3-Substituted-4-[2,3,4-Trimethoxyphenyl)pyrroles.

| Ex. No. | Structure |
|---|---|
| 184B | (structure) |
| 185A | (structure) |
| 185B | (structure) |
| 186A | (structure) |
| 186B | (structure) |

TABLE 36

Unsymmetrical 5-[Aminoethyl]-3-Substituted-4-[2,3,4-Trimethoxyphenyl)pyrrole 2-carboxylic acid esters, Unsymmetrical 5-[Aminoethyl]-3-Substituted-4-[2,3,4-Trimethoxyphenyl) pyrrole 2-carboxylic acids, and Unsymmetrical 2-Cyano-5-[Aminoethyl]-3-Substituted-4-[2,3,4-Trimethoxyphenyl)pyrroles.

| Ex. No. | Structure |
|---|---|
| 187A | 3-(CH2OH), 2-(CO2CH3), 5-(CH2CH2NH2), 4-(2,3,4-trimethoxyphenyl)pyrrole |
| 187B | 3-(CH2OH), 2-(CO2CH2CH3), 5-(CH2CH2NH2), 4-(2,3,4-trimethoxyphenyl)pyrrole |
| 188A | 3-(CH2OH), 2-(CO2H), 5-(CH2CH2NH2), 4-(2,3,4-trimethoxyphenyl)pyrrole |
| 188B | 3-(CH2OH), 2-(CN), 5-(CH2CH2NH2), 4-(2,3,4-trimethoxyphenyl)pyrrole |
| 189A | 3-(CH2OCH3), 2-(CO2CH3), 5-(CH2CH2NH2), 4-(2,3,4-trimethoxyphenyl)pyrrole |
| 189B | 3-(CH2OCH3), 2-(CO2CH2CH3), 5-(CH2CH2NH2), 4-(2,3,4-trimethoxyphenyl)pyrrole |
| 190A | 3-(CH2OCH3), 2-(CO2H), 5-(CH2CH2NH2), 4-(2,3,4-trimethoxyphenyl)pyrrole |
| 190B | 3-(CH2OCH3), 2-(CN), 5-(CH2CH2NH2), 4-(2,3,4-trimethoxyphenyl)pyrrole |

TABLE 37

Unsymmetrical 5-[Aminoethyl]-3-Substituted-4-[2,3,4-Trimethoxyphenyl)pyrrole 2-carboxylic acid esters, Unsymmetrical 5-[Aminoethyl]-3-Substituted-4-[2,3,4-Trimethoxyphenyl) pyrrole 2-carboxylic acids, and Unsymmetrical 2-Cyano-5-[Aminoethyl]-3-Substituted-4-[2,3,4-Trimethoxyphenyl)pyrroles.

| Ex. No. | Structure |
|---|---|
| 191A | 3-(C(=O)-cyclopropyl), 2-(CO2CH3), 5-(CH2NH2), 4-(2,3,4-trimethoxyphenyl)pyrrole |

TABLE 37-continued

Unsymmetrical 5-[Aminoethyl]-3-Substituted-4-[2,3,4-Trimethoxyphenyl)pyrrole 2-carboxylic acid esters, Unsymmetrical 5-[Aminoethyl]-3-Substituted-4-[2,3,4-Trimethoxyphenyl) pyrrole 2-carboxylic acids, and Unsymmetrical 2-Cyano-5-[Aminoethyl]-3-Substituted-4-[2,3,4-Trimethoxyphenyl)pyrroles.

| Ex. No. | Structure |
|---|---|
| 191B | (structure) |
| 192A | (structure) |
| 192B | (structure) |
| 193A | (structure) |
| 193B | (structure) |
| 194A | (structure) |
| 194B | (structure) |

TABLE 38

Unsymmetrical 5-[Aminoethyl]-3-Substituted-4-[2,3,4-Trimethoxyphenyl)pyrrole 2-carboxylic acid esters, Unsymmetrical 5-[Aminoethyl]-3-Substituted-4-[2,3,4-Trimethoxyphenyl) pyrrole 2-carboxylic acids, and Unsymmetrical 2-Cyano-5-[Aminoethyl]-3-Substituted-4-[2,3,4-Trimethoxyphenyl)pyrroles.

| Ex. No. | Structure |
|---|---|
| 195A | (structure) |
| 195B | (structure) |

TABLE 38-continued

Unsymmetrical 5-[Aminoethyl]-3-Substituted-4-[2,3,4-Trimethoxyphenyl)pyrrole 2-carboxylic acid esters, Unsymmetrical 5-[Aminoethyl]-3-Substituted-4-[2,3,4-Trimethoxyphenyl) pyrrole 2-carboxylic acids, and Unsymmetrical 2-Cyano-5-[Aminoethyl]-3-Substituted-4-[2,3,4-Trimethoxyphenyl)pyrroles.

| Ex. No. | Structure |
|---|---|
| 196A | (3,4-CHF$_2$ pyrrole with 2,3,4-trimethoxyphenyl at 4-position, CH$_2$CH$_2$NH$_2$ at 5-position, CO$_2$H at 2-position) |
| 196B | (3-CHF$_2$ pyrrole with 2,3,4-trimethoxyphenyl at 4-position, CH$_2$CH$_2$NH$_2$ at 5-position, C≡N at 2-position) |
| 197A | (3-cyclopropyl pyrrole with 2,3,4-trimethoxyphenyl at 4-position, CH$_2$CH$_2$NH$_2$ at 5-position, CO$_2$CH$_3$ at 2-position) |
| 197B | (3-cyclopropyl pyrrole with 2,3,4-trimethoxyphenyl at 4-position, CH$_2$CH$_2$NH$_2$ at 5-position, CO$_2$CH$_2$CH$_3$ at 2-position) |
| 198A | (3-cyclopropyl pyrrole with 2,3,4-trimethoxyphenyl at 4-position, CH$_2$CH$_2$NH$_2$ at 5-position, CO$_2$H at 2-position) |
| 198B | (3-cyclopropyl pyrrole with 2,3,4-trimethoxyphenyl at 4-position, CH$_2$CH$_2$NH$_2$ at 5-position, C≡N at 2-position) |

TABLE 39

Unsymmetrical 5-[Aminomethyl]-3-Substituted-4-[2,3,4-Trimethoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 199A | (3-CH=CH$_2$ pyrrole with 2,3,4-trimethoxyphenyl at 4-position, CH$_2$NH$_2$ at 5-position, CO$_2$CH$_3$ at 2-position) |
| 199B | (3-CH=CH$_2$ pyrrole with 2,3,4-trimethoxyphenyl at 4-position, CH$_2$NH$_2$ at 5-position, CO$_2$CH$_2$CH$_3$ at 2-position) |
| 200A | (3-CH=CH$_2$ pyrrole with 2,3,4-trimethoxyphenyl at 4-position, CH$_2$NH$_2$ at 5-position, CO$_2$H at 2-position) |

TABLE 39-continued

Unsymmetrical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 200B | (structure) |
| 201A | (structure) |
| 201B | (structure) |
| 202A | (structure) |
| 202B | (structure) |

TABLE 40

Unsymmetrical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 203A | (structure) |
| 203B | (structure) |
| 204A | (structure) |
| 204B | (structure) |
| 205A | (structure) |

TABLE 40-continued

Unsymmetrical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 205B | (structure) |
| 206A | (structure) |
| 206B | (structure) |

TABLE 41

Unsymmetrical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 207A | (structure) |

TABLE 41-continued

Unsymmetrical 5-[Aminomethyl]-3-Substituted-4-[2,3,4-Tri-methoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 207B | (structure) |
| 208A | (structure) |
| 208B | (structure) |
| 209A | (structure) |
| 209B | (structure) |

TABLE 41-continued

Unsymmetrical 5-[Aminomethyl]-3-Substituted-4-[2,3,4-Trimethoxyphenyl)pyrrole 2-carboxylic acid esters, Unsymmetrical 5-[Aminomethyl]-3-Substituted-4-[2,3,4-Trimethoxyphenyl) pyrrole 2-carboxylic acids, and Unsymmetrical 2-Cyano-5-[Aminomethyl]-3-Substituted-4-[2,3,4-Trimethoxyphenyl)pyrroles.

| Ex. No. | Structure |
|---|---|
| 210A | (structure) |
| 210B | (structure) |

TABLE 42

3,5-Dihalo-4-[2,3,4-Trimethoxyphenyl)pyrrole-2-carboxylic acids and carboxylic acid esters and 2-Cyano-3,5-Dihalo-4-[2,3,4-Trimethoxy-phenyl)-pyrroles.

| Ex. No. | Structure |
|---|---|
| 211A | (structure) |
| 211B | (structure) |

TABLE 42-continued 3,5-Dihalo-4-[2,3,4-Trimethoxyphenyl)pyrrole-2-carboxylic acids and carboxylic acid esters and 2-Cyano-3,5-Dihalo-4-[2,3,4-Trimethoxy-phenyl)-pyrroles.

| Ex. No. | Structure |
|---|---|
| 212A | (structure) |
| 212B | (structure) |
| 213A | (structure) |
| 213B | (structure) |
| 214A | (structure) |

TABLE 42-continued 3,5-Dihalo-4-[2,3,4-Trimethoxyphenyl)pyrrole-2-carboxylic acids and carboxylic acid esters and 2-Cyano-3,5-Dihalo-4-[2,3,4-Trimethoxy-phenyl)-pyrroles.

| Ex. No. | Structure |
|---|---|
| 214B | 4-(2,3,4-trimethoxyphenyl)-3,5-dibromo-1H-pyrrole-2-carboxylic acid |
| 215A | 4-(2,3,4-trimethoxyphenyl)-3-chloro-5-bromo-1H-pyrrole-2-carboxylic acid ethyl ester |
| 215B | 4-(2,3,4-trimethoxyphenyl)-3-bromo-5-chloro-1H-pyrrole-2-carboxylic acid ethyl ester |

TABLE 43

2-Substituted 3,5-Dihalo-4-[2,3,4-Trimethoxyphenyl)pyrroles.

| Ex. No. | Structure |
|---|---|
| 216A | 4-(2,3,4-trimethoxyphenyl)-3,5-dichloro-1H-pyrrole-2-carbohydroxamic acid |
| 216B | 4-(2,3,4-trimethoxyphenyl)-3-bromo-5-chloro-1H-pyrrole-2-carbohydroxamic acid |
| 217A | 4-(2,3,4-trimethoxyphenyl)-3,5-dichloro-2-(1H-tetrazol-5-yl)-1H-pyrrole |
| 217B | 4-(2,3,4-trimethoxyphenyl)-3-bromo-5-bromo-2-(1H-tetrazol-5-yl)-1H-pyrrole |
| 218A | 4-(2,3,4-trimethoxyphenyl)-3,5-dichloro-2-(1H-pyrrol-2-yl)-1H-pyrrole |
| 218B | 4-(2,3,4-trimethoxyphenyl)-3,5-dibromo-2-(1H-pyrrol-2-yl)-1H-pyrrole |

TABLE 43-continued

2-Substituted 3,5-Dihalo-4-[2,3,4-Trimethoxyphenyl)pyrroles.

| Ex. No. | Structure |
|---|---|
| 219A | (3,5-dichloro-4-(2,3,4-trimethoxyphenyl)-1H-pyrrol-2-yl)-4H-1,2,4-triazole |
| 219B | (3,5-dibromo-4-(2,3,4-trimethoxyphenyl)-1H-pyrrol-2-yl)-4H-1,2,4-triazole |
| 220A | (3,5-dichloro-4-(2,3,4-trimethoxyphenyl)-1H-pyrrol-2-yl)-1H-imidazole |
| 220B | (3,5-dibromo-4-(2,3,4-trimethoxyphenyl)-1H-pyrrol-2-yl)-1H-imidazole |

TABLE 44

2-Substituted 3,5-Dihalo-4-[2,3,4-Trimethoxyphenyl)pyrroles.

| Ex. No. | Structure |
|---|---|
| 221A | 3,5-dichloro-4-(2,3,4-trimethoxyphenyl)-2-(methylsulfonyl)-1H-pyrrole |
| 221B | 3,5-dibromo-4-(2,3,4-trimethoxyphenyl)-2-(methylsulfonyl)-1H-pyrrole |
| 222A | 3,5-dichloro-4-(2,3,4-trimethoxyphenyl)-1H-pyrrole-2-sulfonamide |
| 222B | 3,5-dibromo-4-(2,3,4-trimethoxyphenyl)-1H-pyrrole-2-sulfonamide |
| 223A | 1-(3,5-dichloro-4-(2,3,4-trimethoxyphenyl)-1H-pyrrol-2-yl)ethanone |

TABLE 44-continued

2-Substituted 3,5-Dihalo-4-[2,3,4-Trimethoxyphenyl)pyrroles.

| Ex. No. | Structure |
|---|---|
| 223B | 3,5-dibromo-4-(2,3,4-trimethoxyphenyl)-pyrrole with 2-COCH₃ |
| 224A | 3,5-dichloro-4-(2,3,4-trimethoxyphenyl)-pyrrole with 2-COCH₂CH₃ |
| 224B | 3,5-dibromo-4-(2,3,4-trimethoxyphenyl)-pyrrole with 2-COCH₂CH₃ |
| 225A | 3,5-dichloro-4-(2,3,4-trimethoxyphenyl)-pyrrole with 2-COCO₂CH₃ |
| 225B | 3,5-dibromo-4-(2,3,4-trimethoxyphenyl)-pyrrole with 2-COCO₂CH₃ |

TABLE 45

2-Substituted 3,5-Dihalo-4-[2,3,4-Trimethoxyphenyl)pyrroles.

| Ex. No. | Structure |
|---|---|
| 226A | 3,5-dichloro-4-(2,3,4-trimethoxyphenyl)-pyrrole with 2-(imidazol-2-ylcarbonyl) |
| 226B | 3,5-dibromo-4-(2,3,4-trimethoxyphenyl)-pyrrole with 2-(imidazol-2-ylcarbonyl) |
| 227A | 3,5-dichloro-4-(2,3,4-trimethoxyphenyl)-pyrrole with 2-(pyrrol-2-ylcarbonyl) |
| 227B | 3,5-dibromo-4-(2,3,4-trimethoxyphenyl)-pyrrole with 2-(pyrrol-2-ylcarbonyl) |

TABLE 46

N-Substituted 3,5-Dihalo-4-[2,3,4-Trimethoxyphenyl)pyrrole-2-carboxylic acid esters and N-Substituted 2-Cyano-3,5-Dihalo-4-[2,3,4-Trimethoxy-phenyl)-pyrroles.

| Ex. No. | Structure |
|---|---|
| 228A | 3,5-dichloro-4-(2,3,4-trimethoxyphenyl)-1-hydroxy-pyrrole-2-carbonitrile |
| 228B | 3,5-dibromo-4-(2,3,4-trimethoxyphenyl)-1-hydroxy-pyrrole-2-carbonitrile |
| 229A | 3,5-dichloro-4-(2,3,4-trimethoxyphenyl)-1-methoxy-pyrrole-2-carbonitrile |
| 229B | 3,5-dibromo-4-(2,3,4-trimethoxyphenyl)-1-methoxy-pyrrole-2-carbonitrile |
| 230A | ethyl 3,5-dichloro-4-(2,3,4-trimethoxyphenyl)-1-hydroxy-pyrrole-2-carboxylate |
| 230B | ethyl 3,5-dibromo-4-(2,3,4-trimethoxyphenyl)-1-hydroxy-pyrrole-2-carboxylate |
| 231A | ethyl 3,5-dichloro-4-(2,3,4-trimethoxyphenyl)-1-methoxy-pyrrole-2-carboxylate |
| 231B | ethyl 3,5-dibromo-4-(2,3,4-trimethoxyphenyl)-1-methoxy-pyrrole-2-carboxylate |
| 232A | ethyl 3,5-dichloro-4-(2,3,4-trimethoxyphenyl)-1-(carboxymethoxy)-pyrrole-2-carboxylate |
| 232B | ethyl 3,5-dibromo-4-(2,3,4-trimethoxyphenyl)-1-(carboxymethoxy)-pyrrole-2-carboxylate |

TABLE 47

N-Substituted 3,5-Dihalo-4-[2,3,4-Trimethoxyphenyl)pyrrole-2-carboxylic acid esters and N-Substituted 2-Cyano-3,5-Dihalo-4-[2,3,4-Trimethoxy-phenyl)-pyrroles.

| Ex. No. | Structure |
|---|---|
| 233A | 3,5-dichloro-4-(2,3,4-trimethoxyphenyl)-1-(ethoxycarbonylmethyl)pyrrole-2-carboxylic acid ethyl ester |
| 233B | 3,5-dibromo-4-(2,3,4-trimethoxyphenyl)-1-(ethoxycarbonylmethyl)pyrrole-2-carboxylic acid ethyl ester |
| 234A | 3,5-dichloro-4-(2,3,4-trimethoxyphenyl)-1-(methoxycarbonylmethyl)pyrrole-2-carboxylic acid methyl ester |
| 234B | 3,5-dibromo-4-(2,3,4-trimethoxyphenyl)-1-(methoxycarbonylmethyl)pyrrole-2-carboxylic acid methyl ester |
| 235A | 3,5-dichloro-4-(2,3,4-trimethoxyphenyl)-1-(cyanomethyl)pyrrole-2-carboxylic acid ethyl ester |
| 235B | 3,5-dibromo-4-(2,3,4-trimethoxyphenyl)-1-(cyanomethyl)pyrrole-2-carboxylic acid ethyl ester |
| 236A | 2-cyano-3,5-dichloro-4-(2,3,4-trimethoxyphenyl)-1-(cyanomethyl)pyrrole |
| 236B | 2-cyano-3,5-dibromo-4-(2,3,4-trimethoxyphenyl)-1-(cyanomethyl)pyrrole |
| 237A | 3,5-dichloro-4-(2,3,4-trimethoxyphenyl)-1-methylpyrrole-2-carboxylic acid ethyl ester |
| 237B | 3,5-dibromo-4-(2,3,4-trimethoxyphenyl)-1-methylpyrrole-2-carboxylic acid ethyl ester |

Example 24

In Vitro Cell Culture Assays

Cell Culture. Various representative cancer and other cell lines were sourced and grown as described previously [Mooberry, S. L., et al., Mol. Pharm. 72, 132-140 (2007)]. MDA-MB-435 (human melanoma cancer cells), and MDA-MB-231 (human breast cancer cells) were grown in IMEM Richter's Medium (Life Technologies, Grand Island, N.Y.) with 10% FBS (Hyclone, Logan, Utah) and 25 µg/mL gentamicin sulfate (Life Technologies). A-10 (embryonic rat vascular smooth muscle cells) and HeLa (human cervical cancer cells), SK-OV-3 (human ovarian cancer cells) and SK-OV-3-MDR-1-M6/6 (a clone of the SK-OV-3 that was generated from SK-OV-3 cells by adenovirus-mediated expression of MDR1) were grown in Basal Medium Eagle (BME, Sigma-Aldrich, St. Louis, Mo.) containing Earle's salts, 50 µg/ml gentamicin sulfate, and 10% FBS. HeLa cells (a single-cell clone derived from transduction of HeLa cells with wild-type (WT) βIII-tubulin) were grown in Dulbecco's Modified Eagle's Medium (DMEM, Life Technologies) containing 50 µg/mL gentamicin sulfate and 10% FBS.

Example 25

In Vitro Cellular Cytotoxicity Evaluations

Antiproliferative Effects. The pyrrole compounds were evaluated for their antiproliferative effects in a panel of cancer cell lines. Cells were plated into 96-well plates at predetermined densities and allowed to attach and proliferate for 24 hr, and then the compounds were added. After a 48 hr exposure to the compounds, the cells were fixed with trichloroacetic acid and cellular protein was determined using the sulforhodamine B (SRB) assay (Skehan et al., J. Natl. Cancer Inst. 82, 1107-12, (1990); Boyd and Paull Drug Devel. Res. 34, 91-109, (1995)). Concentration response curves were constructed, and the $IC_{50}$ (the concentration required to inhibit proliferation by 50%) values were determined from the linear portions of the log concentration-response curves as described previously [Tinley, T. L., et al., Cancer Res. 63, 3211-3220, (2003)] as shown in Table 48.

TABLE 48

Antiproliferative Effects of Select Unsymmetrical Poly-Substituted 4-(2,3,4-Trimethoxy)phenyl-Pyrrole Compounds in a Spectrum of Representative Human Cancer Cell Lines.

| Ex. No. | Compound | MDA-MB-435 Anti-Proliferative Activity[a], $IC_{50}$ (nM) | HeLa Anti-Proliferative Activity[a], $IC_{50}$ (nM) | SK-OV-3 Anti-Proliferative Activity[a], $IC_{50}$ (nM) |
|---|---|---|---|---|
| 2 | NT-7-30 | 57.0 ± 5.0 | 31.7 ± 4.8 | 72.0 ± 9.1 |
| 3 | KL-4-44 | 64.0 ± 8.5 | 43.5 ± 1.7 | 67.8 ± 16.2 |
| 4 | NT-9-3 | 76.0 ± 0.6 | 39.9 ± 3.1 | 66.9 ± 5.8 |
| 5 | AH-3-19 | 25.7 ± 0.8 | 33.4 ± 0.8 | 37.4 ± 1.3 |
| 6 | NT-7-31 | 112.6 ± 6.0 | 141.7 ± 11.0 | 226.7 ± 14.0 |
| 7 | MW-4-62 | 17.6 ± 1.0 | 23.8 ± 1.7 | 26.6 ± 1.1 |
| 8a | NT-8-77; fr-4 | 23.9 ± 1.2 | 14.8 ± 0.2 | 16.4 ± 0.9 |
| 8b | NT-8-77; fr-6 | 9.3 ± 0.3 | 10.9 ± 0.3 | 22.3 ± 0.5 |
| 9 | NT-7-43 | 1,533 ± 89.0 | 2,335 ± 171.0 | ND |
| 10a | NT-7-45 E&Z | 2.7 ± 0.2 | 5.0 ± 0.3 | 5.3 ± 0.2 |
| 10b | NT8-6; fr-6-7 | 25.3 ± 3.1 | 29.4 ± 1.0 | 33.7 ± 1.3 |
| 10e | NT-8-6; fr-8 | 14.0 ± 0.8 | 18.0 ± 0.9 | 23.1 ± 0.5 |
| 11 | KL-3-95 | 19.6 ± 1.8 | 20.6 ± 1.9 | 26.2 ± 2.1 |
| 12 | NT-7-46 | 7.6 ± 0.5 | 11.9 ± 1.3 | 13.8 ± 0.9 |
| 13 | NT-9-44 | 15.8 ± 0.9 | 19.5 ± 0.6 | 23.1 ± 1.8 |
| 14 | NT-9-46 | 13.0 ± 0.4 | 15.0 ± 0.5 | 27.8 ± 1.3 |
| 15 | NT-9-43 | 168.5 ± 14.6 | 196.3 ± 19.5 | 268.8 ± 4.4 |
| 16 | NT-9-49 | 74.6 ± 7.9 | 66.7 ± 7.2 | 161.2 ± 8.7 |
| 17 | NT-9-33 | 2,633.3 ± 208.2 | 2,453.0 ± 283.8 | 3,017.0 ± 374.8 |
| 18 | NT-9-37 | 12.6 ± 0.4 | 14.3 ± 0.8 | 20.7 ± 1.9 |
| 19 | NT-9-56 | ND | ND | ND |
| 20 | NT-9-42 | ND | ND | ND |
| 21 | NT-9-24 | 87.7 ± 10.0 | 122.7 ± 6.5 | 174.7 ± 30.4 |
| 22 | NT-7-16 | 10.4 ± 0.5 | 12.9 ± 0.8 | 15.2 ± 0.8 |
| 23 | NT-9-21 | 116 ± 4.3 | 131 ± 8.0 | 211 ± 64.9 |
| paclitaxel | | 2.0 ± 0.1 | 1.5 ± 0.05 | 3.0 ± 0.3 |

[a]Cells were exposed to compound for 48 hr and antiproliferative activities were determined using the SRB assay.
ND = not determined.

Example 26

Compound Effects in Drug-Resistant Cell Lines

The ability of representative compounds to overcome two types of drug resistance was demonstrated. First, drug resistance mediated by the expression of βIII tubulin was evaluated in an isogenic HeLa cell line pair. Expression of the βIII tubulin isotype is associated with clinical drug resistance to the taxanes in ovarian cancer, non small-cell lung cancer and breast cancer [Galmarini, C. M., et al., Clin. Cancer Res. 14, 4511-4516 (2008)]. Secondly, drug resistance mediated by the expression of the drug efflux pump protein, Pgp, was evaluated in the isogenic SK-OV-3 cell line pair. The expression of Pgp can lead to lower intracellular drug concentrations and diminished cytotoxic effects both in vitro and in vivo. All tubulin-binding anticancer drugs used currently in the clinic, except cabazitaxel, are substrates for Pgp, thus limiting their utility in drug resistant tumors [Penson, R. T., et al., *Gynecol. Oncol.* 93, 98-106 (2004)]. Differences in sensitivity between the parent and transformed cell line, indicative of resistance, was determined by calculating relative resistance (Rr) values in the two pairs of isogenic cell lines (dividing the $IC_{50}$ of the expressing cell line by the $IC_{50}$ of the parental cell line). Results are shown in Table 49.

visualized with DAPI. A representative concentration response curve for NT-7-16 is also shown in FIG. 1 that was used to calculate its corresponding $EC_{50}$ for microtubule loss. Concentration response curves for microtubule loss were plotted using data from at least three experiments for each compound and the corresponding $EC_{50}$ values for microtubule loss are presented in Table 50.

TABLE 49

Antiproliferative Effects [a] of Select Poly-Substituted 4-(2,3,4-Trimethoxy)phenyl-Pyrrole Compounds in Two Representative Drug-Sensitive and Drug-Resistant Human Cancer Cell Line Isogenic Pairs.

| Example Number | HeLa $IC_{50}$ (nM) | HeLa WT-β-III $IC_{50}$ (nM) | Rr (β-III) | SK-OV-3 $IC_{50}$ (nM) | SK-OV-3-MDR-1-6/6 $IC_{50}$ (nM) | Rr (Pgp) |
|---|---|---|---|---|---|---|
| 2 | 31.7 ± 4.8 | 104.3 ± 6.5 | 3.3 | 72.0 ± 9.1 | 82.2 ± 9.4 | 1.1 |
| 3 | 43.5 ± 1.7 | 105.7 ± 6.6 | 2.4 | 67.8 ± 16.2 | 76.0 ± 22.9 | 1.1 |
| 4 | 39.9 ± 3.1 | 100.0 ± 2.0 | 2.5 | 66.9 ± 5.8 | 87.0 ± 23.6 | 1.3 |
| 5 | 33.4 ± 0.8 | 27.4 ± 3.1 | 0.8 | 37.4 ± 1.3 | 46.6 ± 2.1 | 1.2 |
| 6 | 141.7 ± 11.0 | 184.0 ± 30.3 | 1.3 | 226.7 ± 14.0 | 174.0 ± 12.5 | 0.8 |
| 7 | 23.8 ± 1.7 | 20.5 ± 0.8 | 0.9 | 26.6 ± 1.1 | 28.1 ± 1.9 | 1.1 |
| 8a | 14.8 ± 0.2 | 26.0 ± 1.0 | 1.8 | 16.4 ± 0.9 | 10.4 ± 0.9 | 0.6 |
| 8b | 10.9 ± 0.3 | 19.4 ± 0.4 | 1.8 | 22.3 ± 0.5 | 26.7 ± 0.3 | 1.2 |
| 9 | 2,335 ± 171.0 | ND | ND | ND | ND | ND |
| 10a | 5.0 ± 0.3 | 4.1 ± 1.0 | 0.9 | 5.3 ± 0.2 | 6.6 ± 1.2 | 1.2 |
| 10b | 29.4 ± 1.0 | 31.3 ± 0.5 | 1.1 | 33.7 ± 1.3 | 49.6 ± 2.4 | 1.5 |
| 10c | 18.0 ± 0.9 | 25.0 ± 1.4 | 1.4 | 23.1 ± 0.5 | 41.6 ± 1.9 | 1.8 |
| 11 | 20.6 ± 1.9 | 26.1 ± 0.8 | 1.3 | 26.2 ± 2.1 | 42.2 ± 5.5 | 1.6 |
| 12 | 11.9 ± 1.3 | 12.5 ± 0.2 | 1.1 | 13.8 ± 0.9 | 17.5 ± 1.2 | 1.3 |
| 13 | 19.5 ± 0.6 | 15.6 ± 0.4 | 0.8 | 23.1 ± 1.8 | 22.4 ± 0.9 | 1.0 |
| 14 | 15.0 ± 0.5 | 12.3 ± 0.3 | 0.8 | 27.8 ± 1.3 | 23.6 ± 1.0 | 0.8 |
| 15 | 196.3 ± 19.5 | 135.6 ± 8.4 | 0.7 | 268.8 ± 4.4 | 357.8 ± 12.2 | 1.3 |
| 16 | 66.7 ± 7.2 | 67.8 ± 4.3 | 1.0 | 161.2 ± 8.7 | 185.3 ± 14.7 | 1.1 |
| 17 | 2,453.0 ± 283.8 | 2,007.6 ± 373.2 | 0.8 | 3,017.0 ± 374.8 | 3,566.1 ± 152.8 | 1.2 |
| 18 | 14.3 ± 0.8 | 11.2 ± 0.4 | 0.8 | 20.7 ± 1.9 | 19.0 ± 1.0 | 0.9 |
| 19 | ND | ND | ND | ND | ND | ND |
| 20 | ND | ND | ND | ND | ND | ND |
| 21 | 122.7 ± 6.5 | 108.7 ± 9.5 | 0.9 | 174.7 ± 30.4 | 419.0 ± 30.4 | 1.9 |
| 22 | 12.9 ± 0.8 | 15.7 ± 0.2 | 1.2 | 15.2 ± 0.8 | 10.6 ± 0.3 | 0.7 |
| 23 | 131 ± 8.0 | 137 ± 15.5 | 1.0 | 211 ± 64.9 | 231 ± 118.0 | 1.1 |
| Paclitaxel | 1.5 ± 0.05 | 21.1 ± 1.8 | 14.1 | 3.0 ± 0.3 | 2,327 ± 155 | 776 |

[a] Cells were exposed to compound for 48 hr and antiproliferative activities were determined using the SRB assay.

These data clearly demonstrate that many of these unsymmetrical polysubstituted 4-(2,3,4-trimethoxy)-phenyl-pyrrole compounds exhibit low nanomolar potency and overcome clinically relevant mechanisms of drug resistance in vitro, as indicated by their Rr values.

Example 27

Compound Effects on Cellular Microtubules

The effects of representative compounds on cellular microtubules were evaluated in A-10 (embryonic rat vascular smooth muscle cell line) cells using indirect immunofluorescence techniques as previously described (Tinley et al., *Cancer Res.* 63, 3211-20 (2003)). Cells were visualized using a Nikon Eclipse 80i fluorescence microscope and NIS Elements software. Changes in both interphase and mitotic microtubules were noted and photographed. The $EC_{50}$ values, the concentration that causes approximately 50% loss of interphase microtubules was determined by evaluating a range of concentrations of each compound and the percent cellular microtubule depolymerization that was observed visually at each concentration was noted.

A-10 cells were treated with 15 nM CA-4, 5 μM paclitaxel, 10 nM NT-7-16 or vehicle (DMSO) for 6 hours (FIG. 1). Microtubules were visualized by indirect immunofluorescence using a β-tubulin antibody, and the DNA was

TABLE 50

The Ability of Representative Unsymmetrical Polysubstituted 4-(2,3,4-trimethoxyphenyl)-Pyrrole Compounds to Cause Microtubule Loss in A-10 Cells Using Indirect Immunofluorescence.

| Ex. No. | Compound | $EC_{50}$ Values (nM) for Microtubule Loss in A-10 cells |
|---|---|---|
| 2 | NT-7-30 | 66 |
| 3 | KL-4-44 | 107 |
| 4 | NT-9-3 | 129 |
| 5 | AH-3-19 | 76 |
| 6 | NT-7-31 | 315 |
| 7 | MW-4-62 | 54 |
| 8a | NT-8-77; fr-4 | 55 |
| 8b | NT-8-77; fr-6 | 24 |
| 9 | NT-7-43 | 4,600 |
| 10a | NT-7-45 E&Z | 9.8 |
| 10b | NT8-6; fr-6-7 | 107.5 |
| 10c | NT-8-6; fr-8 | 56.2 |
| 11 | KL-3-95 | 88.1 |
| 12 | NT-7-46 | 22 |
| 13 | NT-9-44 | 36 |
| 14 | NT-9-46 | 35 |
| 15 | NT-9-43 | 470 |
| 16 | NT-9-49 | 240 |
| 17 | NT-9-33 | 4,900 |
| 18 | NT-9-37 | 31 |
| 21 | NT-9-24 | 170 |
| 22 | NT-7-16 | 34.5 |
| 23 | NT-9-21 | 1,060 |

The effects of NT-7-16 on mitotic spindles were evaluated in HeLa cells by indirect immunofluorescence. HeLa cells were treated for 18 h with (A) vehicle (DMSO), (B) 15 nM NT-7-16 or (C) 25 nM NT-7-16. NT-7-16 was found to cause aberrant mitotic spindles and inhibition of the normal metaphase alignment of DNA. These effects are consistent with the actions of other microtubule disrupting agents. The presence of lagging chromosomes is indicated by the arrows and is caused by disruption of normal microtubule dynamics.

Figure 3A:
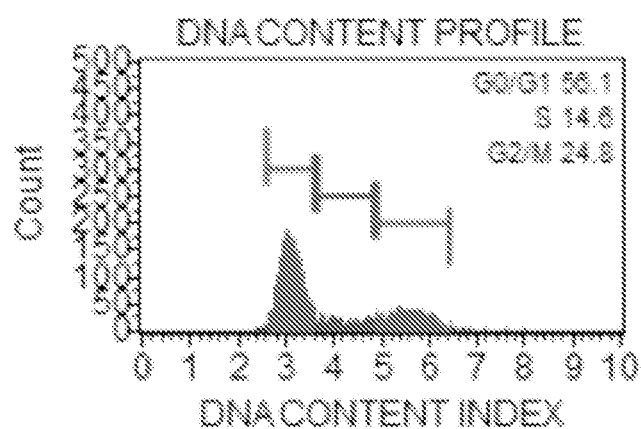
FIG. 3 shows cell cycle distribution profiles of HeLa cells treated with vehicle (A), 12.5 nM of paclitaxel (B), or 25 nM of NT-7-16 (C). Treatment with NT-7-16 caused $G_2$/M arrest, consistent with the effects of paclitaxel.
Figure 3B:
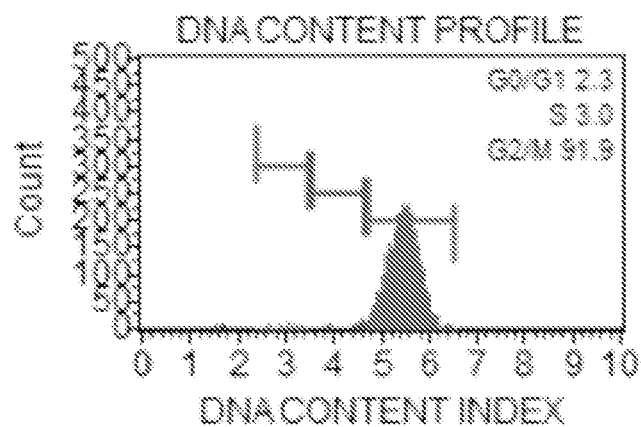
Figure 3C:
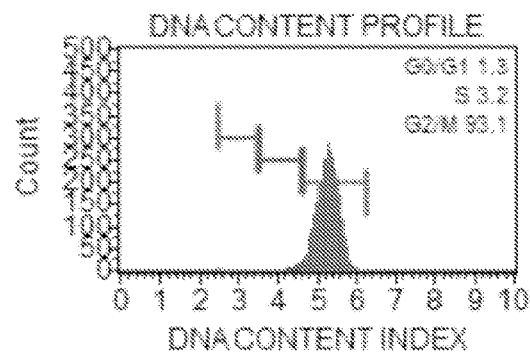

The effects of NT-7-16 on cell cycle distribution were determined. HeLa cells were treated for 18 hr with a range of concentrations of NT-7-16 or paclitaxel as a positive control. The cells were stained with Kirshan's reagent (Kirshan, Cell Biol. 66, 188-93 (1975)), and cell cycle distribution was measured using a Millipore Muse flow cytometer. The results are shown in FIG. 3. A normal cell cycle distribution was seen in vehicle-treated cells while both NT-7-16 and paclitaxel initiated mitotic accumulation. The ability of NT-7-16 to initiate aberrant mitotic spindles prevents normal mitosis leading to mitotic arrest.

Figure 2:
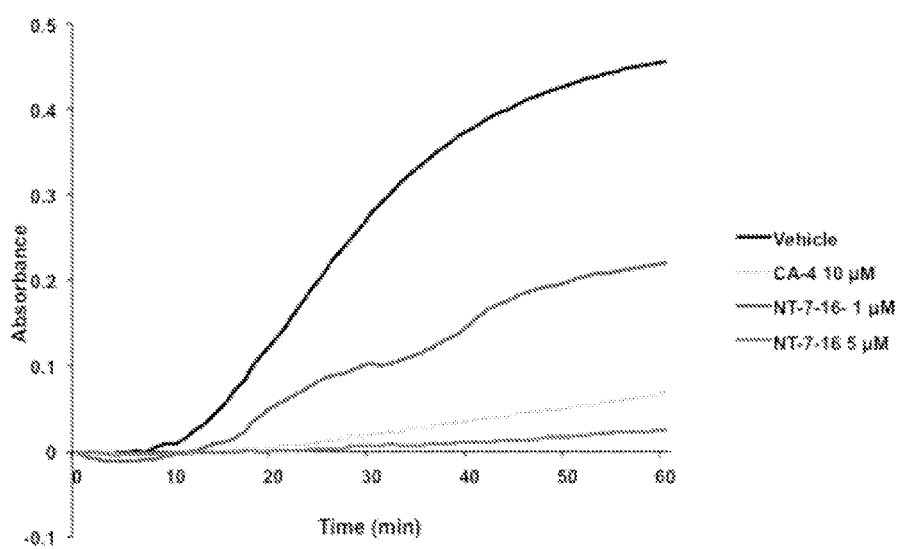
FIG. 2 is a graph depicting changes in turbidity measurements by optical absorbance of purified tubulin at 340 nm when treated with vehicle, 10 μM of CA-4, 1 μM of NT-7-16, or 5 μM of NT-7-16, demonstrating that NT-7-16 interacts with tubulin and inhibits tubulin polymerization.

The ability of NT-7-16 to directly inhibit the polymerization of purified tubulin was evaluated using a method described previously (Hartley et al., Mol. Pharmacol. 81, 431-39 (2012)). The data for NT-7-16 (FIG. 2) and NT-7-45 (FIG. 10) show that these compounds and related analogs caused concentration-dependent inhibition of tubulin assembly, indicating a direct interaction with tubulin. At 1 μM, NT-7-16 inhibited 53% of tubulin polymerization, whereas combretastatin A-4 (CA-4) at 2 μM provided only 16% inhibition of tubulin polymerization. Thus, NT-7-16 and NT-7-45 are significantly more potent than CA-4 and are highly effective, providing almost total inhibition of tubulin assembly at concentrations of 2-5 μM under these conditions.

Figure 10A:
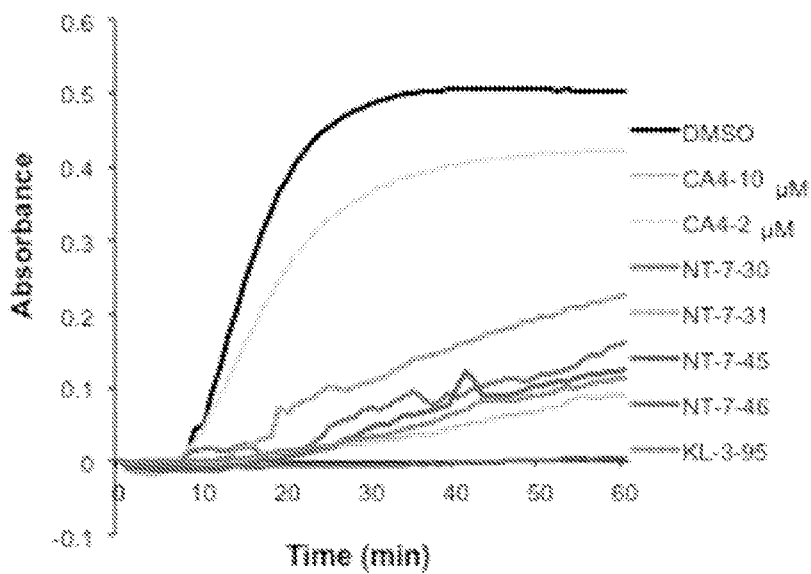
FIG. 10 is a graph depicting changes in turbidity measurements by optical absorbance of purified tubulin at 340 nm when treated with vehicle, 2 μM of CA-4, 10 μM of CA-4, or 2 μM of several representative unsymmetrical polysubstituted 4-(2,3,4-trimethoxy)phenyl-pyrrole compounds demonstrating that NT-7-45 and related analogs interact with tubulin and inhibit tubulin polymerization.
Figure 10B:
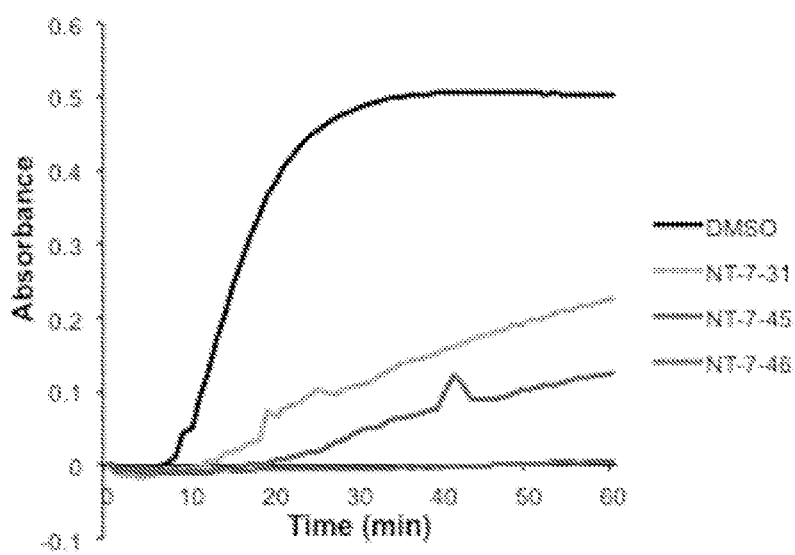

FIG. 10 shows that NT-7-45 and related analogs caused a concentration-dependent inhibition of tubulin assembly, indicating a direct interaction with tubulin. At 2 μM, NT-7-45 inhibited 75% of tubulin polymerization, whereas combretastatin A-4 (CA-4) at 2 μM provided only 16% inhibition of tubulin polymerization. Thus, NT-7-45 is significantly more potent than CA-4 and is highly effective, providing almost total inhibition of tubulin assembly at concentrations of 2-5 μM under these conditions. Data for inhibition of polymerization with purified tubulin with various unsymmetrical polysubstituted pyrrole compounds are summarized in Table 51.

TABLE 51

The Ability of Representative Unsymmetrical Polysubstituted 4-(2,3,4-trimethoxyphenyl)-Pyrrole Compounds to Inhibit Polymerization of Purified Porcine Brain Tubulin.[a]

| Ex. No. | Compound & Concentration | % Inhibition of Tubulin Polymerization |
| --- | --- | --- |
| 2 | NT-7-30 (2 μM) | 68 |
| 6 | NT-7-31 (2 μM) | 55 |
| 10a | NT-7-45 E&Z (2 μM) | 75 |
| 11 | KL-3-95 (2 μM) | 78 |
| 12 | NT-7-46 (2 μM) | 99 |
| 22 | NT-7-16 (1 μM) | 53 |
|  | CA-4 (2 μM) | 16 |
|  | CA-4 (10 μM) | 82 |

[a]Interaction with purified porcine tubuin monitored by absorbance at 340 nm, after incubation with compound.

A comparison of these cumulative in vitro data with those reported for JG-03-14 and its related 4-(3,4,5-trimethoxyphenyl)pyrrole analog (Da et al., Med. Chem. Commun. 4, 417-21 (2013)) clearly demonstrate that many of these unsymmetrical polysubstituted 4-(2,3,4-trimethoxy)phenyl-pyrrole compounds exhibit superior antiproliferative and cytotoxic potency as well as nearly 10- to 15-fold better tubulin polymerization activity compared to JG-03-14 and vastly superior activity compared to the related 4-(3,4,5-trimethoxyphenyl)pyrrole analog as summarized in Tables 52 and 53.

TABLE 52

Comparative $IC_{50}$ and $EC_{50}$ Activities of Representative Unsymmetrical Polysubstituted 4-(2,3,4-Trimethoxyphenyl)-pyrrole Compounds with JG-03-14 and JG-03-14 Analogs.

| Ex. No. | Compound | MDA-MB-435 Anti-Proliferative Activity[a], $IC_{50}$ (nM) | $EC_{50}$ Values (nM) for Microtubule Loss in A-10 cells | $EC_{50}/IC_{50}$ |
| --- | --- | --- | --- | --- |
| 2 | NT-7-30 | 57.0 ± 5.0 | 66 | 1.2 |
| 3 | KL-4-44 | 64.0 ± 8.5 | 107 | 1.7 |
| 4 | NT-9-3 | 76.0 ± 0.6 | 129 | 1.7 |
| 5 | AH-3-19 | 25.7 ± 0.8 | 76 | 3.0 |
| 6 | NT-7-31 | 112.6 ± 6.0 | 315 | 2.8 |
| 7 | MW-4-62 | 17.6 ± 1.0 | 54 | 2.3 |
| 8a | NT-8-77; fr-4 | 23.9 ± 1.2 | 55 | 2.3 |
| 8b | NT-8-77; fr-6 | 9.3 ± 0.3 | 24 | 2.6 |
| 9 | NT-7-43 | 1,533 ± 89.0 | 4,600 | 3 |
| 10a | NT-7-45 E&Z | 2.7 ± 0.2 | 8.9 | 3.3 |
| 10b | NT8-6; fr-6-7 | 25.3 ± 3.1 | 107.5 | 4.2 |
| 10c | NT-8-6; fr-8 | 14.0 ± 0.8 | 56.2 | 4 |
| 11 | KL-3-95 | 19.6 ± 1.8 | 88.1 | 4.5 |
| 12 | NT-7-46 | 7.6 ± 0.5 | 22 | 2.9 |
| 13 | NT-9-44 | 15.8 ± 0.9 | 36 | 2.3 |
| 14 | NT-9-46 | 13.0 ± 0.4 | 35 | 2.7 |
| 15 | NT-9-43 | 168.5 ± 14.6 | 470 | 2.8 |
| 16 | NT-9-49 | 74.6 ± 7.9 | 240 | 3.6 |
| 17 | NT-9-33 | 2,633.3 ± 208.2 | 4,900 | 1.9 |
| 18 | NT-9-37 | 12.6 ± 0.4 | 31 | 2.5 |
| 21 | NT-9-24 | 87.7 ± 10.0 | 170 | 1.9 |

The significantly lower $EC_{50}/IC_{50}$ ratio exhibited by many of these unsymmetrical polysubstituted 4-(2,3,4-trimethoxy)phenyl-pyrrole compounds clearly demonstrates that most, if not all, of their antiproliferative in vitro activity can be attributed to their ability to inhibit microtubule-dependent processes. Many of these $EC_{50}/IC_{50}$ ratios are comparable to those of colchicine. In contrast, JG-03-14 and its corresponding 4-(3,4,5-trimethoxyphenyl) analog are significantly less potent as microtubule depolymerizing agents. Consequently, the antiproliferative activities displayed by JG-03-14 and its corresponding 4-(3,4,5-trimethoxyphenyl) analog can only be partially attributed to microtubule depolymerization. Thus, the 4-(2,3,4-trimethoxyphenyl)pyrrole moiety provides a unique and unexpected activity advantage over other substituted 4-phenyl-pyrrole analogs.

TABLE 53

Comparative Literature $IC_{50}$ and $EC_{50}$ Values of Colchicine, JG-03-14 and the Related 4-(3,4,5-Trimethoxyphenyl-Pyrrole Analog.

| Compound | MDA-MB-435 Antiproliferative $IC_{50}$ (μM) | Microtubule Depolymerization $EC_{50}$ (μM) | $EC_{50}/IC_{50}$ |
| --- | --- | --- | --- |
| NT-7-16 | 0.014 ± 0.005 | 0.345 | 3.3 |
| NT-7-45 | 0.0027 ± 0.0002 | 0.0089 | 3.3 |
| JG-03-14[a] | 0.036 ± 0.002 | 0.490 | 13.6 |
| 4-(3,4,5-trimethoxyphenyl) pyrrole analog[a] | 12.9 ± 1.9 | >75 | >5.8 |
| colchicine[a] | 0.016 ± 0.002 | 0.030 | 1.9 |

[a]Literature data from Da, C., et al., Med. Chem. Commun. 4, 417-421 (2013).

Example 28

Cellular Antimitotic Effects

The effects of NT-7-16 on cell cycle distribution were determined. HeLa cells were treated for 18 hr with a range of concentrations of NT-7-16 or paclitaxel as a positive control. The cells were stained with Kirshan's reagent (Kirshan Cell Biol. 66, 188-93. (1975)), and cell cycle distribution was measured using a Millipore Muse flow cytometer. The results are shown in FIG. 3. A normal cell cycle distribution was seen in vehicle-treated cells while both NT-7-16 and paclitaxel initiated mitotic accumulation. The ability of NT-7-16 to initiate aberrant mitotic spindles prevents normal mitosis leading to mitotic arrest.

Example 29

Colchicine Site Binding

Figure 9:
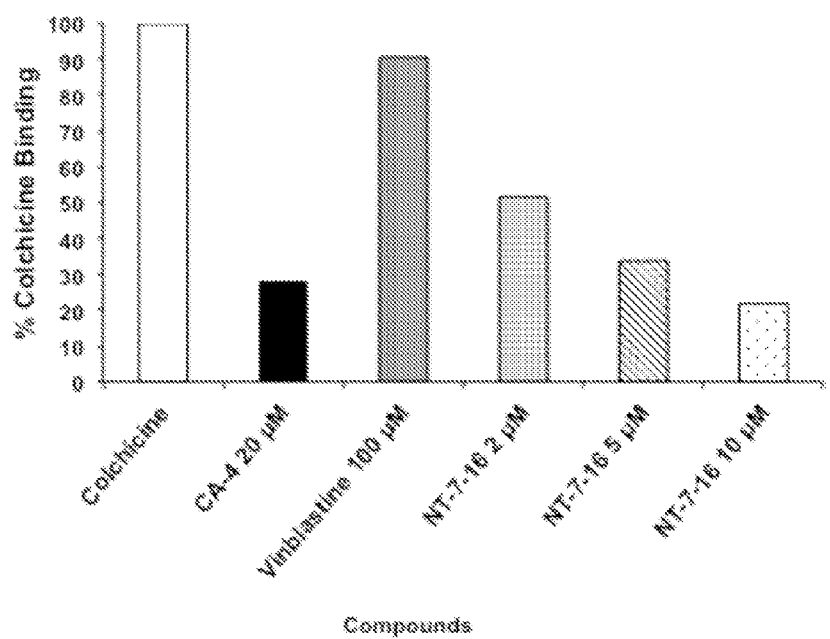
FIG. 9 shows concentration-dependent effects of NT-7-16 on colchicine binding was evaluated by a fluorometric assay. The positive control combretastatin A-4 (CA-4) inhibits colchicine binding while the negative control vinblastine does not. NT-7-16 caused concentration dependent inhibition of colchicine binding to tubulin, consistent with competition for the colchicine binding site on tubulin.

NT-7-16 was specifically designed to interact optimally within the colchicine-binding site on tubulin, a well-described site of binding for microtubule depolymerizing agents. The binding site of NT-7-16 was probed by evaluating the ability of the compound to prevent colchicine binding (FIG. 9). The results (FIG. 9) show that at 10 μM the known colchicine site agent combretastatin A-4 (CA-4) was able to inhibit almost 80% of the colchicine binding to tubulin, but that 100 μM of vinblastine, which binds to the other microtubule depolymerizer site on tubulin, has no effect on colchicine binding. Similarly, NT-7-16 inhibits colchicine binding in a concentration-dependent manner, consistent with occupancy of the colchicine site on tubulin. At 10 μM, NT-7-16 was able to inhibit approximately 80% of colchicine binding and shows activity comparable to CA-4.

Example 30

In Vivo Activity from Animal Cancer Model Studies

Figure 11A:
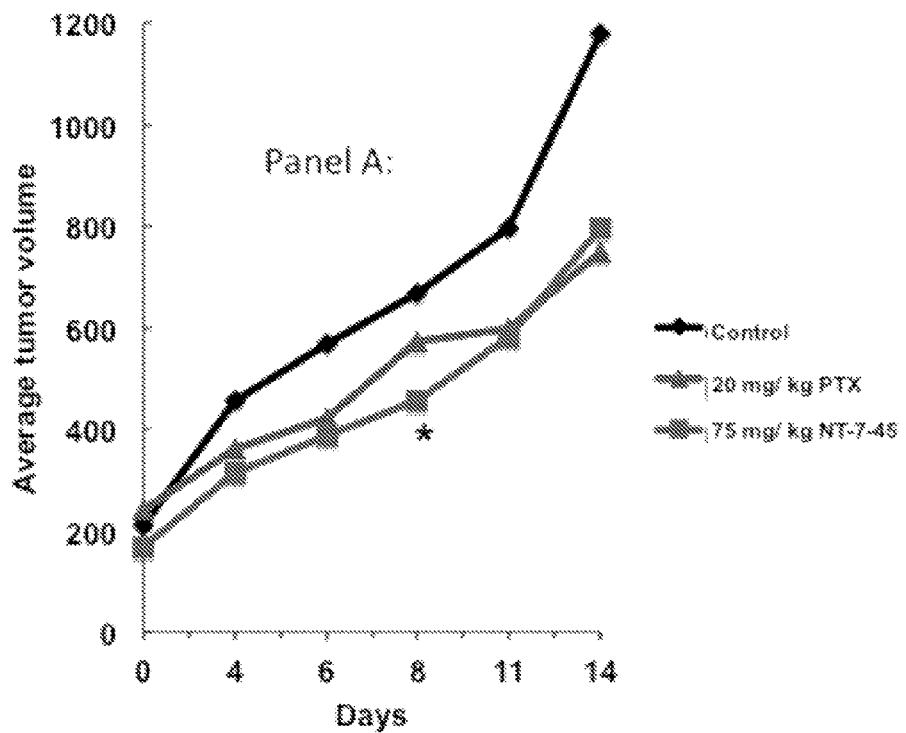
FIG. 11 is a graph showing the in vivo antitumor effects of NT-7-45 on tumor volume growth over a 14-day interval in a murine MDA-MB-435 xenograft model compared with paclitaxel treatment or untreated control. Six periodic intraperitoneal (i.p.) injections of 75 mg/kg NT-7-45 on days 1, 4, 6, 8, 11, and 14 prevented tumor growth, demonstrating that NT-7-45 has antitumor effects at this dose and schedule against the MDA-MB-435 model.
Figure 11B:
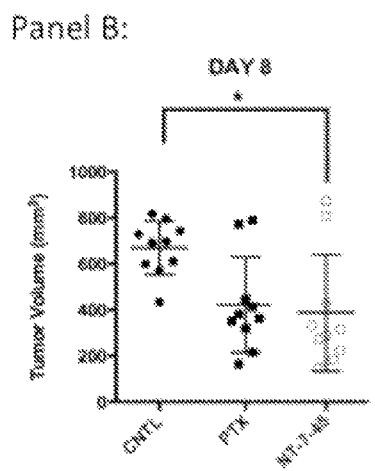
Figure 12:
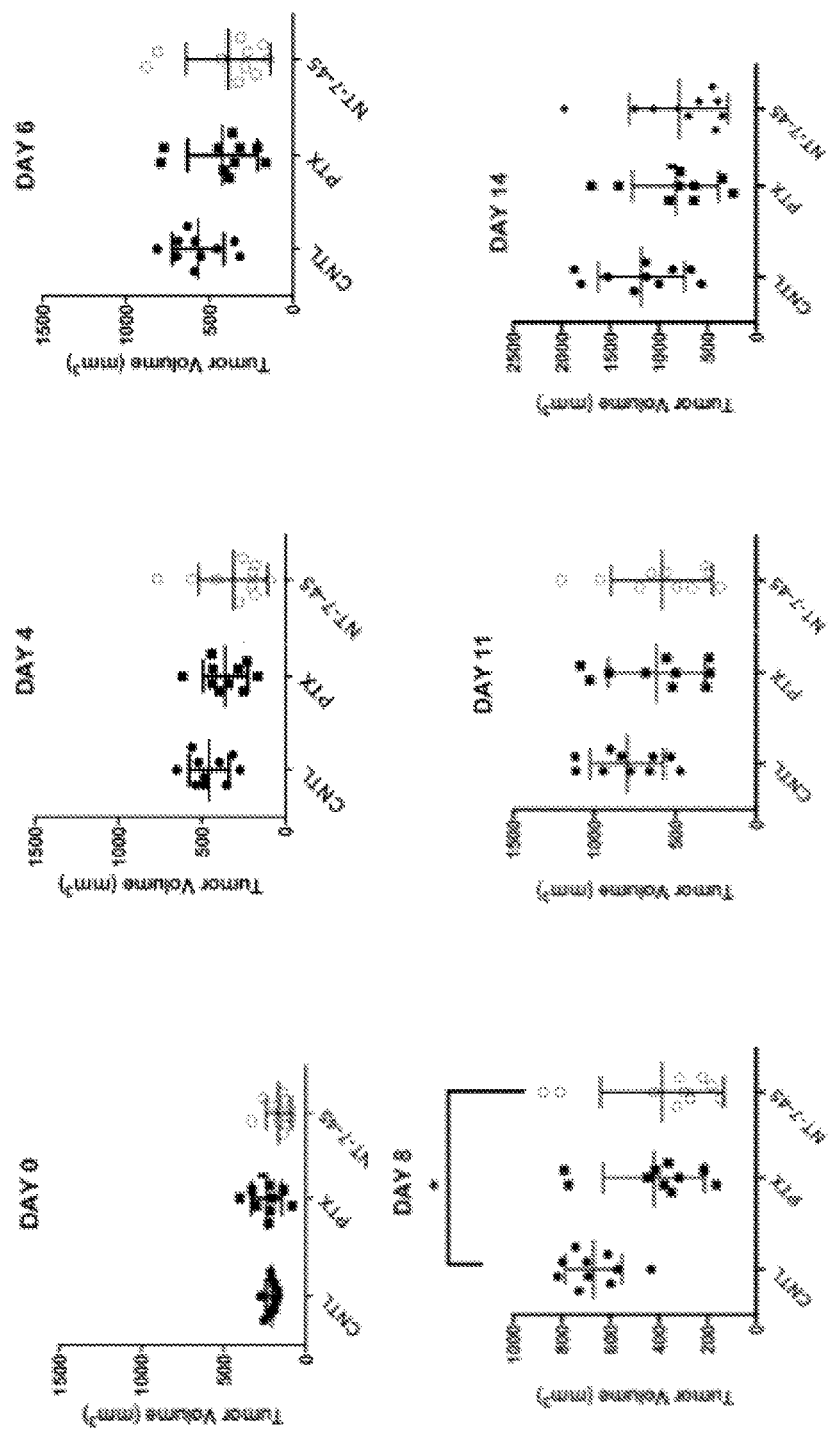
FIG. 12 shows individual, normalized tumor weights, mean and standard deviations on days 0, 4, 6, 8, 11 and 14 of the MDA-MB-435 tumors in mice, showing statistically significant ($p<0.05$) inhibition of tumor growth in the NT-7-45-treated group on day 8.

The antitumor activity of NT-7-45 was evaluated in the MDA-MB-435 xenograft murine model of cancer. MDA-MB-435 cells were implanted subcutaneously into both flanks of nude mice. Mice were treated periodically with six injections of NT-7-45 i.p. at 75 mg/kg, suspended in a mixture of Tween80, DMSO and PBS. A corresponding group of mice were treated every other day with paclitaxel (PTX) suspended in a 50:50 mixture of ethanol:Cremophore at 20 mg/kg. The results are shown in FIG. 11 and FIG. 12. NT-7-45 significantly ($p<0.05$) inhibited tumor growth at day 8 in this 14-day model with no evidence of overt toxicity after these cumulative doses over the time period of treatment.

Figure 4:
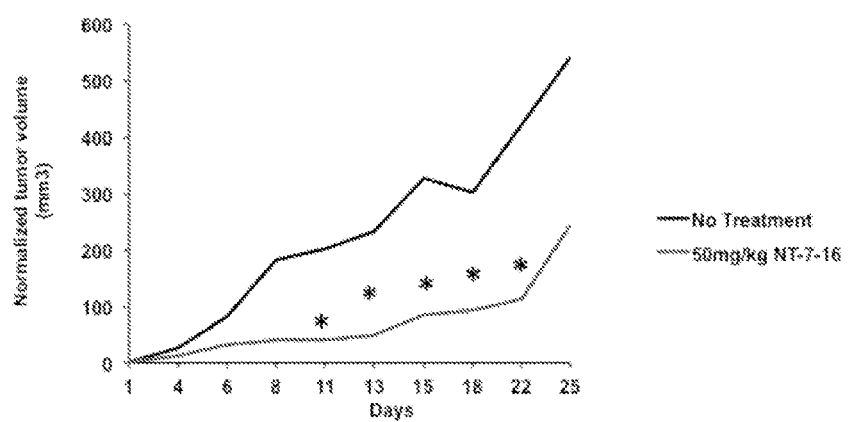
FIG. 4 is a graph showing the in vivo antitumor effects of NT-7-16 on tumor volume growth over a 25-day interval in a murine MDA-MB-435 xenograft model compared with no treatment. Eight periodic intraperitoneal (i.p.) injections of 50 mg/kg NT-7-16 on days 1, 4, 7, 11, 14, 18, 20, and 22, prevented tumor growth, demonstrating that NT-7-16 has antitumor effects at this dose and schedule against the MDA-MB-435 model.
Figure 5A:
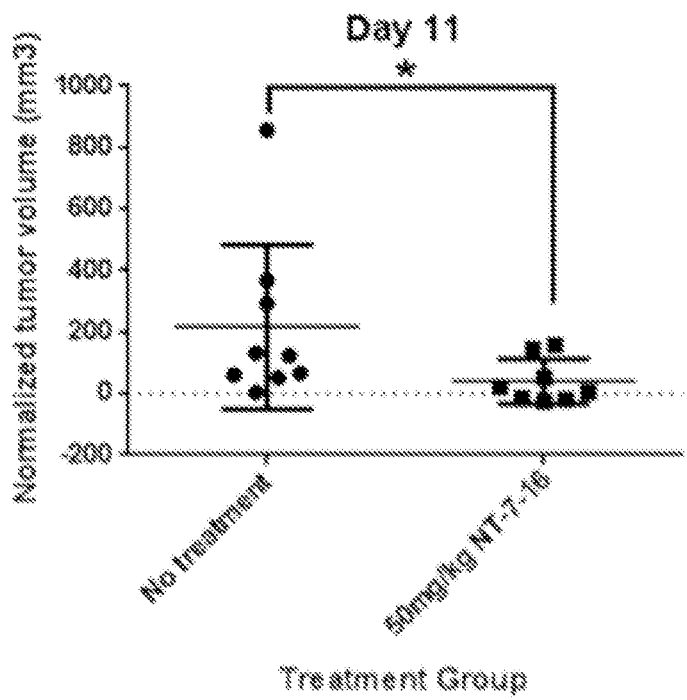
FIG. 5 shows individual, normalized tumor weights, mean and standard deviations of days 11 and 13 of the MDA-MB-435 tumors in mice, showing statistically significant ($p<0.05$) inhibition of tumor growth in the NT-7-16-treated group on these days.
Figure 5B:
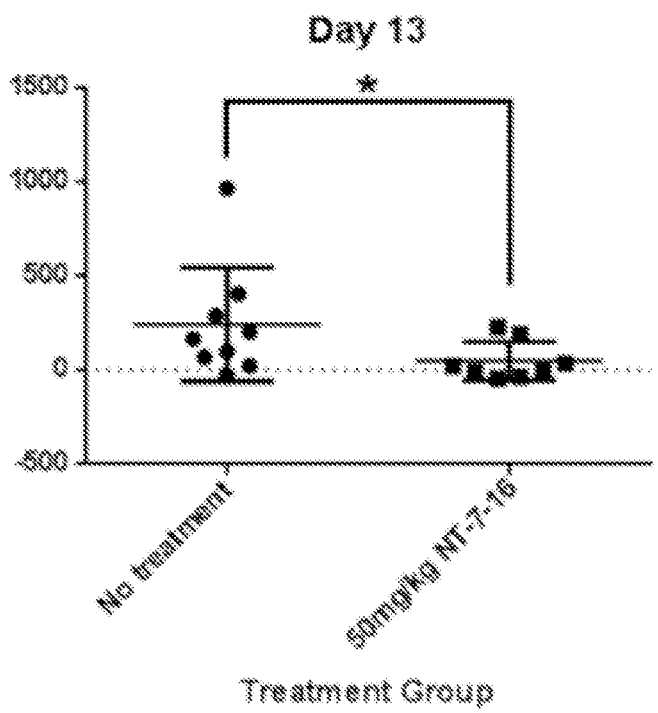
Figure 6A:
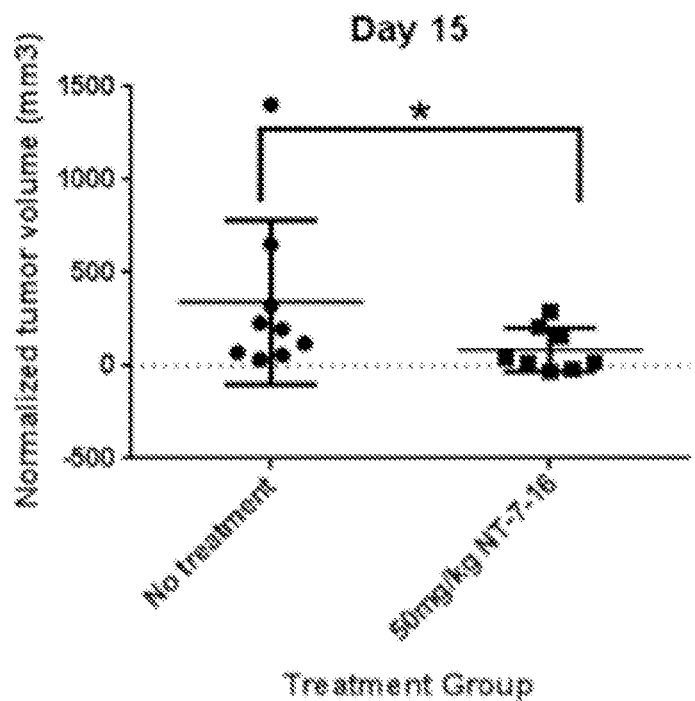
FIG. 6 shows individual, normalized tumor weights, mean and standard deviations of MDA-MB-435 tumors in mice of days 15 and 18, showing statistically significant ($p<0.05$) inhibition of tumor growth at days 15 and 18 in the NT-7-16-treated group.
Figure 6B:
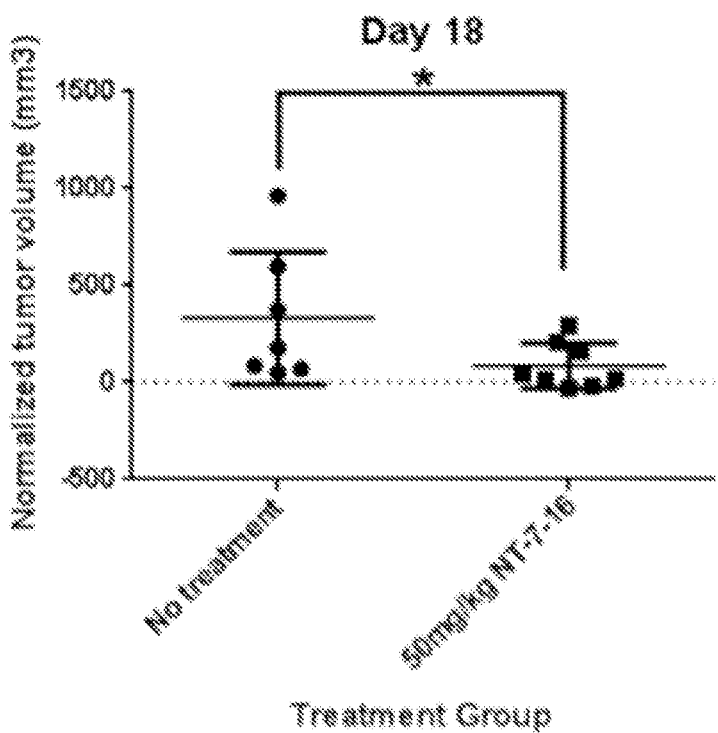
Figure 7A:
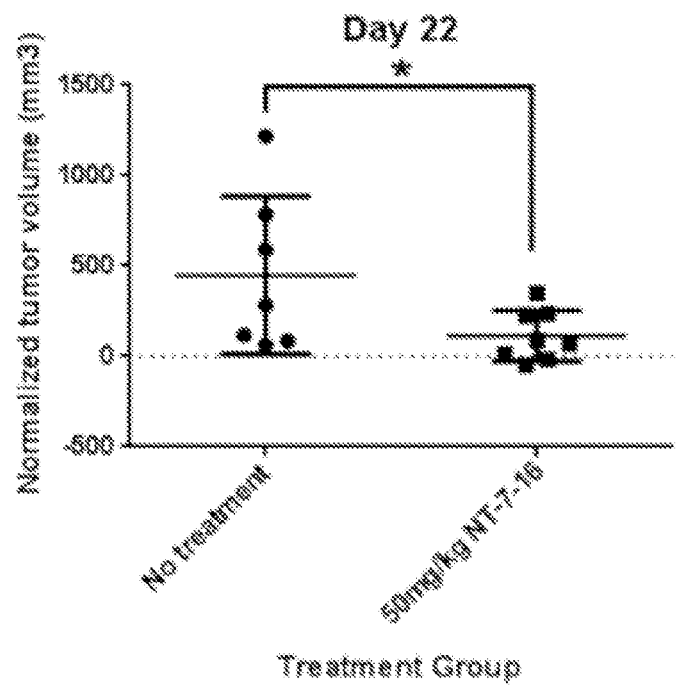
FIG. 7 shows MDA-MB-435 normalized tumor weights, mean and standard deviations of the groups at days 22 and 25, showing statistically significant ($p<0.05$) inhibition of tumor growth in the NT-7-16-treated group as compared to control up to day 22.
Figure 7B:
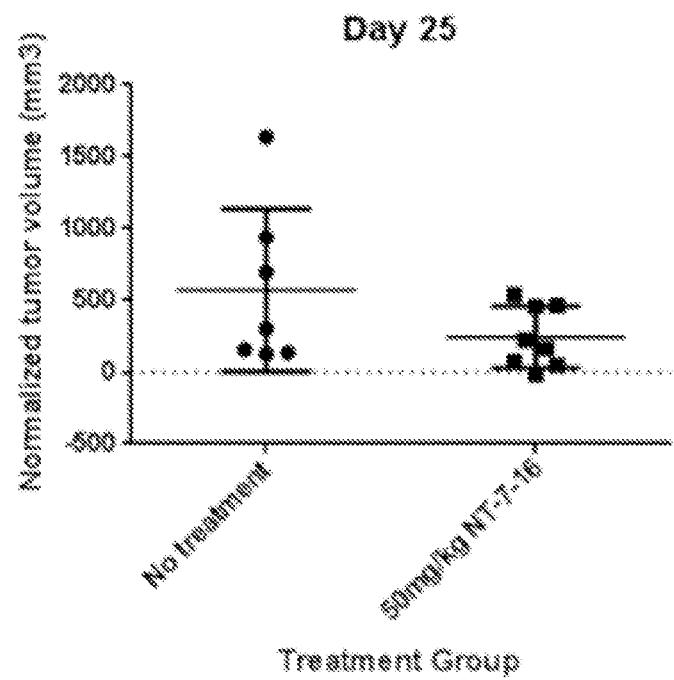
Figure 8:
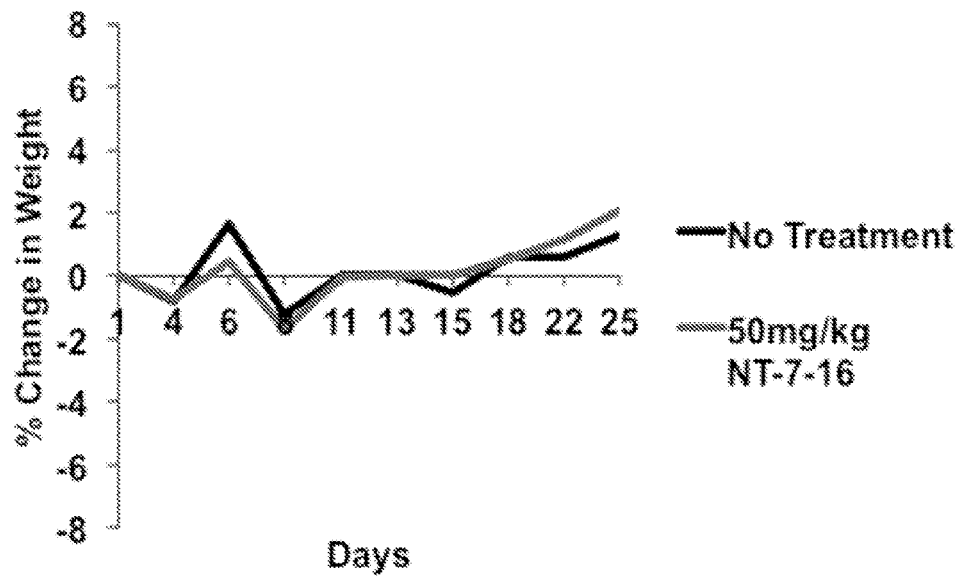
FIG. 8 shows the effects of NT-7-16-treatment on the percent change in animal weight over the 25 days of the MDA-MB-435 xenograft model, demonstrating that NT-7-16 exhibits no significant weight loss, which is indicative of no overt toxicity after 25 days at this dose.

The antitumor activity of NT-7-16 was evaluated in the MDA-MB-435 xenograft murine model of cancer. MDA-MB-435 cells were implanted subcutaneously into both flanks of nude mice. Mice were treated on days 1, 4, 7, 11, 14, 18, 20 and 22 by injecting NT-7-16 i.p. at 50 mg/kg suspended in a mixture of Tween80, DMSO and PBS. Eight cumulative doses of NT-7-16 showed significant antitumor effects (FIG. 4) in this model after 22 days with no evidence of toxicity. As shown in FIG. 5-7, NT-7-16 inhibited tumor growth as compared to vehicle-treated controls in a statistically significant ($p<0.05$) manner at days 11, 13, 15, 18 and 22. As shown in FIG. 8, there was no significant change in animal body weight during the dosing period indicating that NT-7-16 exhibited no overt toxic effects from these cumulative doses over the time period of the experiment.

Based on these data, new polysubstituted 4-(2,3,4-trimethoxyphenyl)pyrrole compounds have been designed, synthesized, and tested and found to be effective microtubule-depolymerizing agents. The data also demonstrate that several of these polysubstituted 4-(2,3,4-trimethoxyphenyl)pyrrole compounds interact directly with purified tubulin and inhibit tubulin polymerization in vitro. Notably, several examples were identified with surprisingly potent in vitro antiproliferative activities with $IC_{50}$ values in the low nanomolar range. The significantly lower $EC_{50}/IC_{50}$ ratio exhibited by many of these unsymmetrical polysubstituted 4-(2,3,4-trimethoxy)phenyl-pyrrole compounds clearly demonstrates that most, if not all, of their antiproliferative in vitro activity can be attributed to their ability to inhibit microtubule-dependent processes. These new unsymmetrical polysubstituted 4-(2,3,4-trimethoxy-phenyl)pyrrole compounds are also effective in two cell models of clinically relevant drug resistance to microtubule-targeting agents: the drug efflux pump P-glycoprotein, and the tubulin βIII isotype of tubulin. Unlike clinical preparations of paclitaxel and vinblastine, the compounds of the invention are thus able to overcome clinically relevant drug-resistance mechanisms, including the expression of P-glycoprotein and the βIII isotype of tubulin.

As described herein, compounds of the invention have also demonstrated antitumor activity in vivo. Short-term (14-day) treatment data are provided herein, demonstrating that NT-7-45 has statistically significant antitumor effects at day-8 against MDA-MB-435 in a xenograft, drug-sensitive murine model of in vivo tumor progression.

What is claimed is:
1. A compound of Formula II:

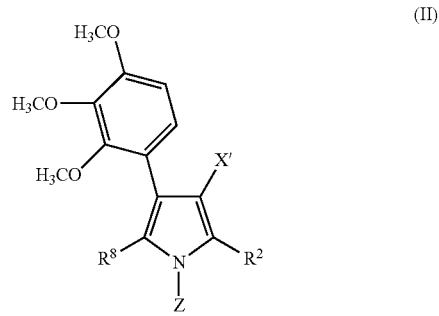

or its pharmaceutically acceptable salt, solvate or hydrate, wherein:
Z is H;
X' is independently selected from the group halo;
$R^2$ is independently selected from the group consisting of —C(O)—$OR^3$ and cyano;
$R^3$ is independently selected from the group consisting of $C_1$-$C_5$ straight alkyl;
$R^8$ is independently selected from the group consisting of HC(NO$R^7$), $C_1$-$C_5$ straight alkyl, $C_3$-$C_5$ branched alkyl, $C_3$-$C_5$ cyclic alkyl, alkenyl, alkynyl, hydroxyalkyl, alkoxyalkyl, haloalkyl, aminoalkyl, alkylaminoalkyl, dialkylaminoalkyl, amidoalkyl, carboxyalkyl, alkoxycarbonylalkyl, acyloxyalkyl, sulfonylalkyl, heteroaryl, heteroaroyl, heteroaralkyl, heterocycle, —(CO)heterocycle and heterocyclicalkyl, wherein all may be optionally substituted by one or more independently selected from the group consisting of halo, alkyl, acyl, alkanoyl, hydroxy, alkoxy, hydroxyalkyl, heterocyclic, heteroaryl, amino, aminoalkyl, alkylamino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, —SO$_3$H, and oximino, O-methyl-oximino, O-ethyl-oximino, O-n-propyl-oximino;

R$^7$ is independently selected from the group consisting of alkyl, wherein all may be substituted by one or more independently selected from the group consisting of halo, lower alkyl, acyl, oxo, alkoxy, hydroxy, hydroxyalkyl, imino, amino, aminoalkyl, and carboxy.

2. The compound of claim 1, wherein:

R$^8$ is independently selected from the group consisting of HC(NOR$^7$), amidoalkyl, aminoalkyl, and alkylaminoalkyl, wherein all may be optionally substituted by one or more independently selected from the group consisting of acyl, alkanoyl, hydroxy, alkoxy, hydroxyalkyl, heterocyclic, heteroaryl, amino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, —SO$_3$H, and oximino.

3. The compound of claim 1, wherein:

X' is bromo or chloro;

R$^3$ is independently selected from the group consisting of methyl, ethyl and n-propyl;

R$^8$ is independently selected from the group consisting of oximino, O-methyl-oximino, O-ethyl-oximino, O-n-propyl-oximino, aminomethyl, aminoethyl, aminopropyl, aminobutyl, methylaminomethyl, ethylaminomethyl, propylaminomethyl, butylaminommethyl, methylaminoethyl, ethylaminoethyl, propylaminoethyl, butylaminoethyl, methylaminopropyl, ethylaminopropyl, propylaminopropyl, butylaminopropyl, methylaminobutyl, ethylaminobutyl, propylaminobutyl and butylaminobutyl, wherein all may be optionally substituted by one or more independently selected from the group consisting of acyl, alkanoyl, hydroxy, alkoxy, hydroxyalkyl, heterocyclic, heteroaryl, amino, imino, oxo, cyano, carboxy, carboxyalkyl, alkoxycarbonyl, —OPO$_3$H$_2$, —PO$_4$H$_2$, —PO$_3$H$_2$, —P(R$^7$)O$_2$H, —OSO$_3$H, and —SO$_3$H.

4. The compound of claim 1, wherein the compound is selected from the group consisting of:

5-Oximino-3-bromo-4-(2,3,4-trimethoxyphenyl)-1H-pyrrole 2-carboxylic acid ethyl ester, 5-(O-Methyl-oximino)-3-bromo-4-(2, 3 ,4-trimethoxyphenyl)-1H-pyrrole-2-carboxylic acid ethyl ester, 5 -Oximino-3-chloro-4-(2,3 ,4-trimethoxyphenyl)-1H-pyrrole-2-carboxylic acid ethyl ester, 5-(Aminomethylene)-3-bromo-4-(2, 3 ,4-trimethoxyphenyl)-1H-pyrrole-2-carboxylic acid ethyl ester; 5-(Aminomethylene)-3-chloro-4-(2,3 ,4-trimethoxyphenyl)-1H-pyrrole-2-carboxylic acid ethyl ester; 5-(n-Propylaminomethylene)-3-Bromo-4-(2, 3 , 4-trimethoxyphenyl)-1H -pyrrole-2 -carboxylic acid ethyl ester; 5-(n-Propylaminomethylene)-3-Chloro-4-(2, 3 ,4-trimethoxyphenyl)-1H-pyrrole-2-carboxylic acid ethyl ester; 5-[N-((2-Aminoethyl)amino)methylene]-3-bromo-4 -(2,3 ,4-trimethoxyphenyl)-1H-pyrrole-2-carboxylic acid ethyl ester; and 5-[((N-2-tert-butoxycarbonylamino)-ethylamino)-methylene]-3-bromo-4-(2,3,4-trimethoxy-phenyl)-1H-pyrrole 2-carboxylic acid ethyl ester.

5. A pharmaceutical composition comprising a therapeutically effective amount of a compound of claim 1 and a pharmaceutically acceptable carrier.

6. The pharmaceutical composition of claim 5, in a form suitable for oral, parenteral, intravenous, intradermal, transdermal, subcutaneous or topical administration.

7. A method of treating a breast cancer patient comprising administering to a patient in need thereof a therapeutically effective amount of a compound of claim 1.

8. The method of claim 7, wherein the compound is selected from the group consisting of:

5-Oximino-3-bromo-4-(2, 3 ,4-trimethoxyphenyl)-1H-pyrrole-2-carboxylic acid ethyl ester; 5 -(O-Methyl-oximino)-3-bromo-4-(2, 3 ,4-trimethoxyphenyl)-1H-pyrrole-2-carboxylic acid ethyl ester; 5-Oximino-3-chloro-4-(2,3 ,4-trimethoxyphenyl)-1H-pyrrole-2-carboxylic acid ethyl ester; 5-(Aminomethylene)-3-bromo-4-(2, 3 ,4-trimethoxyphenyl)-1H-pyrrole-2-carboxylic acid ethyl ester; 5-(Aminomethylene)-3-chloro-4-(2,3 ,4-trimethoxyphenyl)-1H-pyrrole-2-carboxylic acid ethyl ester; 5-(n-Propylaminomethylene)-3-Bromo -4- (2, 3 , 4-trimethoxyphenyl)-1H-pyrrole-2 -carboxylic acid ethyl ester;

5-(n-Propylaminomethylene)-3-Chloro-4-(2, 3, 4-trimethoxyphenyl)-1H-pyrrole-2-carboxylic acid ethyl ester; 5-[N-((2-Aminoethyl)amino)methylene]-3-bromo-4-(2,3,4-trimethoxyphenyl)-1H-pyrrole-2-carboxylic acid ethyl ester; and 5-[((N-2-tert-butoxycarbonylamino)-ethylamino) -methylene]-3-bromo-4-(2,3 ,4-trimethoxy-phenyl)-1H-pyrrole 2-carboxylic acid ethyl ester.

9. A compound of Formula I:

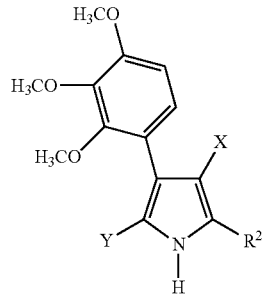

Formula I wherein:

X and Y are the same and are independently selected from the group halo;

R$^2$ is independently selected from the group consisting of —C(O)—OR$^3$;

R$^3$ is independently selected from the group consisting of C$_1$-C$_5$ straight alkyl.

10. The compound of claim 9 wherein:

X and Y are the same and are selected from the group consisting of bromo and chloro; and R$^3$ is independently selected from the group consisting of methyl, ethyl and n-propyl.

11. The compound of claim 9, wherein the compound is 3,5-Dibromo-4-(2,3,4 -trimethoxyphenyl)-1H-pyrrole-2-carboxylic acid ethyl ester; and 3,5-Dichloro-4-(2,3,4 -trimethoxyphenyl)-1H-pyrrole-2-carboxylic acid ethyl ester.

12. A method of treating a breast cancer patient comprising administering to a patient in need thereof a therapeutically effective amount of a compound of claim 9.

13. The method of claim 12, wherein the compound is 3,5-Dibromo-4-(2,3, -trimethoxyphenyl)-1H-pyrrole-2-carboxylic acid ethyl ester; 3,5-Dichloro-4-(2,3,4-trimethoxyphenyl)-1H-pyrrole-2-carboxylic acid ethyl ester; or 2-Cyano-3,5-Dibromo-4-(2,3,4-trimethoxyphenyl)-1H-pyrrole.

14. A pharmaceutical composition comprising a therapeutically effective amount of a compound of claim 9 and a pharmaceutically acceptable carrier.

15. The pharmaceutical composition of claim 14 in a form suitable for oral, parenteral, intravenous, intradermal, transdermal, subcutaneous or topical administration.

\* \* \* \* \*